(12) United States Patent
Evans et al.

(10) Patent No.: US 9,737,425 B2
(45) Date of Patent: *Aug. 22, 2017

(54) SYSTEM AND METHODS FOR ENDOVASCULAR ANEURYSM TREATMENT

(71) Applicant: NELLIX, INC., Irvine, CA (US)

(72) Inventors: Michael A. Evans, Palo Alto, CA (US); Gwendolyn A. Wantanabe, Sunnyvale, CA (US); Amy Lee, Sunnyvale, CA (US); Steven L. Herbowy, Palo Alto, CA (US)

(73) Assignee: Nellix, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/537,749

(22) Filed: Nov. 10, 2014

(65) Prior Publication Data

US 2015/0142093 A1 May 21, 2015

Related U.S. Application Data

(60) Continuation of application No. 12/684,074, filed on Jan. 7, 2010, now Pat. No. 8,906,084, which is a
(Continued)

(51) Int. Cl.
*A61F 2/06* (2013.01)
*A61F 2/958* (2013.01)
(Continued)

(52) U.S. Cl.
CPC ........ *A61F 2/958* (2013.01); *A61B 17/12118* (2013.01); *A61B 17/12136* (2013.01);
(Continued)

(58) Field of Classification Search
CPC ...... A61F 2/06; A61F 2/07; A61F 2/82; A61F 2/958; A61F 2002/077; A61F 2250/0003; A61M 2025/0002; A61B 17/12195
See application file for complete search history.

(56) References Cited

U.S. PATENT DOCUMENTS

| 4,565,738 A | 1/1986 | Purdy |
|---|---|---|
| 4,638,803 A | 1/1987 | Rand |
| (Continued) | | |

FOREIGN PATENT DOCUMENTS

| DE | 4010975 A1 | 10/1991 |
|---|---|---|
| EP | 0679372 A2 | 11/1995 |
| (Continued) | | |

OTHER PUBLICATIONS

Carmi et al., "Endovascular stent-graft adapted to the endoluminal environment: prototype of a new endoluminal approach," J Endovasc Ther. Jun. 2002;9(3):380-381.
(Continued)

*Primary Examiner* — David Isabella
*Assistant Examiner* — Dinah Baria
(74) *Attorney, Agent, or Firm* — Kilpatrick, Townsend & Stockton, LLP

(57) ABSTRACT

Methods and systems for treating aneurysms using filling structures filled with a curable medium are described herein. Such methods can include positioning a double-walled filling structure across the aneurysm and filling with a filling medium so that an outer wall conforms to the inside of the aneurysm and an inner wall forms a generally tubular lumen to provide for blood flow. The lumen is supported with a balloon or other expandable device during and/or after filling. The pressure within the structure and/or in the space between an external wall of the structure and the aneurysm wall is monitored and a flow of the medium into the structure is controlled responsive to the pressure. The pressure can also be used to determine a filling endpoint.

25 Claims, 39 Drawing Sheets

Related U.S. Application Data division of application No. 11/482,503, filed on Jul. 7, 2006, now Pat. No. 7,666,220.

(60) Provisional application No. 60/696,818, filed on Jul. 7, 2005, provisional application No. 60/696,817, filed on Jul. 7, 2005.

(51) Int. Cl.
*A61B 17/12* (2006.01)
*A61F 2/07* (2013.01)
*A61F 2/95* (2013.01)
*A61F 2/82* (2013.01)
*A61M 25/00* (2006.01)
*A61F 2/90* (2013.01)

(52) U.S. Cl.
CPC .......... *A61B 17/12195* (2013.01); *A61F 2/06* (2013.01); *A61F 2/07* (2013.01); *A61F 2/82* (2013.01); *A61F 2/95* (2013.01); *A61B 2017/1205* (2013.01); *A61F 2/90* (2013.01); *A61F 2002/065* (2013.01); *A61F 2002/067* (2013.01); *A61F 2002/077* (2013.01); *A61F 2220/005* (2013.01); *A61F 2220/0058* (2013.01); *A61F 2230/005* (2013.01); *A61F 2230/0034* (2013.01); *A61F 2250/0003* (2013.01); *A61M 2025/0002* (2013.01)

(56) References Cited

U.S. PATENT DOCUMENTS

| | | |
|---|---|---|
| 4,641,653 A | 2/1987 | Rockey |
| 4,704,126 A | 11/1987 | Baswell |
| 4,710,192 A | 12/1987 | Liotta |
| 4,728,328 A | 3/1988 | Hughes et al. |
| 4,731,073 A | 3/1988 | Robinson |
| 4,733,665 A | 3/1988 | Palmaz |
| 4,743,258 A | 5/1988 | Ikada |
| 4,763,654 A | 8/1988 | Jang |
| 4,856,516 A | 8/1989 | Hillstead |
| 4,858,264 A | 8/1989 | Reinhart |
| 4,892,544 A | 1/1990 | Frisch |
| 4,936,057 A | 6/1990 | Rhoades |
| 4,976,692 A | 12/1990 | Atad |
| 5,002,532 A | 3/1991 | Gaiser |
| 5,074,845 A | 12/1991 | Miraki |
| 5,104,404 A | 4/1992 | Wolff |
| 5,108,417 A | 4/1992 | Sawyer |
| 5,122,154 A | 6/1992 | Rhodes |
| 5,133,732 A | 7/1992 | Wiktor |
| 5,139,480 A | 8/1992 | Hickle |
| 5,156,620 A | 10/1992 | Pigott |
| 5,195,984 A | 3/1993 | Schatz |
| 5,199,226 A | 4/1993 | Rose |
| 5,217,484 A | 6/1993 | Marks |
| 5,222,970 A | 6/1993 | Reeves |
| 5,234,437 A | 8/1993 | Sepetka |
| 5,242,399 A | 9/1993 | Lau |
| 5,250,071 A | 10/1993 | Palermo |
| 5,261,916 A | 11/1993 | Engelson |
| 5,263,964 A | 11/1993 | Purdy |
| 5,292,331 A | 3/1994 | Boneau |
| 5,314,444 A | 5/1994 | Gianturco |
| 5,316,023 A | 5/1994 | Palmaz et al. |
| 5,330,528 A | 7/1994 | Lazim |
| 5,334,024 A | 8/1994 | Niznick |
| 5,334,217 A | 8/1994 | Das |
| 5,350,397 A | 9/1994 | Palermo |
| 5,352,199 A | 10/1994 | Tower |
| 5,375,612 A | 12/1994 | Cottenceau |
| 5,383,892 A | 1/1995 | Cardon |
| 5,421,955 A | 6/1995 | Lau |
| 5,423,849 A | 6/1995 | Engelson |
| 5,425,739 A | 6/1995 | Jessen |
| 5,425,744 A | 6/1995 | Fagan |
| 5,441,510 A | 8/1995 | Simpson |
| 5,441,515 A | 8/1995 | Khosravi |
| 5,443,477 A | 8/1995 | Marin |
| 5,443,496 A | 8/1995 | Schwartz |
| 5,449,373 A | 9/1995 | Pinchasik |
| 5,485,667 A | 1/1996 | Kleshinski |
| 5,494,029 A | 2/1996 | Lane |
| 5,496,277 A | 3/1996 | Termin |
| 5,507,767 A | 4/1996 | Maeda |
| 5,507,769 A | 4/1996 | Marin et al. |
| 5,507,771 A | 4/1996 | Gianturco |
| 5,514,115 A | 5/1996 | Frantzen |
| 5,514,154 A | 5/1996 | Lau |
| 5,522,882 A | 6/1996 | Gaterud |
| 5,530,528 A | 6/1996 | Houki et al. |
| 5,531,741 A | 7/1996 | Barbacci |
| 5,534,024 A | 7/1996 | Rogers et al. |
| 5,545,210 A | 8/1996 | Hess |
| 5,549,662 A | 8/1996 | Fordenbacher |
| 5,549,663 A | 8/1996 | Cottone, Jr. |
| 5,554,181 A | 9/1996 | Das |
| 5,562,641 A | 10/1996 | Flomenblit |
| 5,562,698 A | 10/1996 | Parker |
| 5,562,728 A | 10/1996 | Lazarus |
| 5,569,295 A | 10/1996 | Lam |
| 5,578,074 A | 11/1996 | Mirigian |
| 5,578,149 A | 11/1996 | De Scheerder |
| 5,591,195 A | 1/1997 | Taheri |
| 5,591,223 A | 1/1997 | Lock |
| 5,591,226 A | 1/1997 | Trerotola |
| 5,591,228 A | 1/1997 | Edoga |
| 5,591,230 A | 1/1997 | Horn |
| 5,593,417 A | 1/1997 | Rhodes |
| 5,601,600 A | 2/1997 | Ton |
| 5,603,721 A | 2/1997 | Lau |
| 5,605,530 A | 2/1997 | Fischell |
| 5,607,442 A | 3/1997 | Fischell |
| 5,607,445 A | 3/1997 | Summers |
| 5,607,468 A | 3/1997 | Rogers |
| 5,609,605 A | 3/1997 | Marshall |
| 5,617,878 A | 4/1997 | Taheri |
| 5,618,299 A | 4/1997 | Khosravi |
| 5,624,411 A | 4/1997 | Tuch |
| 5,630,840 A | 5/1997 | Mayer |
| 5,632,760 A | 5/1997 | Sheiban |
| 5,632,762 A | 5/1997 | Myler |
| 5,632,763 A | 5/1997 | Glastra |
| 5,632,771 A | 5/1997 | Boatman |
| D380,266 S | 6/1997 | Boatman |
| 5,634,941 A | 6/1997 | Winston |
| 5,636,641 A | 6/1997 | Fariabi |
| D380,831 S | 7/1997 | Kavteladze |
| 5,662,614 A | 9/1997 | Edoga |
| 5,665,117 A | 9/1997 | Rhodes |
| 5,674,241 A | 10/1997 | Bley |
| 5,676,697 A | 10/1997 | McDonald |
| 5,683,449 A | 11/1997 | Marcade |
| 5,690,643 A | 11/1997 | WiJay |
| 5,693,038 A | 12/1997 | Suzuki et al. |
| 5,693,067 A | 12/1997 | Purdy |
| 5,693,088 A | 12/1997 | Lazarus |
| 5,697,971 A | 12/1997 | Fischell |
| 5,709,707 A | 1/1998 | Lock |
| 5,718,713 A | 2/1998 | Frantzen |
| 5,723,004 A | 3/1998 | Dereume |
| 5,725,568 A | 3/1998 | Hastings |
| 5,725,572 A | 3/1998 | Lam |
| 5,728,068 A | 3/1998 | Leone |
| 5,728,131 A | 3/1998 | Frantzen |
| 5,728,158 A | 3/1998 | Lau |
| 5,733,303 A | 3/1998 | Israel et al. |
| 5,735,892 A | 4/1998 | Myers |
| 5,735,893 A | 4/1998 | Lau |
| 5,741,327 A | 4/1998 | Frantzen |
| 5,741,333 A | 4/1998 | Frid |
| 5,746,691 A | 5/1998 | Frantzen |
| 5,755,769 A | 5/1998 | Richard |

(56) References Cited

U.S. PATENT DOCUMENTS

| | | |
|---|---|---|
| 5,755,773 A | 5/1998 | Evans et al. |
| 5,755,778 A | 5/1998 | Kleshinski |
| 5,766,151 A | 6/1998 | Valley et al. |
| 5,766,238 A | 6/1998 | Lau |
| 5,769,882 A | 6/1998 | Fogarty et al. |
| 5,776,114 A | 7/1998 | Frantzen |
| 5,776,161 A | 7/1998 | Globerman |
| 5,782,907 A | 7/1998 | Frantzen |
| 5,785,679 A | 7/1998 | Abolfathi et al. |
| 5,788,626 A | 8/1998 | Thompson |
| 5,797,953 A | 8/1998 | Tekulve |
| 5,800,393 A | 9/1998 | Sahota |
| 5,800,512 A | 9/1998 | Lentz et al. |
| 5,800,514 A | 9/1998 | Nunez |
| 5,800,525 A | 9/1998 | Bachinski |
| 5,807,404 A | 9/1998 | Richter |
| 5,810,872 A | 9/1998 | Kanesaka |
| 5,824,036 A | 10/1998 | Lauterjung |
| 5,824,037 A | 10/1998 | Fogarty et al. |
| 5,824,040 A | 10/1998 | Cox |
| 5,824,049 A | 10/1998 | Ragheb |
| 5,824,054 A | 10/1998 | Khosravi et al. |
| 5,824,056 A | 10/1998 | Rosenberg |
| 5,827,321 A | 10/1998 | Roubin |
| 5,836,966 A | 11/1998 | St. Germain |
| 5,843,160 A | 12/1998 | Rhodes |
| 5,843,175 A | 12/1998 | Frantzen |
| 5,846,246 A | 12/1998 | Dirks |
| 5,846,261 A | 12/1998 | Kotula et al. |
| 5,849,037 A | 12/1998 | Frid |
| 5,860,998 A | 1/1999 | Robinson |
| 5,863,627 A | 1/1999 | Szycher |
| 5,867,762 A | 2/1999 | Rafferty et al. |
| 5,868,685 A | 2/1999 | Powell et al. |
| 5,868,708 A | 2/1999 | Hart |
| 5,868,782 A | 2/1999 | Frantzen |
| 5,871,537 A | 2/1999 | Holman |
| 5,873,907 A | 2/1999 | Frantzen |
| 5,876,448 A | 3/1999 | Thompson et al. |
| 5,879,381 A | 3/1999 | Moriuchi |
| 5,888,660 A | 3/1999 | Landoni et al. |
| 5,902,332 A | 5/1999 | Schatz |
| 5,919,224 A | 7/1999 | Thompson |
| 5,928,279 A | 7/1999 | Shannon et al. |
| 5,931,866 A | 8/1999 | Frantzen |
| 5,944,750 A | 8/1999 | Tanner |
| 5,947,991 A | 9/1999 | Cowan |
| 5,948,184 A | 9/1999 | Frantzen |
| 5,976,178 A | 11/1999 | Goldsteen et al. |
| 5,984,955 A | 11/1999 | Wisselink |
| 5,994,750 A | 11/1999 | Yagi |
| 6,007,573 A | 12/1999 | Wallace |
| 6,015,431 A | 1/2000 | Thornton |
| 6,022,359 A | 2/2000 | Frantzen |
| 6,033,434 A | 3/2000 | Borghi |
| 6,042,606 A | 3/2000 | Frantzen |
| 6,056,776 A | 5/2000 | Lau |
| 6,066,167 A | 5/2000 | Lau |
| 6,066,168 A | 5/2000 | Lau |
| 6,083,259 A | 7/2000 | Frantzen |
| 6,093,199 A | 7/2000 | Brown |
| 6,099,548 A | 8/2000 | Taheri |
| 6,110,198 A | 8/2000 | Fogarty et al. |
| 6,123,715 A | 9/2000 | Amplatz |
| 6,123,722 A | 9/2000 | Fogarty |
| 6,124,523 A | 9/2000 | Banas et al. |
| 6,132,457 A | 10/2000 | Chobotov |
| 6,152,144 A | 11/2000 | Lesh |
| 6,152,943 A | 11/2000 | Sawhney |
| 6,168,592 B1 | 1/2001 | Kupiecki et al. |
| 6,187,033 B1 | 2/2001 | Schmitt |
| 6,187,034 B1 | 2/2001 | Frantzen |
| 6,190,402 B1 | 2/2001 | Horton et al. |
| 6,190,406 B1 | 2/2001 | Duerig et al. |
| 6,193,745 B1 | 2/2001 | Fogarty et al. |
| 6,196,230 B1 | 3/2001 | Hall et al. |
| 6,203,732 B1 | 3/2001 | Clubb |
| 6,214,022 B1 | 4/2001 | Taylor et al. |
| 6,231,562 B1 | 5/2001 | Khosravi et al. |
| 6,235,050 B1 | 5/2001 | Quiachon et al. |
| 6,241,761 B1 | 6/2001 | Villafana |
| 6,254,633 B1 | 7/2001 | Pinchuk et al. |
| 6,261,305 B1 | 7/2001 | Marotta et al. |
| 6,280,466 B1 | 8/2001 | Kugler |
| 6,283,991 B1 | 9/2001 | Cox et al. |
| 6,290,722 B1 | 9/2001 | Wang |
| 6,290,731 B1 | 9/2001 | Solovay et al. |
| 6,293,960 B1 | 9/2001 | Ken |
| 6,296,603 B1 | 10/2001 | Turnlund et al. |
| 6,299,597 B1 | 10/2001 | Buscemi et al. |
| 6,299,604 B1 | 10/2001 | Ragheb |
| 6,312,462 B1 | 11/2001 | McDermott et al. |
| 6,312,463 B1 | 11/2001 | Rourke et al. |
| 6,325,816 B1 | 12/2001 | Fulton, III |
| 6,325,819 B1 | 12/2001 | Pavcnik et al. |
| 6,331,184 B1 | 12/2001 | Abrams |
| 6,331,191 B1 | 12/2001 | Chobotov |
| 6,334,869 B1 | 1/2002 | Leonhardt et al. |
| 6,344,056 B1 | 2/2002 | Dehdashtian |
| 6,375,675 B2 | 4/2002 | Dehdashtian et al. |
| 6,395,019 B2 | 5/2002 | Chobotov |
| 6,409,757 B1 | 6/2002 | Trout, III et al. |
| 6,432,131 B1 | 8/2002 | Ravenscroft |
| 6,451,047 B2 | 9/2002 | McCrea |
| 6,463,317 B1 | 10/2002 | Kucharczyk et al. |
| 6,506,204 B2 | 1/2003 | Mazzocchi |
| 6,527,799 B2 | 3/2003 | Shanley |
| 6,544,276 B1 | 4/2003 | Azizi |
| 6,547,804 B2 | 4/2003 | Porter et al. |
| 6,554,858 B2 | 4/2003 | Dereume et al. |
| 6,576,007 B2 | 6/2003 | Dehdashtian et al. |
| 6,579,301 B1 | 6/2003 | Bales |
| 6,592,614 B2 | 7/2003 | Lenker et al. |
| 6,613,037 B2 | 9/2003 | Khosravi et al. |
| 6,645,242 B1 | 11/2003 | Quinn |
| 6,656,214 B1 | 12/2003 | Fogarty et al. |
| 6,656,220 B1 | 12/2003 | Gomez et al. |
| 6,663,607 B2 | 12/2003 | Slaikeu et al. |
| 6,663,667 B2 | 12/2003 | Dehdashtian et al. |
| 6,679,300 B1 | 1/2004 | Sommer et al. |
| 6,682,546 B2 | 1/2004 | Amplatz |
| 6,692,486 B2 | 2/2004 | Jaafar et al. |
| 6,695,833 B1 | 2/2004 | Frantzen |
| 6,729,356 B1 | 5/2004 | Baker et al. |
| 6,730,119 B1 | 5/2004 | Smalling |
| 6,733,521 B2 | 5/2004 | Chobotov |
| 6,761,733 B2 | 7/2004 | Chobotov |
| 6,773,454 B2 | 8/2004 | Wholey et al. |
| 6,776,771 B2 | 8/2004 | Van Moorlegem et al. |
| 6,827,735 B2 | 12/2004 | Greenberg |
| 6,843,803 B2 | 1/2005 | Ryan et al. |
| 6,878,161 B2 | 4/2005 | Lenker |
| 6,878,164 B2 | 4/2005 | Kujawski |
| 6,887,268 B2 | 5/2005 | Butaric et al. |
| 6,918,926 B2 | 7/2005 | Letort |
| 6,945,989 B1 | 9/2005 | Betelia et al. |
| 6,958,051 B2 | 10/2005 | Hart et al. |
| 6,960,227 B2 | 11/2005 | Jones et al. |
| 6,964,667 B2 | 11/2005 | Shaolian et al. |
| 7,001,431 B2 | 2/2006 | Bao et al. |
| 7,022,100 B1 | 4/2006 | Aboul-Hosn et al. |
| 7,105,012 B2 | 9/2006 | Trout, III |
| 7,112,217 B1 | 9/2006 | Kugler |
| 7,122,052 B2 | 10/2006 | Greenhalgh |
| 7,131,991 B2 | 11/2006 | Zarins et al. |
| 7,147,661 B2 | 12/2006 | Chobotov et al. |
| 7,175,651 B2 | 2/2007 | Kerr |
| 7,229,472 B2 | 6/2007 | DePalma et al. |
| 7,314,483 B2 | 1/2008 | Landau et al. |
| 7,326,237 B2 | 2/2008 | Depalma et al. |
| 7,435,253 B1 | 10/2008 | Hartley et al. |
| 7,530,988 B2 | 5/2009 | Evans et al. |
| 7,666,220 B2 | 2/2010 | Evans et al. |
| 7,682,383 B2 | 3/2010 | Robin |

(56) References Cited

U.S. PATENT DOCUMENTS

| | | |
|---|---|---|
| 7,708,773 B2 | 5/2010 | Pinchuk et al. |
| 7,790,273 B2 | 9/2010 | Lee et al. |
| 7,828,838 B2 | 11/2010 | Bolduc et al. |
| 7,872,068 B2 | 1/2011 | Khosravi et al. |
| 7,951,448 B2 | 5/2011 | Lee et al. |
| 8,044,137 B2 | 10/2011 | Khosravi et al. |
| 8,048,145 B2 | 11/2011 | Evans et al. |
| 8,182,525 B2 | 5/2012 | Herbowy et al. |
| 2001/0020184 A1 | 9/2001 | Dehdashtian et al. |
| 2001/0027337 A1 | 10/2001 | Di Caprio |
| 2001/0027338 A1 | 10/2001 | Greenberg |
| 2001/0044655 A1 | 11/2001 | Patnaik et al. |
| 2002/0019665 A1 | 2/2002 | Dehdashtian et al. |
| 2002/0026217 A1 | 2/2002 | Baker et al. |
| 2002/0045848 A1 | 4/2002 | Jaafar et al. |
| 2002/0045931 A1 | 4/2002 | Sogard et al. |
| 2002/0052643 A1 | 5/2002 | Wholey et al. |
| 2002/0077594 A1 | 6/2002 | Chien et al. |
| 2002/0151953 A1 | 10/2002 | Chobotov |
| 2002/0151956 A1 | 10/2002 | Chobotov |
| 2002/0151958 A1 | 10/2002 | Chuter |
| 2002/0156518 A1 | 10/2002 | Tehrani |
| 2002/0165521 A1 | 11/2002 | Cioanta et al. |
| 2002/0169497 A1 | 11/2002 | Wholey et al. |
| 2002/0183629 A1 | 12/2002 | Fitz |
| 2003/0004560 A1 | 1/2003 | Chobotov |
| 2003/0009132 A1 | 1/2003 | Schwartz et al. |
| 2003/0014075 A1 | 1/2003 | Rosenbluth et al. |
| 2003/0028209 A1 | 2/2003 | Teoh et al. |
| 2003/0036745 A1 | 2/2003 | Khosravi et al. |
| 2003/0051735 A1 | 3/2003 | Pavcnik et al. |
| 2003/0074056 A1 | 4/2003 | Killion et al. |
| 2003/0078647 A1 | 4/2003 | Vallana et al. |
| 2003/0093145 A1 | 5/2003 | Lawrence-Brown et al. |
| 2003/0130720 A1 | 7/2003 | DePalma et al. |
| 2003/0130721 A1 | 7/2003 | DePalma et al. |
| 2003/0135269 A1 | 7/2003 | Swanstrom |
| 2003/0204242 A1 | 10/2003 | Zarins et al. |
| 2003/0204249 A1 | 10/2003 | Letort |
| 2003/0216802 A1 | 11/2003 | Chobotov et al. |
| 2003/0225446 A1 | 12/2003 | Hartley |
| 2004/0016997 A1 | 1/2004 | Ushio |
| 2004/0044358 A1 | 3/2004 | Khosravi et al. |
| 2004/0082989 A1 | 4/2004 | Cook et al. |
| 2004/0091543 A1 | 5/2004 | Bell et al. |
| 2004/0098096 A1 | 5/2004 | Eton |
| 2004/0116997 A1 | 6/2004 | Taylor et al. |
| 2004/0147811 A1 | 7/2004 | Diederich et al. |
| 2004/0153025 A1 | 8/2004 | Seifert et al. |
| 2004/0167607 A1 | 8/2004 | Frantzen |
| 2004/0193245 A1 | 9/2004 | Deem et al. |
| 2004/0204755 A1 | 10/2004 | Robin |
| 2004/0215172 A1 | 10/2004 | Chu et al. |
| 2004/0215316 A1 | 10/2004 | Smalling |
| 2004/0220522 A1 | 11/2004 | Briscoe et al. |
| 2004/0243057 A1 | 12/2004 | Vinten-Johansen et al. |
| 2005/0004660 A1 | 1/2005 | Rosenbluth et al. |
| 2005/0027238 A1 | 2/2005 | Fago et al. |
| 2005/0028484 A1 | 2/2005 | Littlewood |
| 2005/0065592 A1 | 3/2005 | Holzer |
| 2005/0090804 A1 | 4/2005 | Chobotov et al. |
| 2005/0096731 A1 | 5/2005 | Looi et al. |
| 2005/0215989 A1 | 9/2005 | Abboud et al. |
| 2005/0245891 A1 | 11/2005 | McCormick et al. |
| 2005/0251251 A1 | 11/2005 | Cribier |
| 2006/0015173 A1 | 1/2006 | Clifford et al. |
| 2006/0025853 A1 | 2/2006 | Evans et al. |
| 2006/0074481 A1 | 4/2006 | Vardi et al. |
| 2006/0135942 A1 | 6/2006 | Fernandes et al. |
| 2006/0142836 A1 | 6/2006 | Hartley et al. |
| 2006/0155369 A1 | 7/2006 | Edwin et al. |
| 2006/0161244 A1 | 7/2006 | Seguin |
| 2006/0184109 A1 | 8/2006 | Gobel |
| 2006/0206197 A1 | 9/2006 | Morsi |
| 2006/0222596 A1 | 10/2006 | Askari et al. |
| 2006/0265043 A1 | 11/2006 | Mandrusov et al. |
| 2006/0292206 A1 | 12/2006 | Kim et al. |
| 2007/0032850 A1 | 2/2007 | Ruiz et al. |
| 2007/0043420 A1 | 2/2007 | Lostetter |
| 2007/0050008 A1 | 3/2007 | Kim et al. |
| 2007/0055355 A1 | 3/2007 | Kim et al. |
| 2007/0061005 A1 | 3/2007 | Kim et al. |
| 2007/0150041 A1 | 6/2007 | Evans et al. |
| 2007/0162109 A1 | 7/2007 | Davila et al. |
| 2007/0208416 A1 | 9/2007 | Burpee et al. |
| 2007/0276477 A1 | 11/2007 | Lee et al. |
| 2008/0039923 A1 | 2/2008 | Taylor et al. |
| 2008/0154368 A1 | 6/2008 | Justis et al. |
| 2008/0228259 A1 | 9/2008 | Chu |
| 2008/0294237 A1 | 11/2008 | Chu |
| 2009/0099649 A1 | 4/2009 | Chobotov et al. |
| 2009/0209855 A1 | 8/2009 | Drilling et al. |
| 2009/0216125 A1 | 8/2009 | Lenker |
| 2009/0318949 A1 | 12/2009 | Ganpath et al. |
| 2009/0319029 A1 | 12/2009 | Evans et al. |
| 2010/0004728 A1 | 1/2010 | Rao et al. |
| 2010/0036360 A1 | 2/2010 | Herbowy et al. |
| 2010/0106087 A1 | 4/2010 | Evans et al. |
| 2010/0217383 A1 | 8/2010 | Leonhardt et al. |
| 2012/0016456 A1 | 1/2012 | Herbowy et al. |
| 2012/0046684 A1 | 2/2012 | Evans et al. |

FOREIGN PATENT DOCUMENTS

| | | |
|---|---|---|
| EP | 1325717 A2 | 7/2003 |
| EP | 1903985 | 4/2008 |
| FR | 2834199 A1 | 7/2003 |
| JP | H04-322665 A | 11/1992 |
| JP | 2003-525692 A | 9/2003 |
| JP | 2004-537353 A | 12/2004 |
| JP | 2005-505380 A | 2/2005 |
| JP | 2005-532120 A | 10/2005 |
| JP | 2008-510502 A | 4/2008 |
| WO | 97/17912 A1 | 5/1997 |
| WO | 97/16553 A1 | 6/1997 |
| WO | 98/53761 A1 | 12/1998 |
| WO | 99/00073 A1 | 1/1999 |
| WO | 99/44539 A2 | 9/1999 |
| WO | 00/29060 A2 | 5/2000 |
| WO | 00/51522 A1 | 9/2000 |
| WO | 01/21108 A1 | 3/2001 |
| WO | 01/66038 A2 | 9/2001 |
| WO | 02/078569 A2 | 10/2002 |
| WO | 02/083038 A2 | 10/2002 |
| WO | 02/102282 A1 | 12/2002 |
| WO | 03/007785 A2 | 1/2003 |
| WO | 03/032869 A1 | 4/2003 |
| WO | 03/037222 A2 | 5/2003 |
| WO | 03/053288 A1 | 7/2003 |
| WO | 2004/004603 A1 | 1/2004 |
| WO | 2004/026183 A2 | 4/2004 |
| WO | 2004/037116 A2 | 5/2004 |
| WO | 2004/045393 A2 | 6/2004 |
| WO | 2006/012567 A2 | 2/2006 |
| WO | 2006/116725 A2 | 11/2006 |
| WO | 2007/008600 A2 | 1/2007 |
| WO | 2007/142916 A2 | 12/2007 |

OTHER PUBLICATIONS

Donayre et al., "Fillable Endovascular Aneurysm Repair," Endovascular Today, pp. 64-66, Jan. 2009.
Gilling-Smith, "Stent Graft Migration After Endovascular Aneurysm Repair," presented at 25th International Charing Cross Symposium, Apr. 13, 2003 [Power Point Presentation and Transcript], 56 pages total.
Journal of Endovascular Therapy; Apr. 2000; pp. 111, 114, 132-140; vol. 7' No. 2; International Society of Endovascular Specialists; Phoenix, AZ.
Patrick W. Serruys and Michael JB Kutryk; Handbook of Coronary Stents, Second Edition; 1998; pp. 45, 55, 78, 103, 112, 132, 158, 174, 185, 190, 207, 215, 230, 239; Martin Dunitz; UK.

(56) References Cited

OTHER PUBLICATIONS

Shan-e-ali Haider et al. Sac behavior after aneurysm treatment with the Gore Excluder low-permeability aortic endoprosthesis: 12-month comparison to the original Excluder device. Journal of Vascular Surgery. vol. 44, No. 4. 694-700. Oct. 2006.
Susan M. Trocciola et al. The development of endotension is associated with increased transmission of pressure and serous components in porous expanded polytetrafluoroethylene stent-grafts: Characterization using a canine model. Journal of Vascular Surgery. Jan. 2006. p. 109-116.
William Tanski, Mark Fillinger. Outcomes of original and low-permeability Gore Excluder endoprosthesis for endovascular abdominal aortic aneurysm repair. Journal of Vascular Surgery. Feb. 2007. p. 243-249.
U.S. Appl. No. 60/855,889, filed Oct. 31, 2006; first named inventor: Steven L. Herbowy.
U.S. Appl. No. 61/052,059, filed May 9, 2008; first named inventor: Gwendolyn A. Watanabe.
Examination report of EP Application No. 06751879.5, dated Mar. 24, 2014. 5 pages.

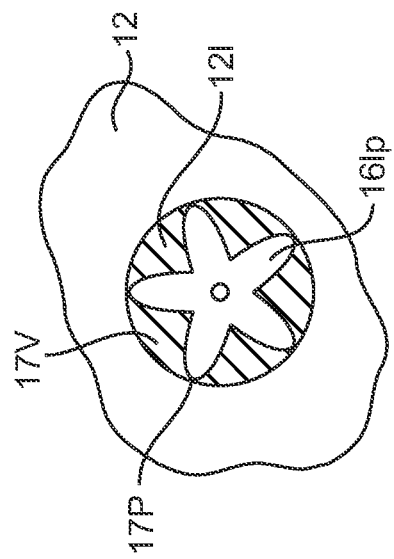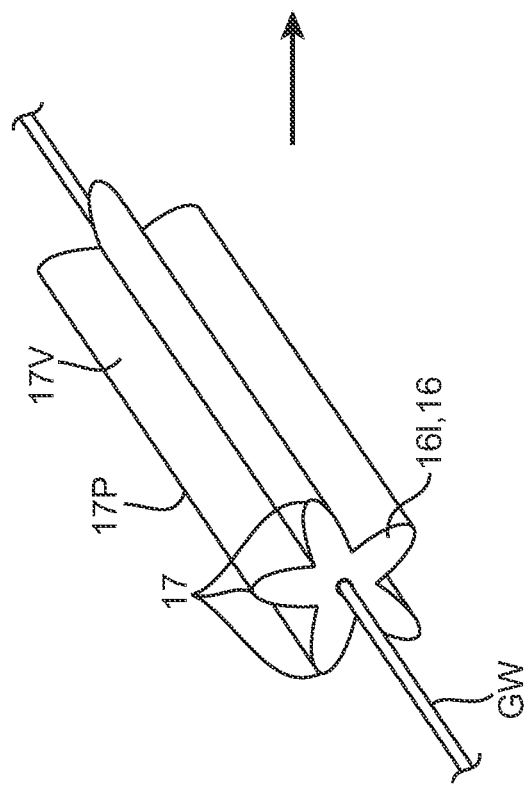
FIG. 11B
FIG. 11A

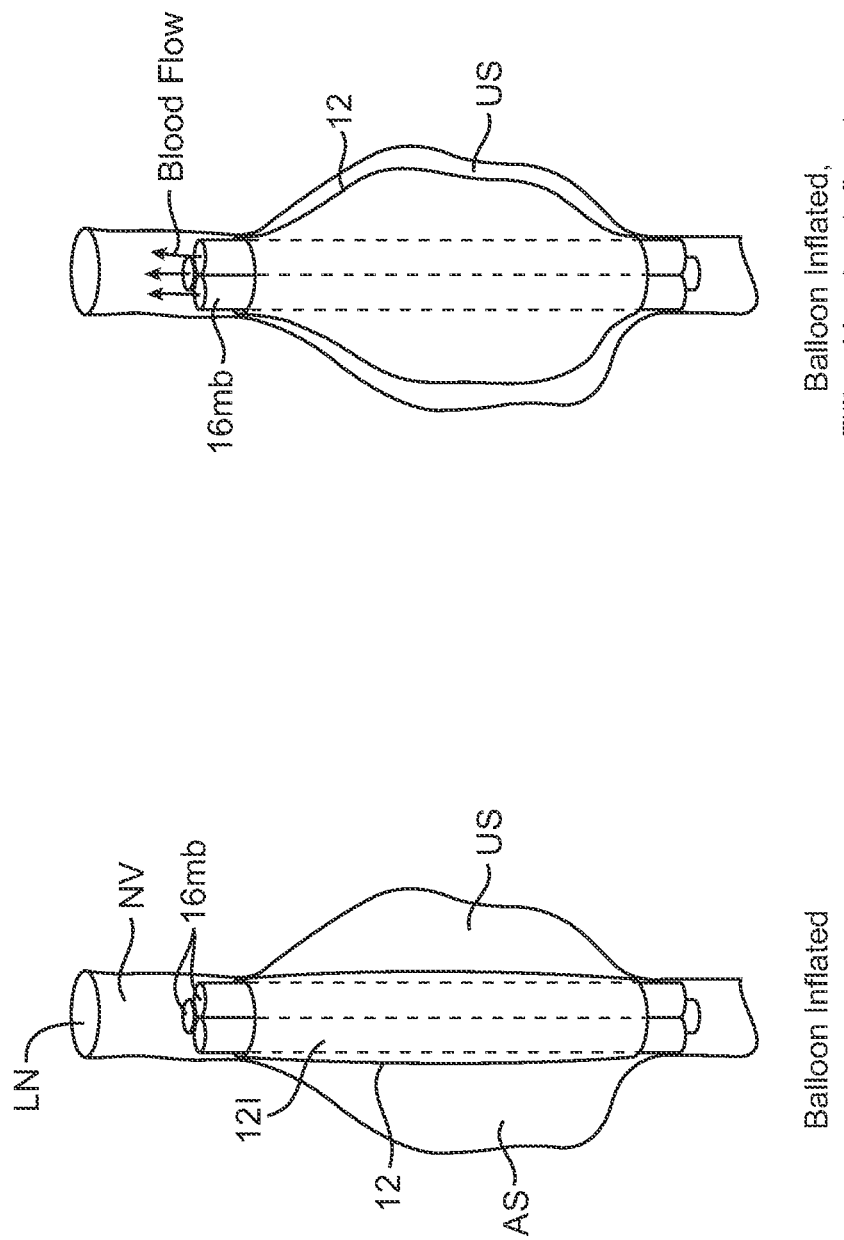
FIG. 13A  Balloon Inflated
FIG. 13B  Balloon Inflated, Filling Member Inflated

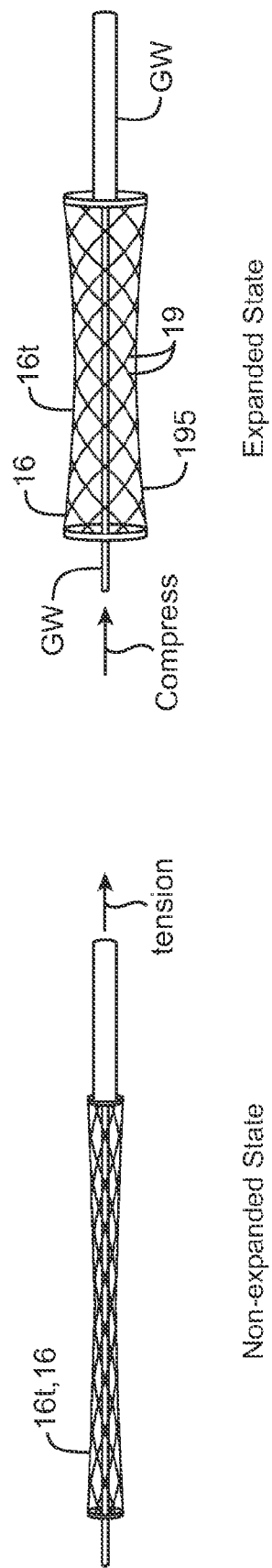

Non Deployed State

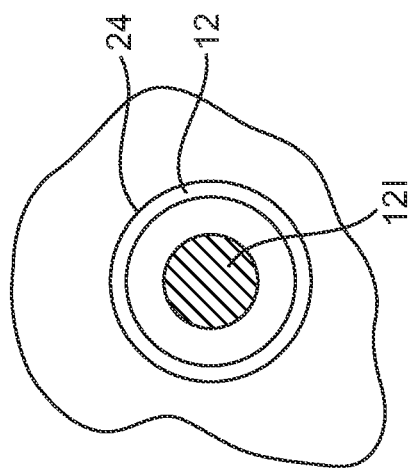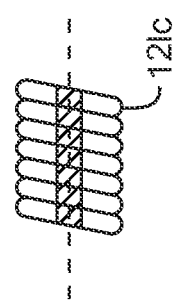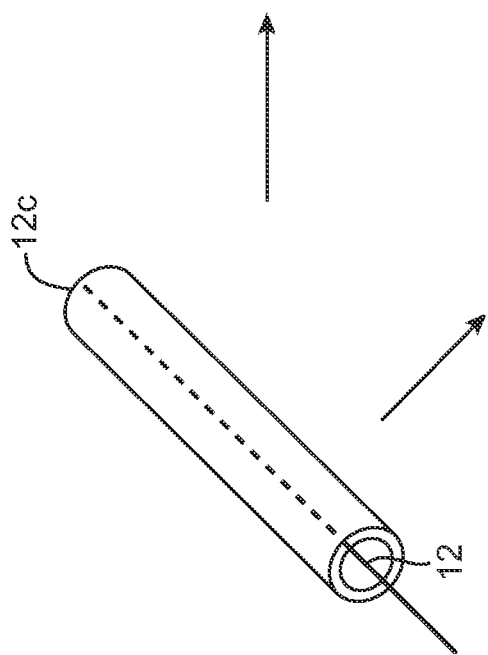
FIG. 17C
FIG. 17B
FIG. 17A

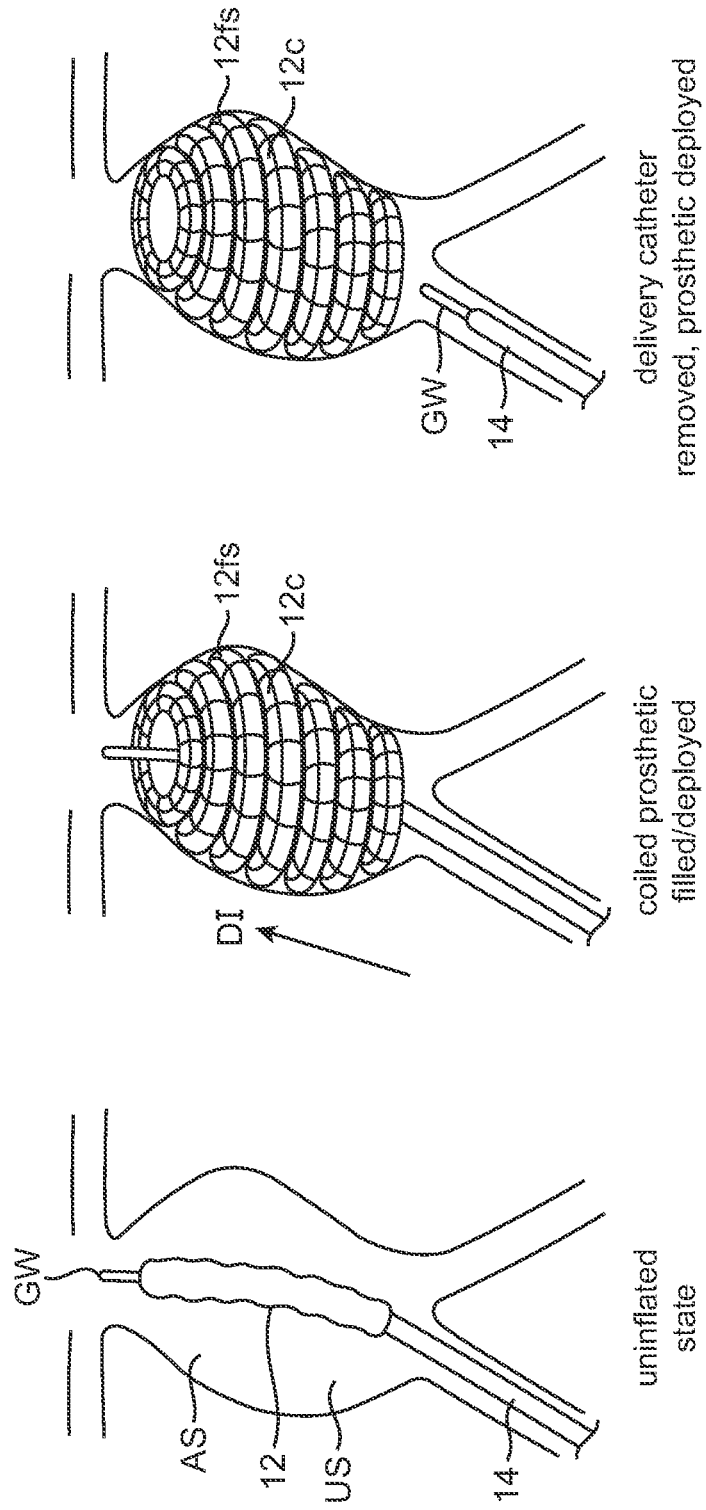

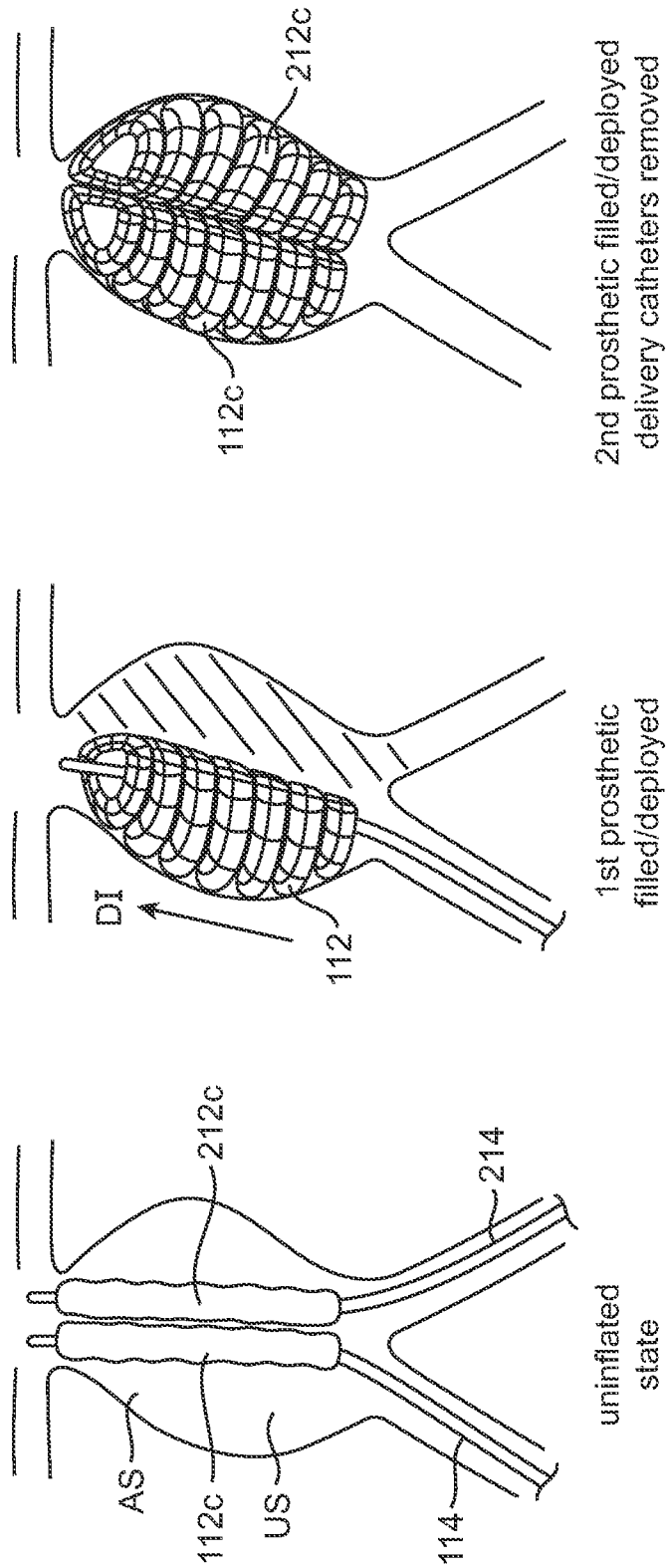

SYSTEM AND METHODS FOR ENDOVASCULAR ANEURYSM TREATMENT

CROSS-REFERENCES TO RELATED APPLICATIONS

The present application is a continuation of Ser. No. 12/684,074 filed Jul. 7, 2010, which is a divisional of U.S. patent application Ser. No. 11/482,503, filed on Jul. 7, 2006, which claims the benefit of priority of U.S. Provisional Application Ser. No. 60/696,818, filed on Jul. 7, 2005; and U.S. Provisional Application Ser. No. 60/696,817, filed on Jul. 7, 2005 the full disclosures of which are incorporated herein by reference.

The present application is also related to U.S. patent application Ser. No. 11/187,471, filed on Jul. 22, 2005, the full disclosure of which is incorporated herein by reference.

BACKGROUND OF THE INVENTION

Field of the Invention

Embodiments of the present invention relate generally to medical apparatuses and methods for treatment. More particularly, embodiments of the present invention relate to expandable prostheses and methods for treating abdominal and other aneurysms.

Aneurysms are enlargements or "bulges" in blood vessels which are often prone to rupture and which therefore present a serious risk to the patient. Aneurysms may occur in any blood vessel but are of particular concern when they occur in the cerebral vasculature or the patient's aorta.

Embodiments of the present invention are particularly concerned with aneurysms occurring in the aorta, particularly those referred to as aortic aneurysms. Abdominal aortic aneurysms (AAA's) are classified based on their location within the aorta as well as their shape and complexity. Aneurysms which are found below the renal arteries are referred to as infrarenal abdominal aortic aneurysms. Suprarenal abdominal aortic aneurysms occur above the renal arteries, while thoracic aortic aneurysms (TAA's) occur in the ascending, transverse, or descending part of the upper aorta.

Infrarenal aneurysms are the most common, representing about seventy percent (70%) of all aortic aneurysms. Suprarenal aneurysms are less common, representing about 20% of the aortic aneurysms. Thoracic aortic aneurysms are the least common and often the most difficult to treat. Most or all present endovascular systems are also too large (above 12 French) for percutaneous introduction.

The most common form of aneurysm is "fusiform," wherein the enlargement extends about the entire aortic circumference. Less commonly, the aneurysms may be characterized by a bulge on one side of the blood vessel attached at a narrow neck. Thoracic aortic aneurysms are often dissecting aneurysms caused by hemorrhagic separation in the aortic wall, usually within the medial layer. The most common treatment for each of these types and forms of aneurysm is open surgical repair. Open surgical repair is quite successful in patients who are otherwise reasonably healthy and free from significant co-morbidities. Such open surgical procedures are problematic, however, since access to the abdominal and thoracic aortas is difficult to obtain and because the aorta must be clamped off, placing significant strain on the patient's heart.

Over the past decade, endoluminal grafts have come into widespread use for the treatment of aortic aneurysm in patients who cannot undergo open surgical procedures. In general, endoluminal repairs access the aneurysm "endoluminally" through either or both iliac arteries in the groin. The grafts, which typically have fabric or membrane tubes supported and attached by various stent structures are then implanted, typically requiring several pieces or modules to be assembled in situ. Successful endoluminal procedures have a much shorter recovery period than open surgical procedures.

Present endoluminal aortic aneurysm repairs, however, suffer from a number of limitations. A significant number of endoluminal repair patients experience leakage at the proximal juncture (attachment point closest to the heart) within two years of the initial repair procedure. While such leaks can often be fixed by further endoluminal procedures, the need to have such follow-up treatments significantly increases cost and is certainly undesirable for the patient. A less common but more serious problem has been graft migration. In instances where the graft migrates or slips from its intended position, open surgical repair is required. This is a particular problem since the patients receiving the endoluminal grafts are those who are not considered good candidates for open surgery. Further shortcomings of the present endoluminal graft systems relate to both deployment and configuration. The multiple component systems require additional time for introducing each piece and even more time for assembling the pieces in situ. Such techniques are not only more time consuming, they are also more technically challenging, increasing the risk of failure. Current devices are also unsuitable for treating many geometrically complex aneurysms, particularly infrarenal aneurysms with little space between the renal arteries and the upper end of the aneurysm, referred to as short-neck or no-neck aneurysms. Aneurysms having torturous geometries are also difficult to treat.

For these reasons, it would desirable to provide improved methods, systems, and prostheses for the endoluminal treatment of aortic aneurysms. Such improved methods, systems, and treatments should preferably provide implanted prostheses which result in minimal or no endoleaks, resist migration, are relatively easy to deploy, have a low introduction profile (preferably below 12 French), and can treat most or all aneurysmal configurations, including short-neck and no-neck aneurysms as well as those with highly irregular and asymmetric geometries. At least some of these objectives will be met by the inventions described hereinafter.

Description of the Background Art

Grafts and endografts having fillable components are described in U.S. Pat. Nos. 4,641,653; 5,530,528; 5,665,117; and 5,769,882; U.S. Patent Publications 2004/0016997; and PCT Publications WO 00/51522 and WO 01/66038.

BRIEF SUMMARY OF THE INVENTION

Embodiments of the present invention provides methods, systems, and prostheses for the endoluminal treatment of aneurysms, particularly aortic aneurysms including both abdominal aortic aneurysms (AAA's) and thoracic aortic aneurysms (TAA's). A prosthesis can comprise double-walled filling structures which are pre-shaped and otherwise adapted to substantially fill the enlarged volume of an aneurysm, particularly a fusiform aneurysm, leaving a lumen in place for blood flow. Many embodiments utilize pressure monitoring at the aneurysm site to control the filling of the filling structure and determine endpoints for filling.

Embodiments of the double-walled filling structures will thus usually have a generally toroidal structure with an outer wall, an inner wall, a potential space or volume between the outer and inner walls to be filled with a filling medium, and a generally tubular lumen inside of the inner wall which provides the blood flow lumen after the prosthesis has been deployed. Other shapes are also contemplated. The shape of the filling structure will be preferably adapted to conform to the aneurysm being treated. In some instances, the filling structure can be shaped for the aneurysmal geometry of a particular patient using imaging and computer-aided design and fabrication techniques. In other instances, a family or collection of filling structures will be developed having different geometries and sizes so that a treating physician may select a specific filling structure to treat a particular patient based on the size and geometry of that patient's aneurysm. In all instances, the outer wall of the filling structure will conform or be conformable to the inner surface of the aneurysm being treated. The inner wall of the structure will be aligned with lumens of the blood vessels on either side of the prosthesis after the prosthesis has been deployed.

The filling structures of the prosthesis will usually be formed from a non-compliant material, such as parylene, Dacron, PET, PTFE, a compliant material, such as silicone, polyurethane, latex, or combinations thereof. Usually, it will be preferred to form at least the outer wall partially or entirely from a non-compliant material to enhance conformance of the outer wall to the inner surface of the aneurysm. This is particularly true when the aneurysm has been individually designed and/or sized for the patient being treated.

The walls of the filling structures may consist of a single layer or may comprise multiple layers which are laminated or otherwise formed together. Different layers may comprise different materials, including both compliant and/or non-compliant materials. The structure walls may also be reinforced in various ways, including braid reinforcement layers, filament reinforcement layers, and the like. In some instances, it would be possible to include self-expanding scaffolds within the filling structures so that the structures could be initially delivered and be allowed to self-expand at the treatment site, thus obviating the need for an expansion delivery catheter as described as the preferred embodiment below.

Preferred delivery protocols will utilize delivery catheters having a balloon or other expandable support for carrying the filling structure. When using balloons, the balloons will preferably be substantially or entirely compliant, although non-compliant and combination compliant/non-compliant balloons may also find use. The balloon or other mechanical expansion components of the delivery catheter will initially be disposed within the inner tubular lumen of the filling structure, with the filling structure generally being collapsed into a low width or low profile configuration over the expansion element. The delivery catheter may then be introduced intraluminally, typically into the iliac artery and upwardly to the region within the aorta to be treated. The delivery catheter will also include one or more lumens, tubes, or other components or structures for delivering the filling medium in a fluid form to an internal filling cavity of the filling structure. Thus, the delivery catheter can be used to both initially place and locate the filling structure of the prosthesis at the aneurysmal site. Once at the aneurysmal site, the internal tubular lumen of the structure can be expanded using the balloon or other expandable element on the delivery catheter. The filling structure itself will be filled and expanded by delivering the filling medium via the catheter into the internal volume of the filling structure. Both expansion and filling operations may be performed simultaneously, or can be performed in either order, i.e., the filling structure may be filled first with the delivery catheter balloon being expanded second, or vice versa. The filling structure(s) and/or delivery balloons may have radio-opaque markers to facilitate placement and/or pressure sensors for monitoring filling and inflation pressures during deployment.

In preferred embodiments of the invention, pressure monitoring can be performed at various stages of the aneurysm repair procedure to help control the filling process of the filling structure. The monitoring of pressures serves to reduce the risk of dissection or damage to the aneurysm from over-pressurization and also can be used to determine an endpoint for filling. Monitoring can be done before during or after filling and hardening of the filling structure with filling medium. Specific pressures which can be monitored include the pressure within the internal space of the filling structure as well as the pressure in the space between the external walls of the filling structure and the inner wall of the aneurysm. A composite measurement can also be made combining pressures such as those measured within the interior space of the filling structure, together with that measured in the space between the external walls of the structure and the aneurysm wall or other space at the aneurysm site and an external delivery pressure used by a fluid delivery device, such as a pump, to deliver the filling medium. Control decisions can be made using any one of these pressure or a combination thereof.

Pressures can be measured using a number of pressure sensing means known in the art including pressure sensors placed on the interior or exterior of the filling structure as well as a pressure monitoring catheter, guidewire or other pressure sensing member placed at the aneurysm site between the structure and the aneurysm wall. The pressure sensing means can in turn be coupled to a pressure monitoring means such as a gauge, electronic pressure monitor, computer or the like. A signal from the pressure sensor(s) can be inputted to a pressure monitoring and control device such as computer which can utilize the signal in algorithm to control the flow rate and pressure of a pump or other coupled the fluid delivery device used to deliver the filling medium. Pressures can be monitored so as to stay below a selected threshold pressure which may result in an increased likelihood of dissection of the aneurysm wall due to pressure forces exerted on the wall from the pressure exerted by the filling structure during filling. The threshold pressure can be determined based on the size and shape of the particular aneurysm, the patient blood pressure, the wall thickness of the aneurysm and other dimensional, mechanical and morphological characteristics of the aneurysm site. In particular embodiments the Law of Laplace can be employed to determine the forces which will be exerted on the arterial wall for a given filling pressure. The pressures can also be monitored to stay below a threshold rate or pressure increase.

In many embodiments, the monitored pressures can be used to control one or both of the flow rate and filling pressure of filling medium into the filling structure. Control can be effected manually using a syringe or automatically using a metered pump or other fluid delivery device which is coupled to a controlling computer or other control system. For example, flow rates can be decreased or stopped when the pressure or a rate of pressure increase reaches a threshold value either in the interior or exterior of the filling structure. Also pressure monitoring can be used to determine an endpoint for the delivery of the filling medium. An endpoint decision can be determined based on reaching a particular pressure value for the interior and/or exterior space of the filling structure. Endpoint can also be determined by combining a measured pressure(d) together with a delivered volume of medium, and imaging observations on the size and shape of the expanded filling structure. For example, an endpoint can be reached when a factorial value of pressure and volume has been reached. In this way, an endpoint decision can be made using a multi-parameter analysis to provide a more comprehensive determination for knowing on the one hand when the filling structure is adequately filled and on other assuring that it is not over-pressurized. Also in related embodiments, pressure monitoring can be used to titrate the total delivery of medium into the filling structure.

In preferred aspects of the present invention, the filling structure will be filled with a fluid (prior to hardening as described herein below) at a pressure which is lower than that of the expansion force provided by the delivery catheter, typically the filling pressure of the expandable balloon. Typically, the filling structure will be filled with filling medium at a pressure from 80 mm of Hg to 1000 mm of Hg, preferably from 200 mm of Hg to 600 mm of Hg, while the delivery balloon is inflated to a pressure in the range from 100 mm of Hg to 5000 mm of Hg, preferably from 400 mm of Hg to 1000 mm of Hg. These pressures are gage pressures, i.e., pressures measured relative to atmospheric pressure. As is descried herein in many embodiments, the pressure within or external the double-walled structure will be monitored and compared to a maximum or other value of the patient's blood pressure. In such cases, the filling pressure can be titrated so as to stay below a threshold pressure relative to the patient's blood pressure, for example 90%, 100%, 110%, 150%, 200%, 250 or 300% of the patient's maximum blood pressure (or other pressure value). In this way, real time pressure monitoring can be used to reduce the likelihood of vessel dissection caused by over-pressurization of the aneurysm from the pressure exerted by the filling structure during filling.

As described thus far, embodiments of the invention contemplate delivery of a single prosthesis and filling structure to an aneurysm. Delivery of a single filling structure will be particularly suitable for aneurysms which are remote from a vessel bifurcation so that both ends of the filling structure are in communication with only a single blood vessel lumen. In the case of aneurysms located adjacent a vessel bifurcation, such as infrarenal abdominal aortic aneurysms, it will often be preferable to utilize two such filling structures introduced in a generally adjacent, parallel fashion within the aneurysmal volume. In the specific case of the infrarenal aneurysms, each prosthesis will usually be delivered separately, one through each of the two iliac arteries. After locating the filling structures of the prosthesis within the aneurysmal space, they can be filled simultaneously or sequentially to fill and occupy the entire aneurysmal volume, leaving a pair of blood flow lumens. Pressure monitoring can be done before, during or after the filling of one or both filling structures. Threshold pressure can also be adjusted accordingly (e.g., up or down) for the use of two filling structures. Also, adjustments can be made for the effect of filling one filling structure on the measured pressure in the interior space of the other.

Suitable materials for the fluid filling medium (also described herein as filling material) will be fluid initially to permit delivery through the delivery catheter and will be curable or otherwise hardenable so that, once in place, the filling structure can be given a final shape which will remain after the delivery catheter is removed. The fillable materials will usually be curable polymers which, after curing, will have a fixed shape with a shore hardness typically in the range from 10 durometer to 140 durometer. The polymers may be delivered as liquids, gels, foams, slurries, or the like. In some instances, the polymers may be epoxies or other curable two-part systems. In other instances, the polymer may comprise a single material which when exposed to the vascular environment within the filling structure changes state over time, typically from zero to ten minutes. In still other instances, the filling medium need not be hardenable/curable but may remain liquid and can have rheological properties configured to mimic blood or native tissue. Such mediums can include various silicone and collagen solutions known in the art.

In a preferred aspect of the present invention, after curing, the filling material will have a specific gravity, typically in the range from 0.1 to 5, more typically from 0.8 to 1.2 which is generally the same as blood or thrombus. The filling material may also include bulking and other agents to modify density, viscosity, mechanical characteristics or the like, including microspheres, fibers, powders, gasses, radiopaque materials, drugs, and the like. Exemplary filling materials include polyurethanes, collagen, polyethylene glycols, microspheres, and the like.

Preferably, the filling structures of the prosthesis will require no additional sealing or anchoring means for holding them in place within the aneurysm. In some instances, however, it may be desirable to employ such additional sealing or anchoring mechanisms, such as stents, scaffolds, hooks, barbs, sealing cuffs, and the like. For sealing cuffs or stents which extend proximately of infrarenal prosthesis, it may be desirable to provide openings or ports to allow the anchoring or sealing devices to extend over the renal ostia while penetrating blood flow into the renal arteries. The sealing or anchoring devices will typically be attached to and/or overlap with the filling structure of the prosthesis and will provide for a smooth transition from the aortic and/or iliac lumens into the tubular lumens provided by the deployed filling structures.

The filling structures may be modified in a variety of other ways within the scope of the present invention. For example, the external surfaces of the filling structures may be partially or entirely modified to enhance placement within the aneurysmal space, typically by promoting tissue ingrowth or mechanically interlocking with the inner surface of the aneurysm. Such surface modifications include surface roughening, surface stippling, surface flocking, fibers disposed over the surface, foam layers disposed over the surface, rings, and the like. It is also possible to provide biologically active substances over all or a portion of the external surface of the filling structure, such as thrombogenic substances, tissue growth promotants, biological adhesives, and the like. It would further be possible to provide synthetic adhesives, such as polyacrylamides, over the surface to enhance adherence. Also the surface of the structure can be coated with one or more antibiotics to reduce the risk of post-implant infection.

In some instances, it will be desirable to modify all or a portion of the internal surface of the filling cavity of the filling structure. Such surface modifications may comprise surface roughening, rings, stipples, flocking, foam layers, fibers, adhesives, and the like. The purpose of such surface modification will usually be to enhance the filling and bonding to the filling material, and to control the minimum wall thickness when the structure is filled particularly after the filling material has been cured. In particular instances, in locations of the filling structure which will be pressed together when the structure is deployed, thus potentially excluding filling material, it will be desirable if the surfaces of the filling structure can adhere directly to each other.

In view of the above general descriptions of the present invention, the following specific embodiments may be better understood. In a first specific embodiment, methods for treating an aneurysm comprise positioning at least one double-walled filling structure across the aneurysm. By "across" the aneurysms, it is meant generally that the filling structure will extend axially from one anatomical location, which has been identified by imaging or otherwise as the beginning of the aneurysm to a space-part location (or locations in the case of bifurcated aneurysm) where it has been established that the aneurysm ends. After positioning, the at least one filling structure is filled with a fluid filling medium so that an outer wall of the structure conforms to the inside of the aneurysm and an inner wall of the structure forms a generally tubular lumen to provide for blood flow after the filling structure has been deployed. The tubular lumen will preferably be supported by a support structure, typically a balloon or mechanically expansible element, while the filling structure is being filled, after the filling structure has been filled, or during both periods. The pressure exerted by the medium within or external the filling structure can be monitored using a pressure sensing means such as a pressure sensor positioned on the interior or exterior of the filling structure. The pressure sensors can include various solid state and MEMS-based sensors known in the art and can be configured to provide pressure monitoring both during and after the filling procedure. The pressure sensing means can also comprise a pressure monitoring catheter, guidewire or other pressure sensing member positioned at the aneurysm site between the filling structure and the aneurysm wall. The pressure sensing member is desirably configured to be advanceble to the aneurysm site from the point of arterial or venous access. It can have a pressure sensing lumen for fluid communication with a pressures sensing device, or it can have one or more pressure sensors positioned at it distal tip. The pressure sensing member can be configured to also be advanced into the interior of the filling structure from a lumen in the delivery catheter. In particular embodiments, two or more pressure sensing members can be used and positioned at different locations in or around the aneurysm site to provide for differential pressure measurements.

The monitored pressure(s) can be used to control the flow rate of filling medium into filling structure and the filling pressure exerted by a syringe pump or other fluid delivery device. It can be also used to determine an endpoint for filling of the filling structure. Filling can be stopped or deceased when the monitored pressure exceeds a particular threshold. The threshold can be established by comparison to a measurement of the patient's blood pressure such as their maximum systolic pressure. For example, filling can be slowed or stopped when a monitored pressure is in the range of 100 to 140% of the maximum blood pressure with a specific embodiment of 110%. Also, similar to pressure monitoring, the volume of delivered filling medium can be monitored and used to control the filling medium flow rate as well as endpoint either independently or in combination with pressure measurement.

In various embodiments, filling can also be controlled by means of a valve coupled to the filling structure either directly or to a filling tube coupled to filling structure. In one embodiment, the valve can be configured as a mechanical pressure relief valve to open and relieve pressure from an interior of the structure when a threshold pressure has been reached. In another embodiment the valve can be an electronically controlled valve which either opens to relieve pressure within the filling structure when the threshold pressure is reached or closes to prevent the influx of additional filling medium. In the former case, the valve can be coupled to an exterior wall of the filling structure and in the latter case it can be coupled to a filling tube or other filling member used to fill the filling structure. The valve can be controlled responsive to a pressure signal directly or indirectly from the pressure sensing means, such as an electronic signal from a solid state pressure sensor.

After the filling structure has been filled, the filling material or medium is hardened while the tubular lumen remains supported so as to make a formed tubular lumen. Supporting the tubular lumen during hardening assures that the formed lumen will have a desired geometry, will properly align with adjacent vascular lumens, and that the tubular lumen being formed remains aligned with the native aortic and/or iliac artery lumens after the prosthesis has been fully implanted. Preferably, the support will be provided by a balloon which extends proximally (upstream) and distally (downstream) out of the filling structure where the balloon may slightly "over-expand" in order to assure the desired smooth transition and conformance of the tubular lumen provided by the filling structure with the native vessel lumens. In particular embodiments, the balloon can have a dog bone or similar shape such that the proximal and distal portions of the balloon are flared outwards or otherwise have a larger diameter than the central portion of the balloon. The ends of the inflated balloon extend at least partially out of the filling structure. This configuration serves to shape the lumen of the cured filling structure such that the proximal and distal ends of the formed lumen flare out relative to the central portion. This shape serves to provide a smooth transition in diameter from the native vessel to the formed lumen and in particular minimizes the surface of the area of the formed lumen that is normal to the direction of blood flow through artery. This later configuration serves to minimize an amount of sheer stress on the formed and adjacent native lumens as well as reduce an amount of retrograde flow and turbulence in vessel regions within and adjacent the prosthesis. These fluid dynamic factors serve to reduce the likelihood of the formation of stenosis in the region of the prosthetic.

After hardening, the support will be removed, leaving the filling structure in place. In some cases, a drain device will be left in place at the aneurysm site external to the filling structure to provide for the post implant draining of blood or other fluids located in the space between the aneurysm wall and the filled filling structure as discussed below. A porous portion of the device can be attached to an external surface of the filling structure to serve as a fluid inlet and another portion such as a drain tube may be positioned within the new or native arterial lumen to serve as a fluid outlet. Desirably, the tube portion only slightly extends into the native lumen and is positioned closely to the lumen wall to minimize contact areas with flowing blood. The tube portion can also be configured to be detachable by means of a guidewire, catheter or other minimally invasive method. This allows the physician to remove the tube portion at a selected time period post implant (e.g., two weeks) at which time it is no longer needed. The porous portion can include a plurality of apertures, can be wrapped helically or otherwise around the perimeter of the filling structure to provide for multiple points of fluid entry. Desirably the drain device is constructed from non-thrombogenic biomaterials such as expanded PTFE so as to maintain patentcy of the drain. It can also be constructed from re-absorbable biomaterials known in the art which provide a drain function for a selected time period before being reabsorbed by the body. In some instances, however, prior to hardening, it will be desirable to confirm proper placement of the filling structure. This can be done using imaging techniques or otherwise testing for patency and continuity.

In some cases, it may be desirable to first fill the filling structure with saline or other non-hardenable substance to make sure that the geometry and size of the filling structure are appropriate for the particular aneurysm. The fit of the filling structure within the aneurysm can be checked by imaging methods and the volume of saline can be adjusted accordingly to produce a desired fit. For example the physician can check to see if the filling structure has filled in the entire aneurysm space or if there any gaps remaining. This can be facilitated by the use of contrast agents added to the saline or other non-hardenable filling solution. The volume of saline or other fluid which produces the desired fit can then be noted. After testing, the saline may be removed and replaced with an equal or substantially equal volume of hardenable filler and the remainder of the procedure followed as described above and herein. In use, these and related embodiments provide the physician with a means for improving and assuring the fit of the prosthesis at the aneurysm site before committing to the procedure. This results in improved clinical outcomes and reduced incidence of morbidity and mortality due to an improperly fit prosthesis.

Various embodiments of the invention also provide means and methods for draining of blood (and other fluids) located between the exterior walls of the filling structure and the inner walls of the aneurysm. Such methods reduce the pressure exerted on the aneurysms walls during the filling procedure and provide for the draining of blood or other fluids which remain after the completion of the procedure. Several different approaches may be employed. In one approach, the support balloon or other mechanical support member are shaped so as to not form a seal with the artery wall (when expanded) and thus allow blood to flow around the balloon/expansion device at desirably both the proximal and distal ends of the device. This allows any blood located between the filling device and aneurysm wall to readily flow out or be squeegeed out from the aneurysms site as the filling structure is expanded. In specific embodiments the balloon can have a multi-lobed cross sectional profile which allows blood to flow in the valleys between the lobes while peaks of the lobes provide support to maintain the tubular shape of the inner lumen of the filling member. In one embodiment, the balloon can have a three lobe structure. In other embodiments, the balloon support member can comprise a multi-balloon member, for example, a three balloon member that allows for blood flow in the spaces between the balloons. In other embodiments, an expandable shape memory stent can be used that allows for blood flow through the stent. In another, expandable basket-like structures can be used. The expandable basket-like structures have a series of spring memory splines or other spring member to hold the lumen open, but still allows blood flow around and through the splines. The stent or basket can have a deployed and non-deployed state. The stent or basket can be deployed either through the application of tension or compression which can be applied, for example, by the delivery catheter or guide wire. Other structures having spring memory materials which can be mechanically engaged to a deployed state to support the inner lumen can also be used. These and related embodiments not only provide for the outflow of blood located between the aneurysm wall and the filling structure but also for the normal flow of blood through the entire length of the aneurysm site so as to maintain adequate perfusion of organs and tissue downstream from the aneurysm site. Such perfusion can also be achieved or supplemented by the use of a perfusion lumen and proximal and distal apertures in the delivery catheter which allows blood to flow through the delivery catheter when the balloon is inflated during filling of the filling structure. In other embodiments allowing perfusion, the filling structure can comprise a continuously coiled structure that has an open central lumen for blood flow which does not need support during filling, or a series of inner tube like structures that are joined and also do not need to be supported during filling to maintain patentcy of the central lumen.

In another approach for draining blood from the aneurysm site, a drain device can be positioned on or nearby the exterior outer wall of the filling structure. The drain can be configured to be removed after the completion of the filling procedure or left in place to provide for post implant draining of the aneurysm site as is discussed below. The drain will typically have a porous inflow portion and a tube outflow portion. The porous portion allows for the inflow of blood from an aneurysm site. The tube portion extends downstream or upstream from aneurysm site into the native vessel lumen and provides for the outflow of blood. The tube portion can be configured to extend a selectable length into the native lumen. Preferably for post implant draining, the tube portion is configured to only slightly extend into the lumen of the native vessel and is configured to be located close to the lumen wall (e.g., several millimeters) to minimize contact area with flowing blood. It can be coupled to a catheter as discussed below.

The porous portion can include a plurality of apertures which allows for the inflow of blood from multiple locations and also provides redundancy should one or more of the apertures become blocked with thrombus or other matter. The porous portion can be helically or otherwise wrapped around all or a portion of the perimeter of the filling structure exterior. Helically wrapping allows for the inflow of blood from multiple locations around the filling structure and thus serves to produce more uniform draining of blood or other fluid. In particular embodiments, the porous portion can also comprise a plurality of arms which are longitudinally or otherwise distributed around the perimeter of the filling structure. The porous portion can be attached to the filling structure with an adhesive or sonic weld or held in place by tension.

In many embodiments, the drain device is configured to provide a passive draining function based from the pressure exerted by blood or other fluid constrained between the filling structure and the inner walls of the filling aneurysm. In other embodiments, the drain can be configured to be coupled to a vacuum so as to provide active draining by a vacuum force. Vacuum application to remove blood can be done at any selected time during the repair procedure, including during or after filling of the filling structure. In some embodiments, blood can be withdrawn concurrently to the injection of filling medium into the filling structure so as to control the pressure exerted by the filling medium on the aneurysm wall. In particular embodiments, a substantially equal volume of blood can be withdrawn from the aneurysm site as the volume of medium is injected into the filling structure. The withdrawal and injection can be done simultaneously or near simultaneously and substantially at the same rate using concurrent injection and withdrawal means known in the art. Pressures can be monitored continuously during this operation and the withdrawal rate and/or injection rate can be adjusted accordingly to maintain pressure below a threshold or other set point.

Vacuum application can be achieved by coupling the tube or end portion of the drain to a dedicated lumen of the delivery catheter which is in turn connected to a vacuum source. Alternatively, the drain device can be attached to a separate catheter for providing a dedicated source of vacuum pressure. This latter configuration also provides a means for placement and removal of the drain device independent from positioning of the delivery catheter.

In still other approaches, a drain function can be provided by means of a needle which is inserted into the aneurysm site by a laparoscopic approach or other method. A vacuum can then be pulled on the needle using a syringe or other vacuum source. In a related approach, draining can be done using a pressure sensing member such as catheter or guide wire discussed herein which is appropriately positioned in the aneurysm site. The pressure sensing member can provide for both passive draining or active draining through the application of vacuum pressure to the pressure monitoring lumen of the catheter or guide wire. The lumen dimension can be sized to provide for both pressure monitoring and blood/fluid removal functions. The pressure sensing member can also be used to supplement the draining function of a primary draining device as well as reach particular locations between the aneurysm wall and filling structure that require additional draining or are otherwise inaccessible to the primary drain device. This function can be achieved by configuring the pressure sensing member to be steerable using various catheter/guidewire fabrication techniques known in the art.

In a second specific embodiment of the present invention, abdominal aortic aneurysms and other bifurcated aneurysms are treated by positioning first and second double-walled filling structures within the aneurysmal volume. The first and second double-walled filling structures are positioned across the aneurysm, as defined above, extending from the aorta beneath the renal arteries to each of the iliac arteries, respectively. The first fluid filling structure is filled with a fluid filling material, the second filling structure is also filled with a fluid material, and the outer walls of each filling structure will conform to the inside surface of the aneurysm as well as to each other, thus providing a pair of tubular lumens for blood flow from the aorta to each of the iliac arteries. Preferably, the tubular lumens of each of the first and second filling structures are supported while they are being filled or after they have been filled. Still further preferably, the tubular lumens will remain supported while the filling material is hardened, thus assuring that the transitions to the tubular lumens to the native vessel lumens remain properly aligned and conformed.

In a third specific embodiment of the present invention, systems for treating aneurysms comprise at least one double-walled filling structure and at least one delivery catheter having an expandable support positionable within a tubular lumen of the filling structure. The systems will usually further comprise a suitable hardenable or curable fluid filling medium. The particular characteristics of the filling structure and delivery balloon have been described above in connection with the methods of the present invention.

In a still further specific embodiment of the present invention, a system for treating abdominal aortic aneurysms comprises a first double-walled filling structure and a second double-walled filling structure. The first and second filling structures are adapted to be filled with a hardenable filling medium while they lie adjacent to each other within the aneurysm. The systems further comprise first and second delivery catheters which can be utilized for aligning each of the first and second filling structures properly with the right and left iliacs and the infrarenal aorta as they are being deployed, filled, and hardened.

BRIEF DESCRIPTION OF THE DRAWINGS

FIG. 9A shows a porous portion of a drain device positioned in vessel space US, FIG. 9B shows a drain device with a porous portion positioned in space US coupled to a vacuum source for active draining, FIG. 9C shows a drain device having a helically wrapped porous portion, FIG. 9D shows a drain device having a plurality of porous arms defining a drainage geometry, FIG. 9E is a detailed view of a single arm of the embodiment of FIG. 9 D, FIG. 9 F shows a embodiment of a drain device comprising a needle.

FIGS. 11A-B are lateral and cross sectional views illustrating embodiments of an inflatable multi-lobe support member that allows for the drainage of blood from the aneurysm site during inflation.

FIGS. 13A-B illustrate the use of an embodiment of a multi balloon support member to allow the drainage of blood from the aneurysm site during inflation FIG. 14A is a perspective view illustrating an embodiment of an expandable stent support member that allows for the drainage of blood from the aneurysm site during inflation in the non-expanded state.

FIG. 14B is a perspective view illustrating an embodiment of an expandable stent support member that allows for the drainage of blood from the aneurysm site during inflation in the expanded state.

FIGS. 17A-C are perspective, lateral and cross sectional views illustrating embodiments of a coiled filling structure that allows for the drainage of blood from the aneurysm site during filling.

FIGS. 20A-C illustrate use of a continuously coiled filling structure for repair of an arterial aneurysm.

FIGS. 21A-21C illustrate use of a pair or continuously coiled filling structures for repair of an arterial aneurysm near an arterial bifurcation.

DETAILED DESCRIPTION OF THE INVENTION

Figure 1A:
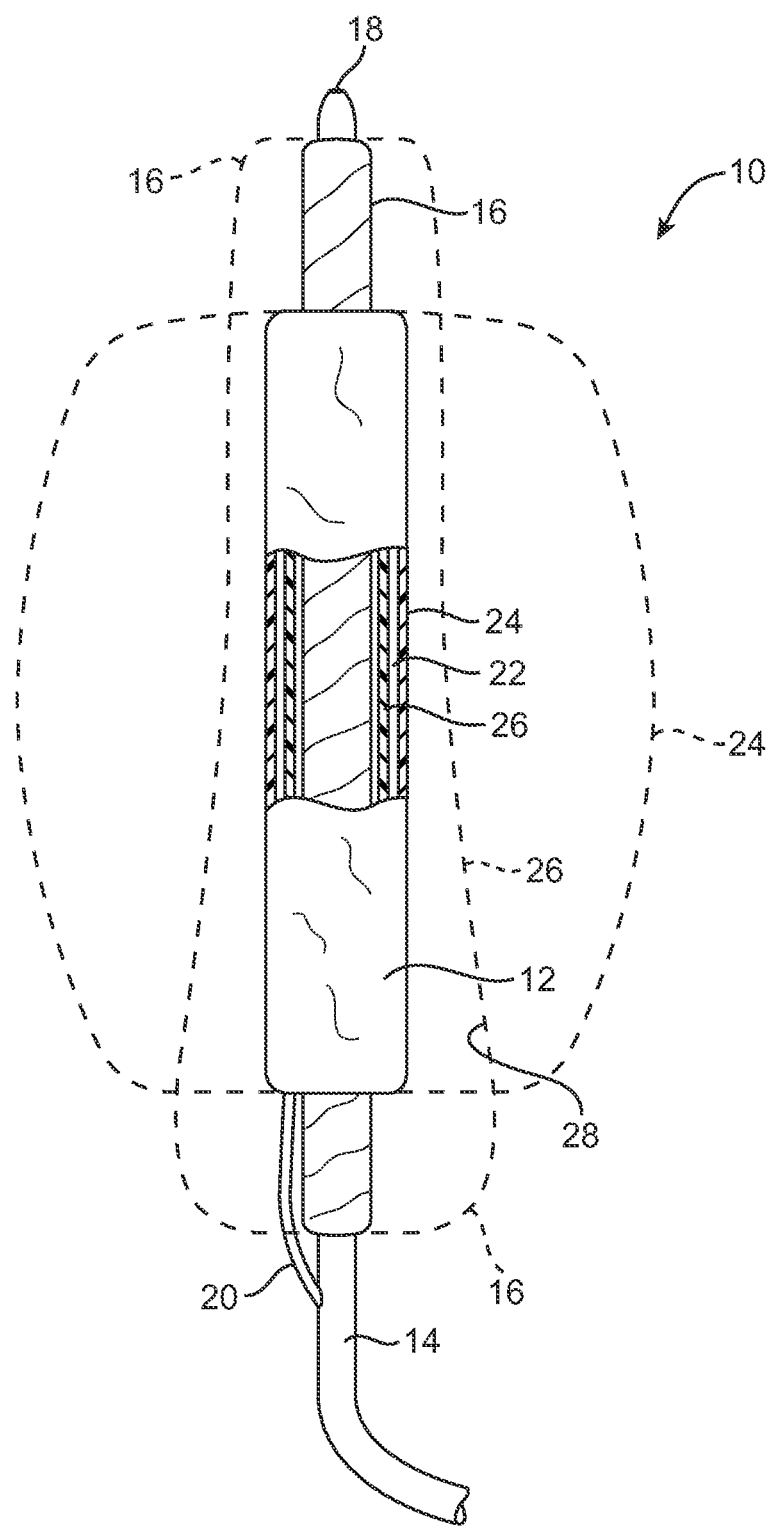
FIG. 1A illustrates a single prosthesis system comprising a filling structure mounted over a delivery catheter.
Figure 1B:
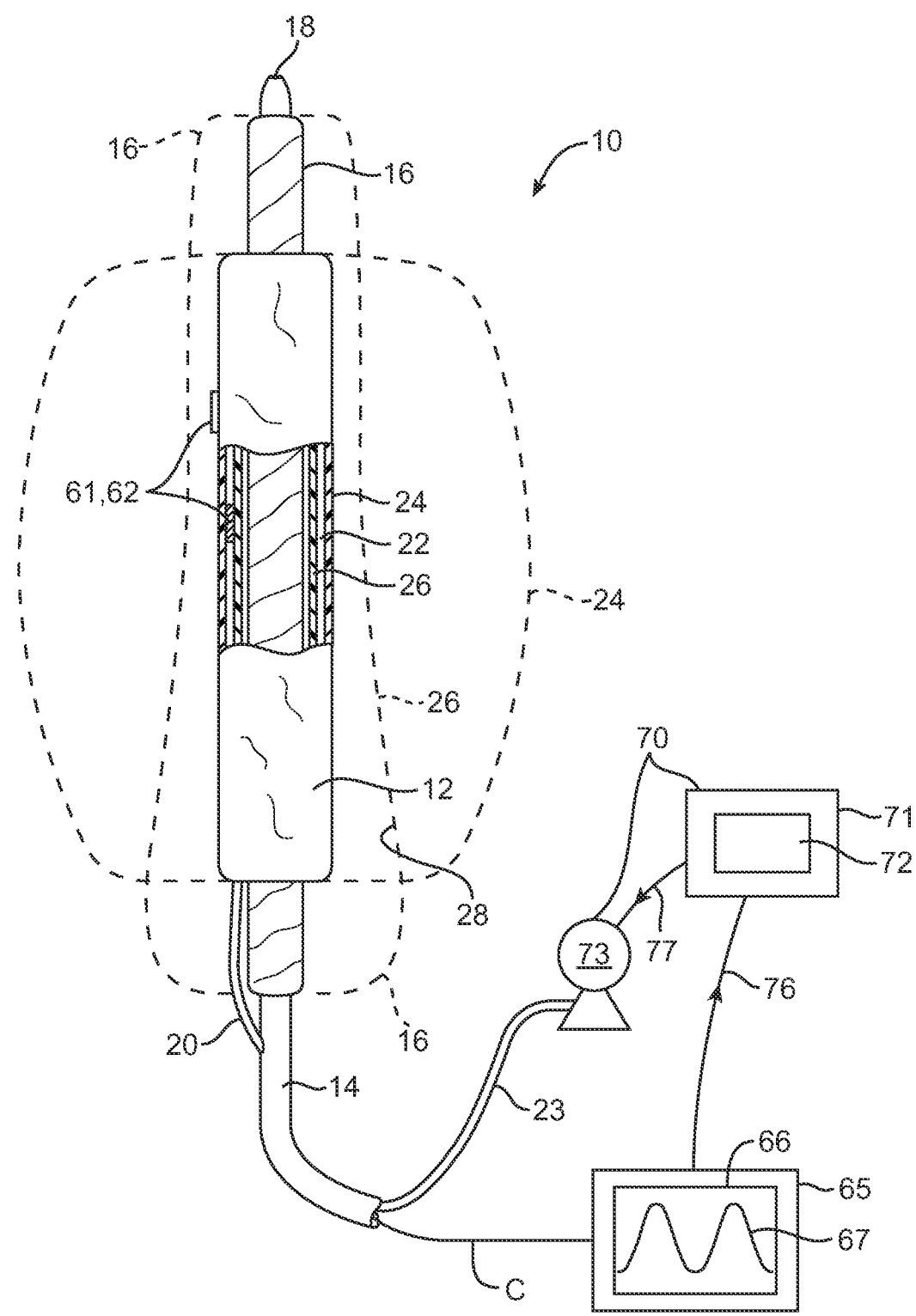
FIG. 1B illustrates a single prosthesis system including a pressure monitoring system for monitoring pressure during an aneurysm repair procedure using a fillable prosthetic implant.

Referring now to FIGS. 1A-1D, an embodiment of a system 10 constructed in accordance with the principles of the present invention for delivering a double-walled filling structure 12 to an aneurysm includes the filling structure and a delivery catheter 14 having a support structure 16, at its distal end. Typically, support structure 16 comprises an expandable element 16 such as expandable balloon. The support structure can also comprise various mechanically expandable structures, such mechanically expandable stents, basket devices and various mechanical structures having shape or spring memory. The catheter 14 will comprise a guidewire lumen 18, a balloon inflation lumen (not illustrated) or other structure for expanding other expandable components, and a filling tube 20 or other filling member 20 for delivering a filling medium or material 23 to an internal space 22 of the double-walled filling structure 12. The internal space 22 is defined between an outer wall 24 and inner wall 26 of the filling structure. Upon inflation with the filling material or medium, the outer wall will expand radially outwardly, as shown in broken line, as will the inner wall 26, also shown in broken line. Expansion of the inner wall 26 defines an internal lumen 28. The expandable balloon or other structure 16 will be expandable to support an inner surface of the lumen 28, as also in broken line in FIG. 1A.

In many embodiments, system 10 includes a pressure monitoring 60 system so as to be able to measure one or more pressures at the aneurysm site before, during or after the filling of filling structure 12. System 60 comprises a pressure sensing means 61 and a pressure monitoring means 65. Sensing means 61 can comprise one or more pressure sensors 62 placed in the interior space 22 of structure 12 so as to measure the filling pressure 69 within the structure, or placed on the external surface of outer wall 24 so as to measure the pressure the blood pressure in 68 in vessel space US, which is the space between the surface S of the aneurysms wall and outer wall 24. The sensor can comprise various pressures sensor known in the art including various solid state sensors, MEMS-based sensors, optical sensors and other miniature pressure sensors known in the art. Also multiple sensors 62 can be placed on the interior and exterior of the structure so as to produce a sensor array 62A. The sensors can be coupled to pressure monitoring means by a cable C or other electrical coupling means known in the art.

Sensing means 60 can also include a pressure sensing member 63, which can include a guidewire, catheter or like structure. Sensing member 63 can comprise a sensor tipped member such as a sensor tipped catheter, or it can have a lumen 64 for fluid communication with pressure monitoring means 65, such as an electronic pressure monitor which itself includes a pressure sensor such as a strain gauge. Embodiments of the sensing member having a lumen can also be configured to be used as a drain device 80 discussed herein.

The sensing member can be configured to be both advanceable and steerable either through the arterial vasculature or through a lumen of delivery catheter 14. In particular embodiments, it can be sized and have mechanical properties to be advanced through delivery catheter 14 into the interior space 22 of structure 12 so as to monitor the filling pressure 69 in that space. It can also be sized and have mechanical properties to be advanced into the aneurysm site AS including vessel space US from a vascular access point such as the femoral artery near the groin or the brachial artery near the arm pit. This allows the member to measure the blood pressure 68 in space US.

Figure 1C:
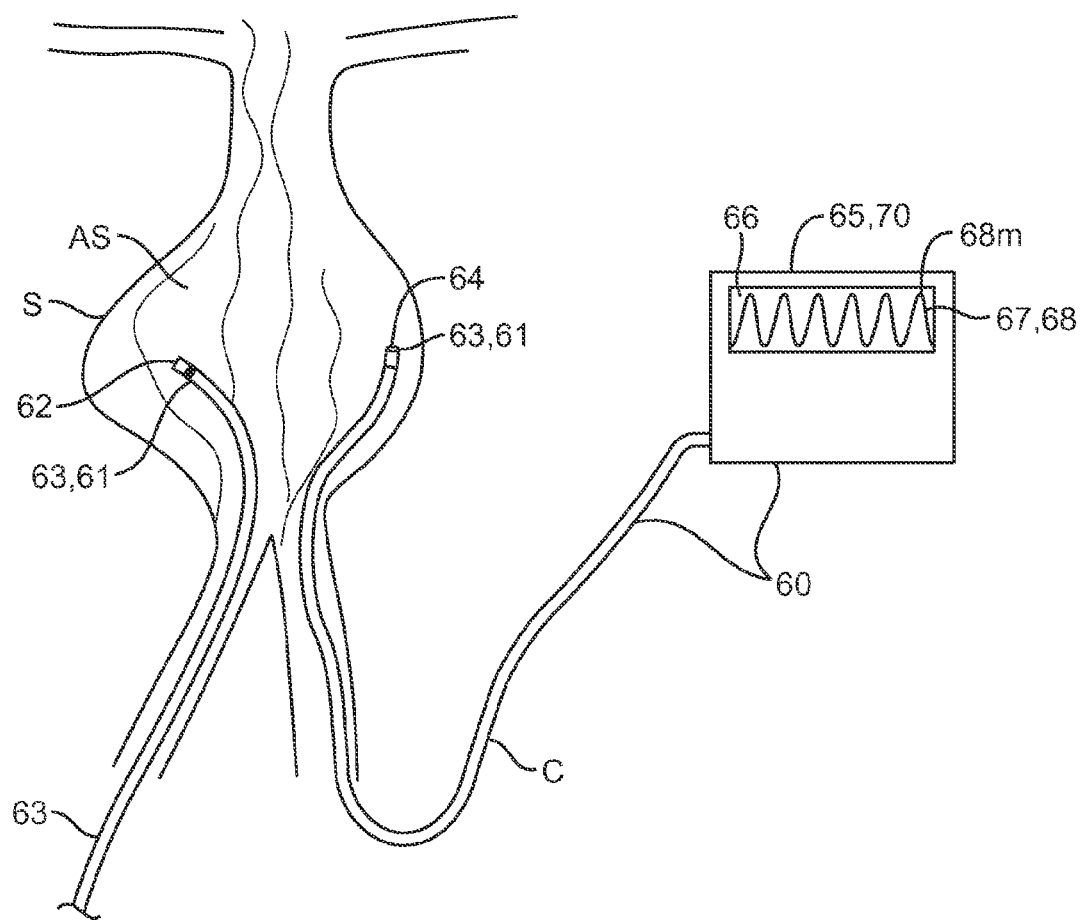
FIGS. 1C-E illustrate use of a pressure monitoring system during an aneurysm repair procedure using an fillable prosthetic implant.

In many embodiments, system 60 can include two or more pressure sensing members 63 as is shown in FIG. 1C which can be positioned at different locations in or around the aneurysm site, AS. This provides the physician with a more reliable indication of the pressure over the entire aneurysm site AS; it also provides for the ability to do differential pressure measurements over a particular length of the site (e.g. proximal to distal) as well differential measurements inside and outside of the filling structure. For example, one sensing member could be positioned in space 22 within the filling structure and another in vessel space US. It also allows the physician to spot check particular locations in vessel space US to determine if there are any areas which have trapped blood and are rising too fast in pressure. In this way, the physician can develop a pressure profile or barometric 3-dimensional map of pressure over the entire aneurysm site (both inside and out of the filling structure) and utilize that map to monitor and control the filling process and entire aneurysm repair procedure.

In various embodiments, pressure monitoring means 65 can comprise a gauge, a dedicated electronic pressure monitor, a modular monitor configured to be integrated with other medical monitoring instrumentation, computer with pressure mentoring capability or like device. Typically the monitoring means will comprise an electronic pressure monitor having a display 66 for displaying a pressure waveform 67 and/or a numeric readout. It can also be configured to have one or more alarms to alert the medical staff when a pressure threshold has been reached. The monitoring means can also be integral to or otherwise coupled to a control system 70 discussed below for controlling the filling rate and pressure of filling structure 12.

In various embodiments, one or more of the monitored pressures at site AS can be used to control the filling process of structure 12 including both the flow rate of filling medium 23 and the pressure used to fill the structure by a syringe pump or other fluid delivery means. This can accomplished by the physician eyeballing the pressure and making manual adjustments to flow rate on a syringe pump. It many embodiments, it can be accomplished by means of a control system 70 which can comprise a computer or processor 71 coupled to pressure sensing means 60 and a fluid delivery means 75. Computer 70 can include or be coupled to a pressure monitoring means 65 which in turn are coupled to pressure sensing means 60. Computer 70 can receive input signals 75 from pressuring sensing means 60 and send output signals 76 to fluid delivery means 75 for the control of the flow rate and delivery pressure of medium 23 to filling structure 12. Fluid delivery means can include a syringe pump, peristaltic pump, metered pump or other medical pump known in the art The computer include one or more modules or control algorithms 72 for controlling flow rate and pressure of fluid delivery means 75 responsive to input signal 75 from sensor means 60. Modules 72 can include one or more P, PI, or PID or other control algorithms known in the art. In many embodiments, modules 72 can be configured to utilize a threshold pressure, or rate of pressure change to control the filling process. For example, the module can be configured to slow or stop the filling rate when a monitored pressure reaches or approaches the threshold. This threshold can be pre-set by the physician or can be determined through measurement and comparison to the patients blood pressure as is explained below.

In addition to controlling the filling process, pressure monitoring, done either manually or through control system 70 can be utilized to determine an endpoint for filling the filling structure. Similar to the control of flow rate, the endpoint can be determined based upon reaching or approaching a pressure threshold either absolute or a rate of change. Pressure monitoring can be used to determine the endpoint out right, or in some cases can be used to titrate or fine tune endpoint determination by coupling this information together with observation of the deployed size of the filling structure and total volume of medium delivered. Computer 71 can be programmed to alert the physician when an endpoint is approaching based on pressure measurement and then allow the physician to fine tune the process. The computer can also be programmed to give the physician a pressure range or window for making a manual endpoint decision with an ultimate shut off value. In this way the system affords the physician the ability to fine tune the endpoint while still providing a fail safe protection function to prevent the physician from exceeding a pressure threshold which may cause dissection or other damage to the aneurysm wall.

Figure 2:
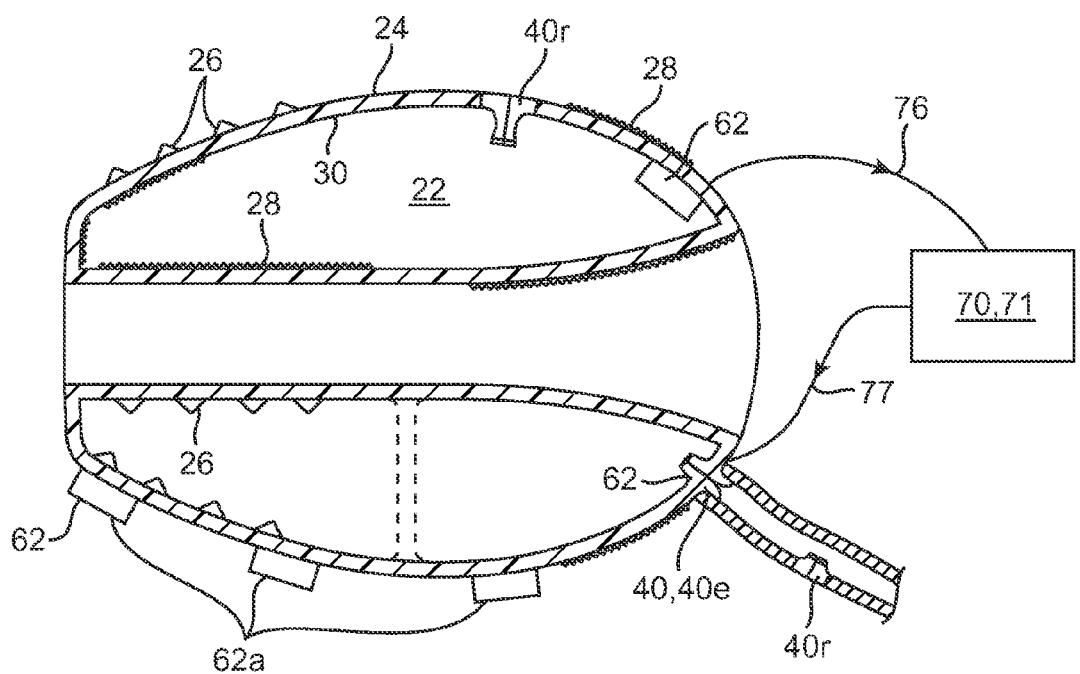
FIG. 2 is a cross-sectional view of the filling structure of FIG. 1A illustrating various surface modifications and a filling valve.

In various embodiments, filling can also be controlled by means of a valve 40 coupled to filling structure 12 either directly or to filling tube 20 as is shown in FIG. 2. In one embodiment, the valve can be configured as a mechanical pressure relief valve 40r configured to open and relieve pressure from interior 22 when a threshold pressure has been reached. In another embodiment the valve can be an electronically controlled valve 40e which either opens to relieve pressure within the filling structure when the threshold pressure is reached or closes to prevent the influx of additional filling medium. In the former case, the valve can be coupled to an exterior wall of the filling structure and in the latter case it can be coupled to filling tube 20 or other filling member used to fill the filling structure. The electronic valve 40e can be controlled responsive to a pressure signal directly from a pressure sensor 62, or a signal 77 from control system 70.

Figure 1D:
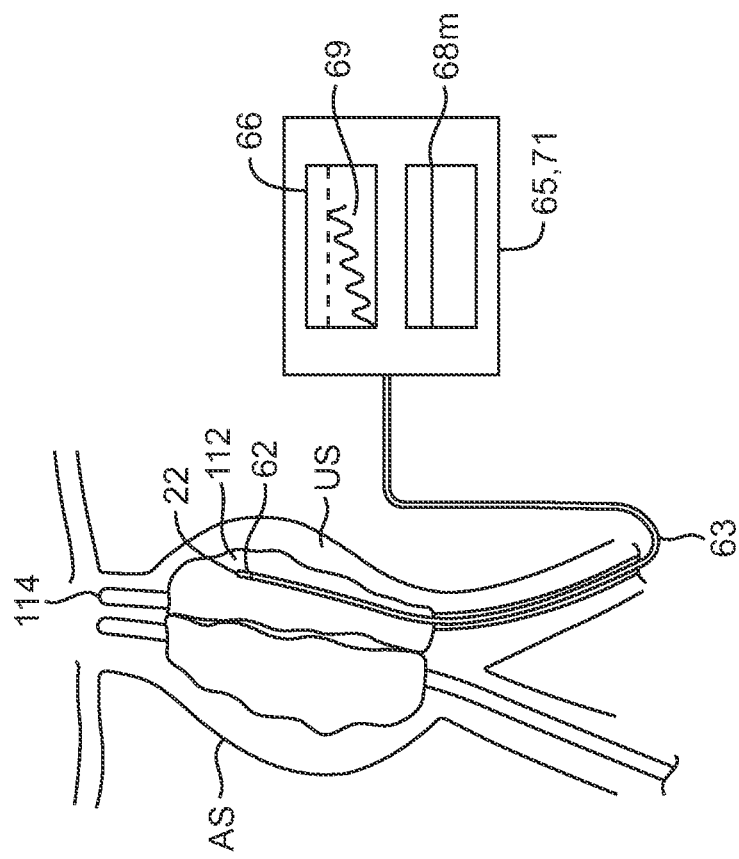
Figure 1E:
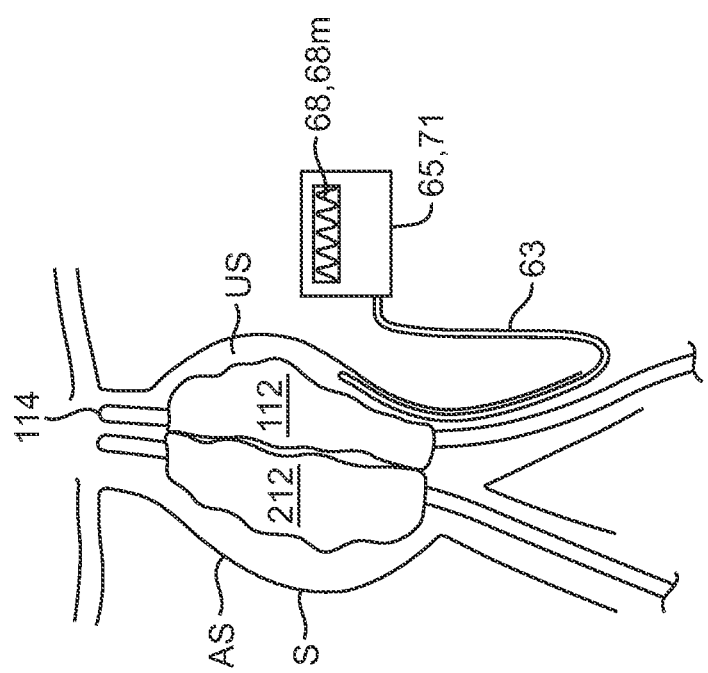

Referring now to FIGS. 1C-E, in various embodiments, the patient blood pressure can be utilized in determining a pressure threshold for both controlling the filling process and determining an endpoint for filling. In one embodiment, sensing system 60 can be used to measure the patient's blood pressure 68 at the aneurysm site AS, such as their maximum systolic pressure, before placement of filling structure 12 as is shown in FIG. 1C. This maximum value 68m then becomes the threshold value that is used for control of the filling process. Other values can also be used such maximum diastolic pressure, or maximum time averaged pressure (e.g., over one minute). One or more filling structures can then be deployed and filled as shown in FIG. 1D with a pressure sensing member positioned in the interior 22 of the filling structure to monitor filling pressure 69. Filling can be completed when the filling pressure remains at or slightly above maximum pressure 68m, for example by 10% to 20%. This can also be corroborated by imaging observation to see if the filling structures are fully inflated and/or slightly oversized to see that filling structures are completely filling in the aneurysm. In a different approach shown in FIG. 1E, filling can be completed based on a measured maximum or other value of blood pressure in vessel space, US. This measurement can also be compared to the prior measure maximum value 68m without the filling structure in place.

Referring now to FIG. 2, the various internal and external surfaces may be shaped, coated, treated, or otherwise modified to provide for a number of particular features in accordance with the principles of the present invention. For example, the outer wall 24 may be shaped to have rings, stipples, or other surface features which are typically formed into the material of the structure at the time of molding, vapor deposition, or other manufacturing process. The outer surface may also be coated with materials 28 which can be adhesives, drugs, active substances, fibers, flocking, foams, or a variety of other materials. In most cases, such surface features or modifications will be intended to enhance sealing or attachment of the outer wall 24 to the inner surface of the aneurysm being treated.

The inner surface 30 of the filling volume 22 may also be modified by providing features, coatings, surface roughening, or a variety of other modifications. The purpose of such internal features is typically to enhance adherence of the walls to the filling material or medium as the medium is cured or otherwise hardened. In some instances, materials may be coated on all or a portion of the inside surface 30 to induce or catalyze hardening of the filling material as it is being introduced.

The double-walled filling structure 12 will typically comprise at least one valve 40 to permit the introduction of the filling material or medium into the internal volume 22. As illustrated, the valve 40 may be a simple flap valve. Other more complex ball valves, and other one-way valve structures may be provided. In other instances, two-way valve structures may be provided to permit both filling and selective emptying of the internal volume 22. In other instances, the filling tube may comprise a needle or other filling structure to pass through the valve 40 to permit both filling and removal of filling medium. Valve 40 may also be configured as a mechanical pressure release valve 40r configured to open and relieve pressure when the filling in space 22 exceeds a preset threshold. Such pressure relieve valves 40r can be placed both in supply tube 20 and also in the external wall 24 of the filling structures. When they open, such valves allow filling medium to exit the filling structure when placed in wall 24 or divert it from entering in the first place when placed in supply tube 20. Valve 40 can also be an electronically controlled valve 40e configured to shut off in response to a signal from a pressure control system 70, or directly from a pressure sensor 62 described herein so as to stop the inflow of medium 23 when the pressure in space 22 exceeds a threshold.

Figure 3A:
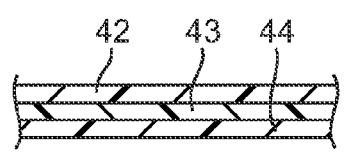
FIGS. 3A-3C illustrate alternative wall structures for the filling structure.
Figure 3B:
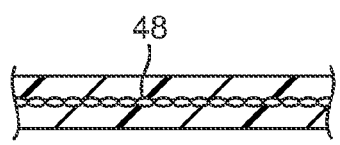
Figure 3C:
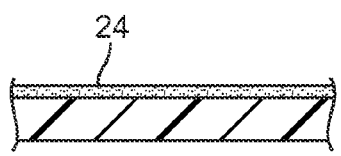

As illustrated in FIG. 2, the wall structure of the double-walled filling structure may be a single layer, typically molded or otherwise conventionally formed. The wall structures may also be more complex, for example, as illustrated by FIGS. 3A-3C. FIG. 3A shows a multi-layered wall comprising layers 42, 43 and 44. It will be appreciated that such multiple layer structure can provide for increased strength, puncture resistance, variations in compliance and/or flexibility, differences in resistance to degradation, and the like. As shown in FIG. 3B, a single wall or multiple wall structure can be reinforced by braid, coils, or other metal or non-polymeric reinforcement layers or structures. As shown in FIG. 3C, the external surface 24 of the wall may be covered with drugs, fibers, protrusions, holes, active agents or other substances for a variety of purposes.

Figure 4:
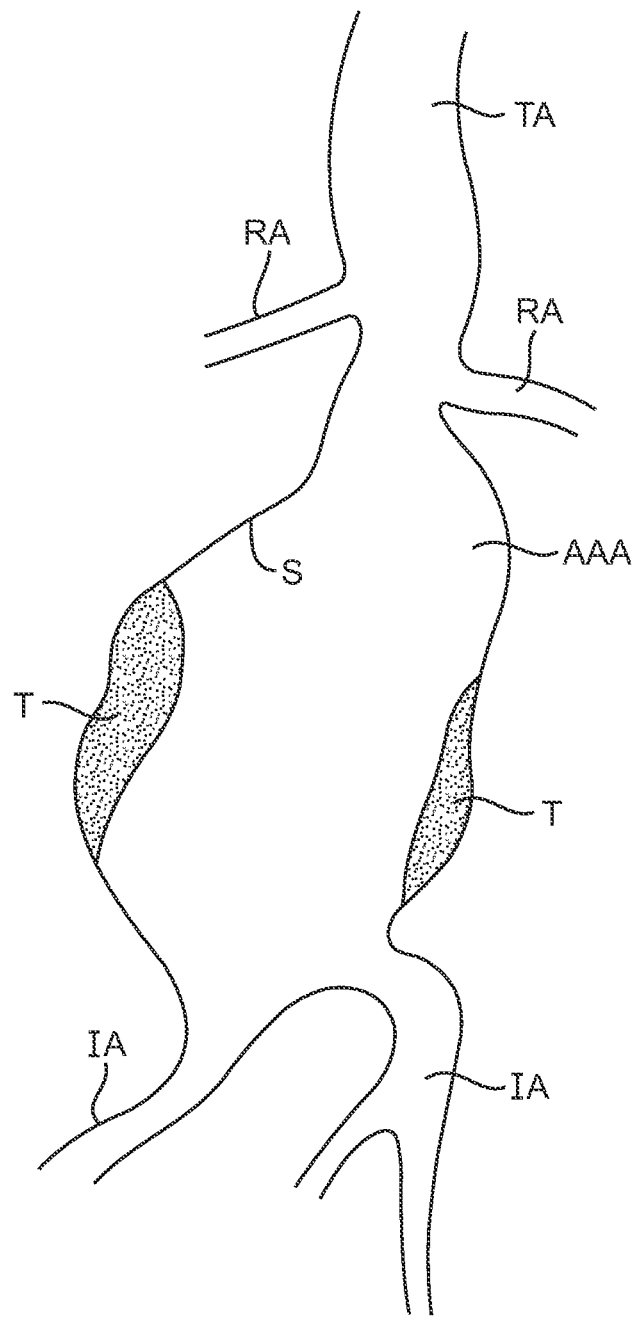
FIG. 4 illustrates the anatomy of an infrarenal abdominal aortic aneurysm.

Referring now to FIG. 4, the anatomy of an infrarenal abdominal aortic aneurysm comprises the thoracic aorta (TA) having renal arteries (RA) at its distal end above the iliac arteries (IA). The abdominal aortic aneurysm (AAA) typically forms between the renal arteries (RA) and the iliac arteries (IA) and may have regions of mural thrombus (T) over portions of its inner surface (S).

Figure 5A:
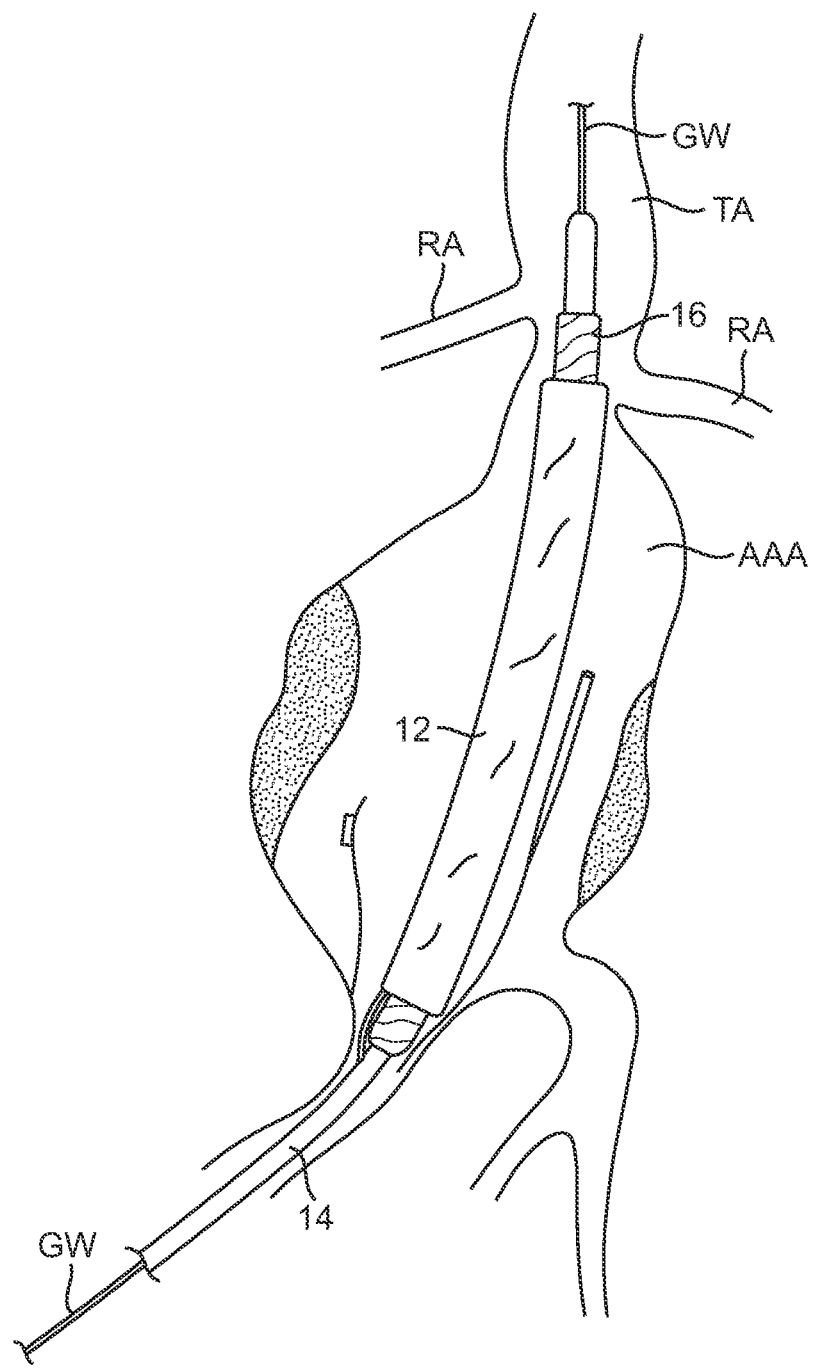
FIGS. 5A-5D illustrate use of the prosthesis system of FIG. 1 for treating the infrarenal abdominal aortic aneurysm.

Referring to FIGS. 5A-5D, the treatment system 10 of FIG. 1 may be utilized to treat the complex geometry of the transmural abdominal aortic aneurysm (AAA) of FIG. 4 by first positioning the delivery catheter 14 to place the double-walled filling structure 12 (in its unfilled configuration) generally across the aneurysm from the region of the aorta beneath the renal arteries (RA) to a region over the iliac arteries (IA), as best seen in FIG. 5A. Usually, the delivery catheter 14 will be introduced over a guidewire (GW) through a puncture in the patient's groin accessing the iliac artery by the Seldinger technique.

After the double-walled filling structure 12 is properly positioned, a hardenable inflation medium is introduced into the internal space 22. Filling of the inner space 22 then expands the outer wall 24 of the structure outwardly so that it conforms to the inner surface (S) of the aneurysmal space.

Figure 5B:
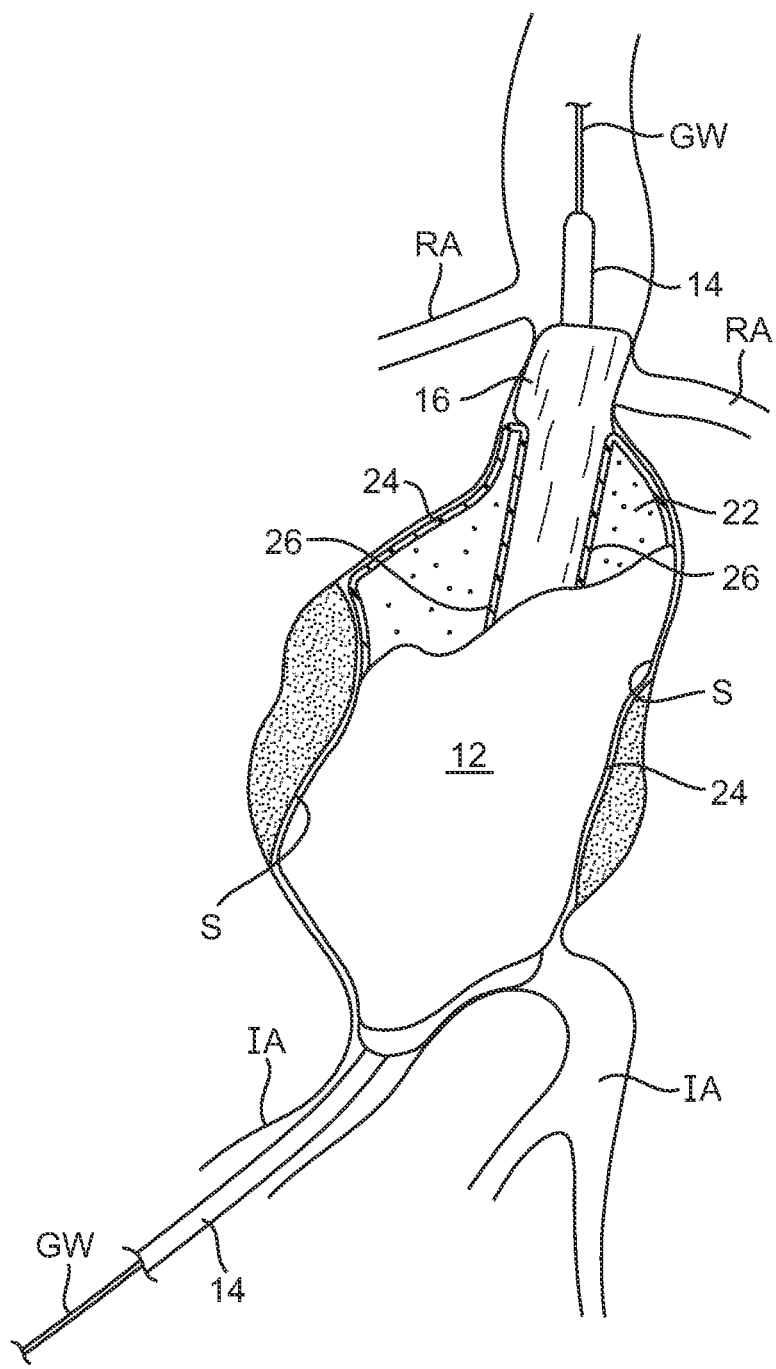
Figure 5C:
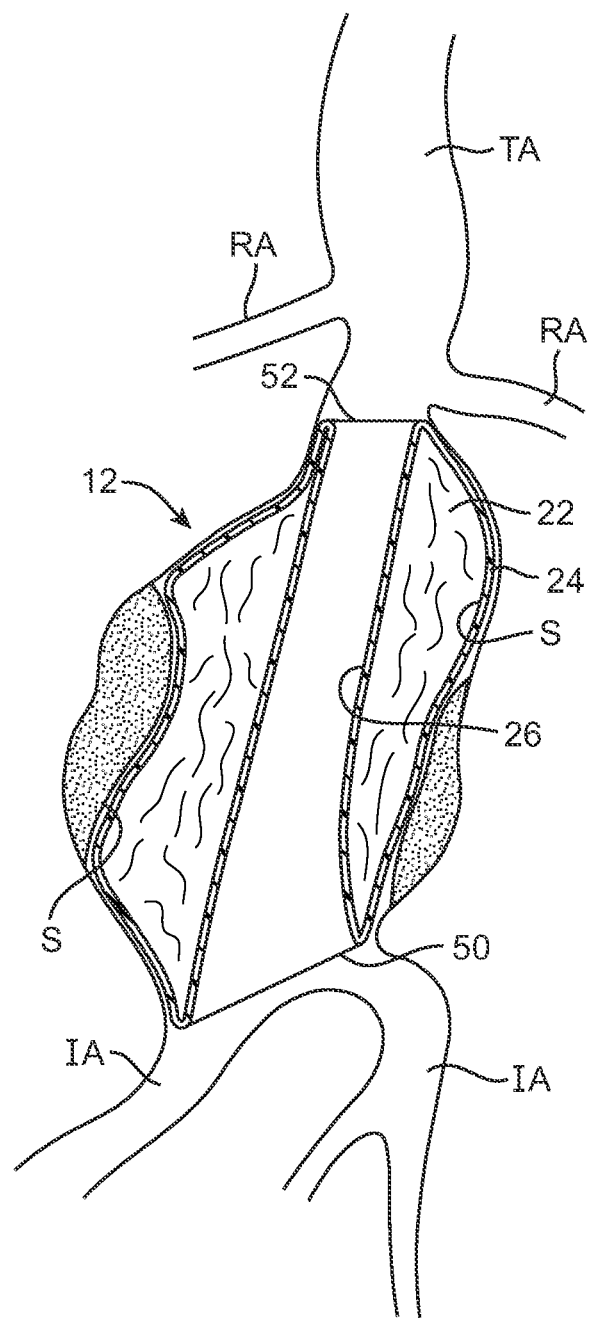

Before, during, or after filling of the double-walled filling structure 12 with inflation medium, as illustrated in FIG. 5B, the balloon 16 or other expansible structure will also be inflated or expanded to open the tubular lumen defined by the interior of the inner wall 26. In a preferred embodiment, the balloon 16 will be generally non-compliant, typically having a maximum diameter of width which is at or slightly larger than the desired tubular lumen diameter or width through the deployed filling structure 12. The filling structure 12, in contrast, will be partially or completely formed from a generally compliant material, thus allowing the non-compliant balloon or other expansible structure 16 to fully open the tubular lumen and conform to the ends of the lumens to the aorta and iliac walls, as illustrated in FIG. 5C. A lower or proximal end 50 of the tubular lumen will be flared to a larger diameter so that it can accommodate the openings of both the iliac arteries (IA) as illustrated. Thus, it will be preferred to utilize a filling structure 12 geometry which has been chosen or fabricated to match the particular patient geometry being treated. It will also be preferable to use a balloon 16 or other expansible structure which will be shaped to preferentially open the lower proximal end 50 of the tubular lumen to a larger diameter than the upper or distal end 52.

After the filling material has been introduced to the filling structure 12, typically through the filling tube 20, the fluid filling material can be cured or otherwise hardened to provide for the permanent implant having a generally fixed structure which will remain in place in the particular aneurysmal geometry. Pressure monitoring can be performed during all or a portion of the hardening period and can be used to determine an amount or endpoint of hardening. Methods for curing or hardening the filling material will depend on the nature of the filling material. For example, certain polymers may be cured by the application of energy, such as heat energy or ultraviolet light. Heat energy can be applied using various energy delivery means including RF, ultrasonic and infrared delivery means. Other polymers may be cured when exposed to body temperature, oxygen, or other conditions which cause polymerization of the fluid filling material. Still others may be mixed immediately prior to use and simply cured after a fixed time, typically minutes. Often, after the filling material has been hardened, the delivery catheter 12 may be removed and the filling structure left in place as the completed prosthetic implant. The pressure sensing and/or drain device (discussed herein) can also be removed at this time or left in place for a selected period. In still other embodiments, the filling medium need not be hardenable/curable but rather has rheological properties configured to mimic blood or native tissue. Such mediums can include various silicone solutions known in the art.

Figure 5D:
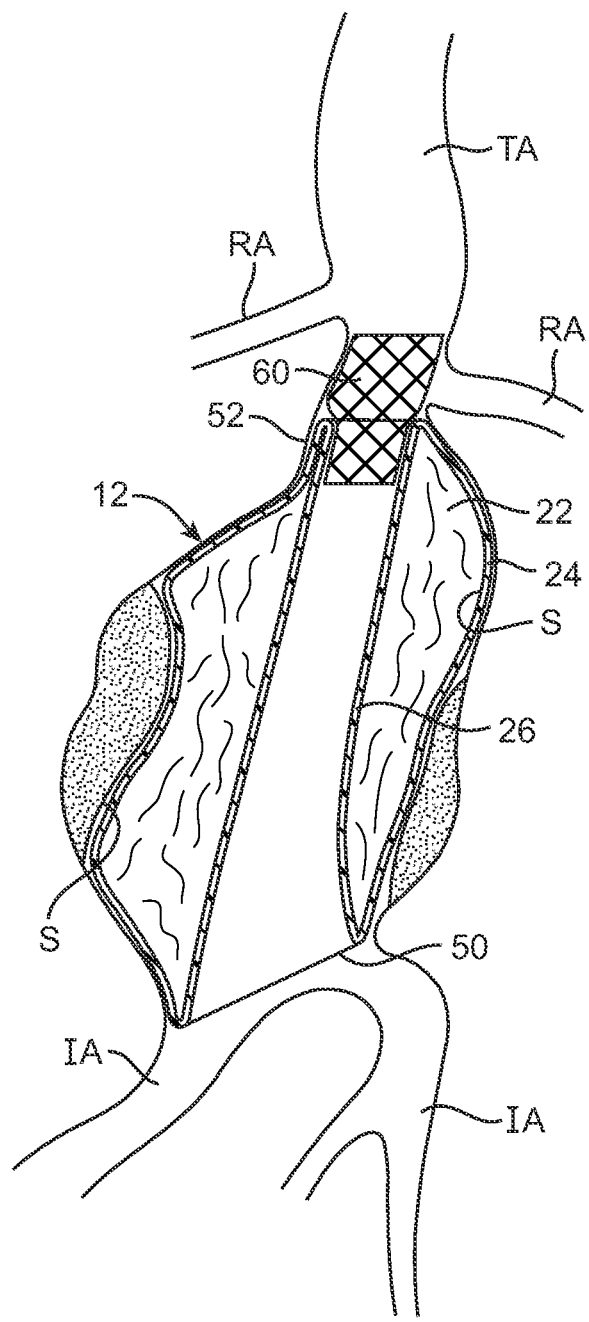

In other cases, however, it may be desirable to further position certain seals, anchors, stents, or other additional prosthetic components at either the proximal end 52 or distal end 50 of the graft. As illustrated in FIG. 5D, for example, a stent-like structure may be planted in the upper proximal opening 52 of the tubular lumen of the filling structure 12 in order to help anchor the structure, help prevent intrusion of blood into the region between the outer wall 24 and inner surface (S) of the aneurysm, and to generally improve the transition from the aorta into the tubular lumen. The sealing or anchoring structure may simply comprise a stent-like component, preferably having a port or other access route to allow blood flow into the covered renal arteries (if any). Alternatively, the anchor structure could be another inflatable unit, such as the anchor described in co-pending, commonly owned application Ser. No. 10/668,901 (published as US2004/0116997A1), the full disclosure of which is incorporated herein by reference.

Figure 6:
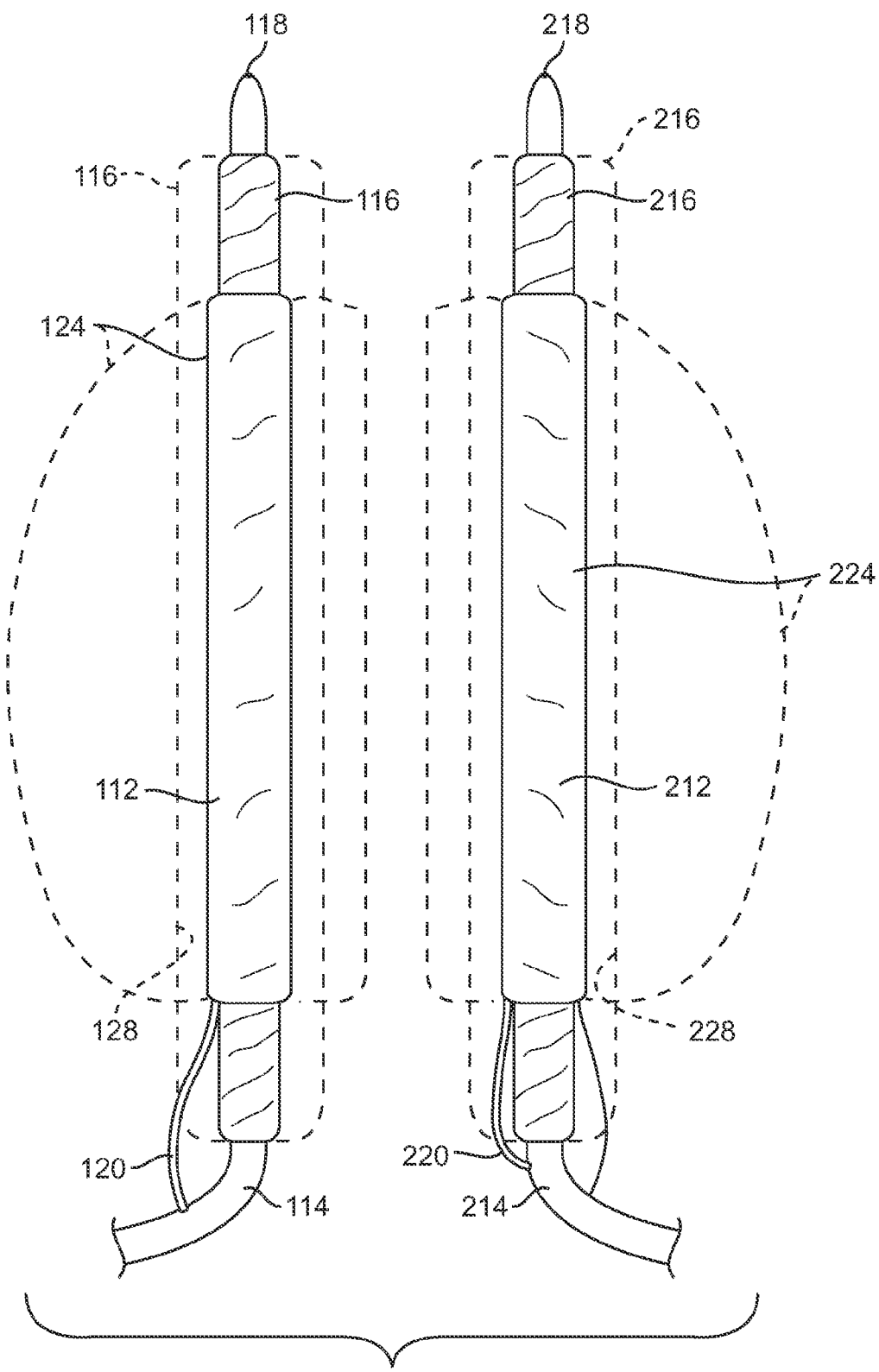
FIG. 6 illustrates a system in accordance with the principles of the present invention comprising a pair of prosthesis for delivery to an infrarenal abdominal aortic aneurysm, where each prosthesis comprises a filling structure mounted on a delivery catheter.

In a particular and preferred aspect of the present invention, a pair of double-walled filling structures will be used to treat infrarenal abdominal aortic aneurysms, instead of only a single filling structure as illustrated in FIGS. 5A-5C. A system comprising such a pair of filling structures is illustrated in FIG. 6 which includes a first filling structure 112 and a second filling structure 212. Each of the filling structures 112 and 212 are mounted on delivery catheters 114 and 214, respectively. The components of the filling structures 112 and 212 and delivery catheters 114 and 214 are generally the same as those described previously with respect to the single filling structure system 10 of FIG. 1. Corresponding parts of each of the fillings systems 112 and 212 will be given identical numbers with either the 100 base number or 200 base number. A principal difference between the filling structures 112 and 212, on the one hand, and the filling structure 12 of FIG. 1 is that the pair of filling structures will generally have asymmetric configurations which are meant to be positioned adjacent to each other within the aneurysmal space and to in combination fill that space, as will be described with specific reference to FIG. 7A-7F below.

Figure 7A:
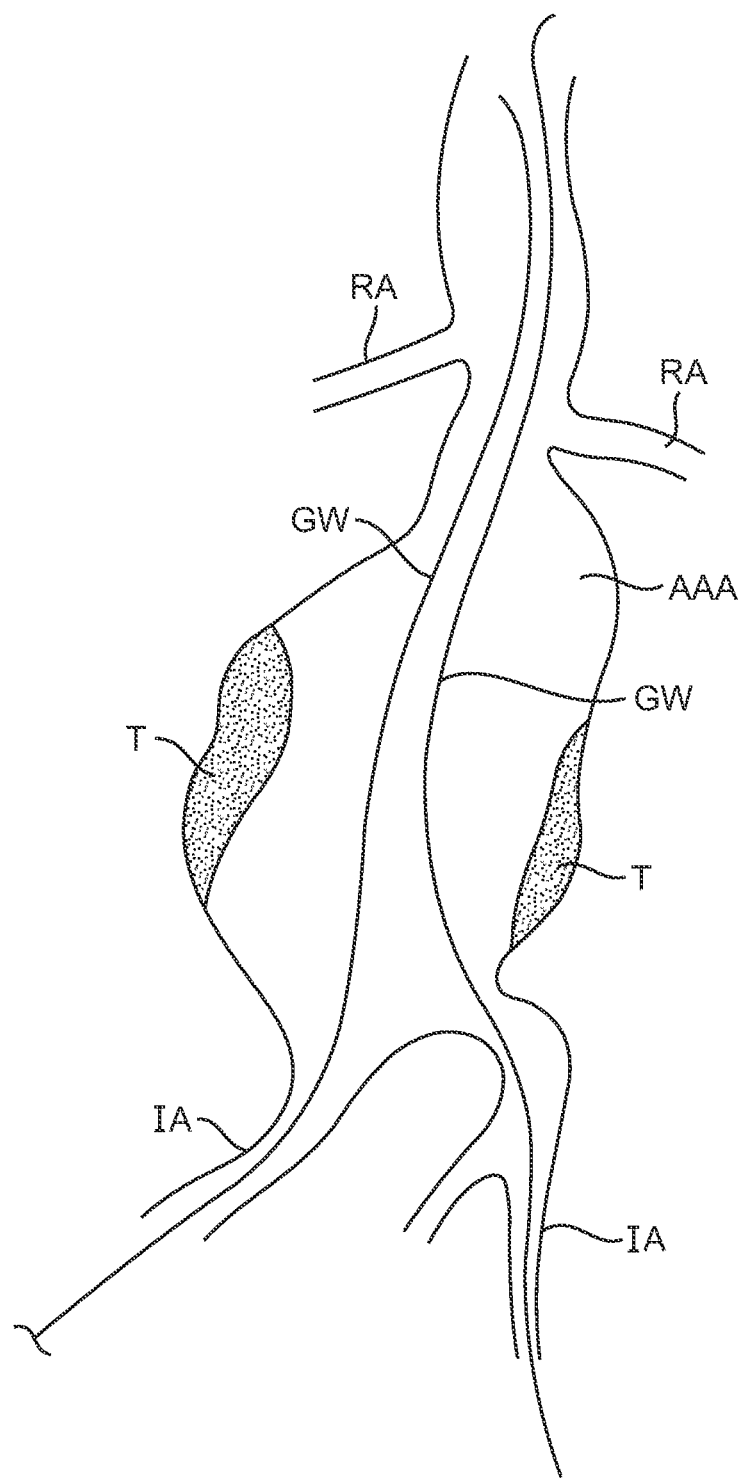
FIGS. 7A-7F illustrate use of the prosthesis system of FIG. 6 for treating an infrarenal abdominal aortic aneurysm.
Figure 7B:
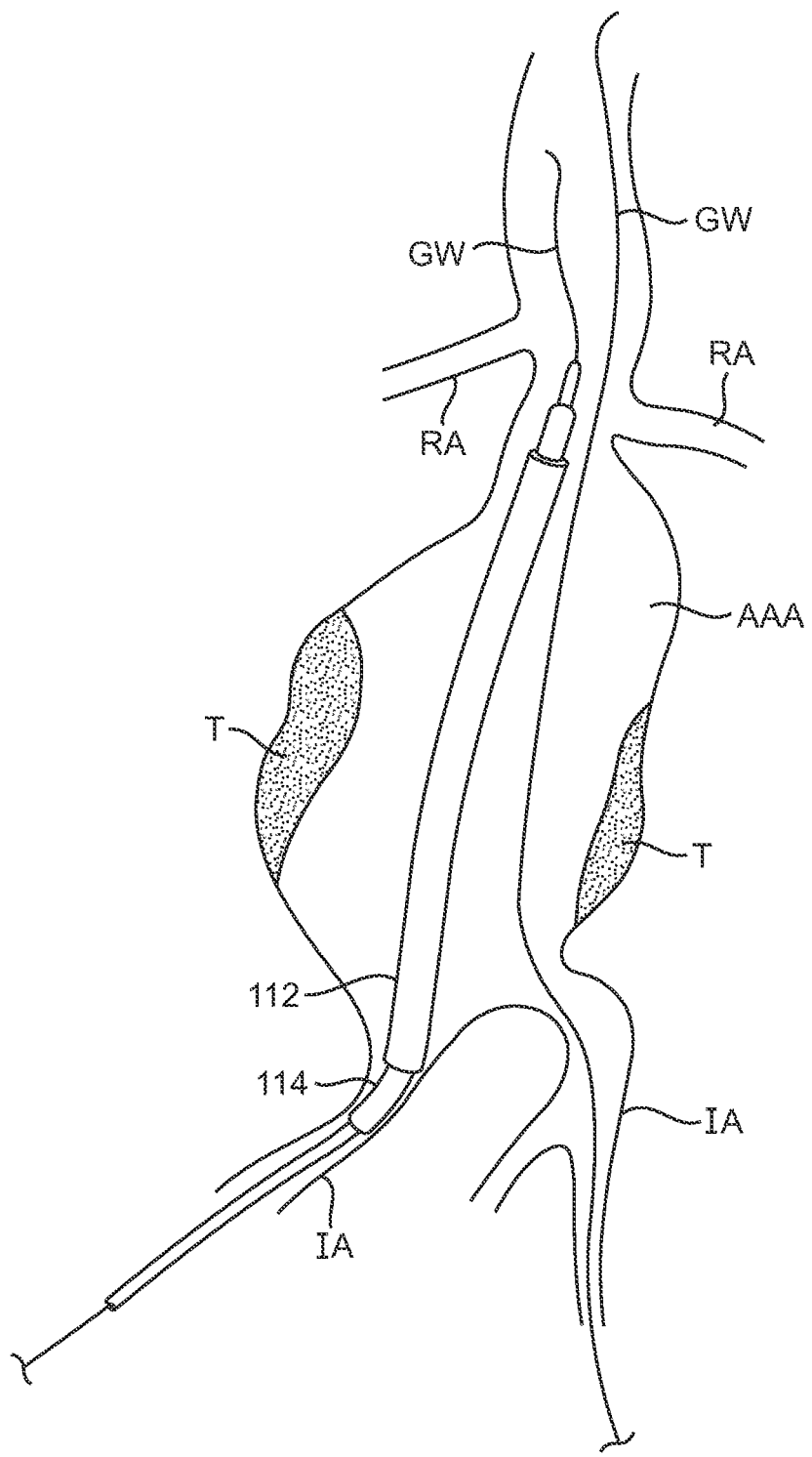
Figure 7C:
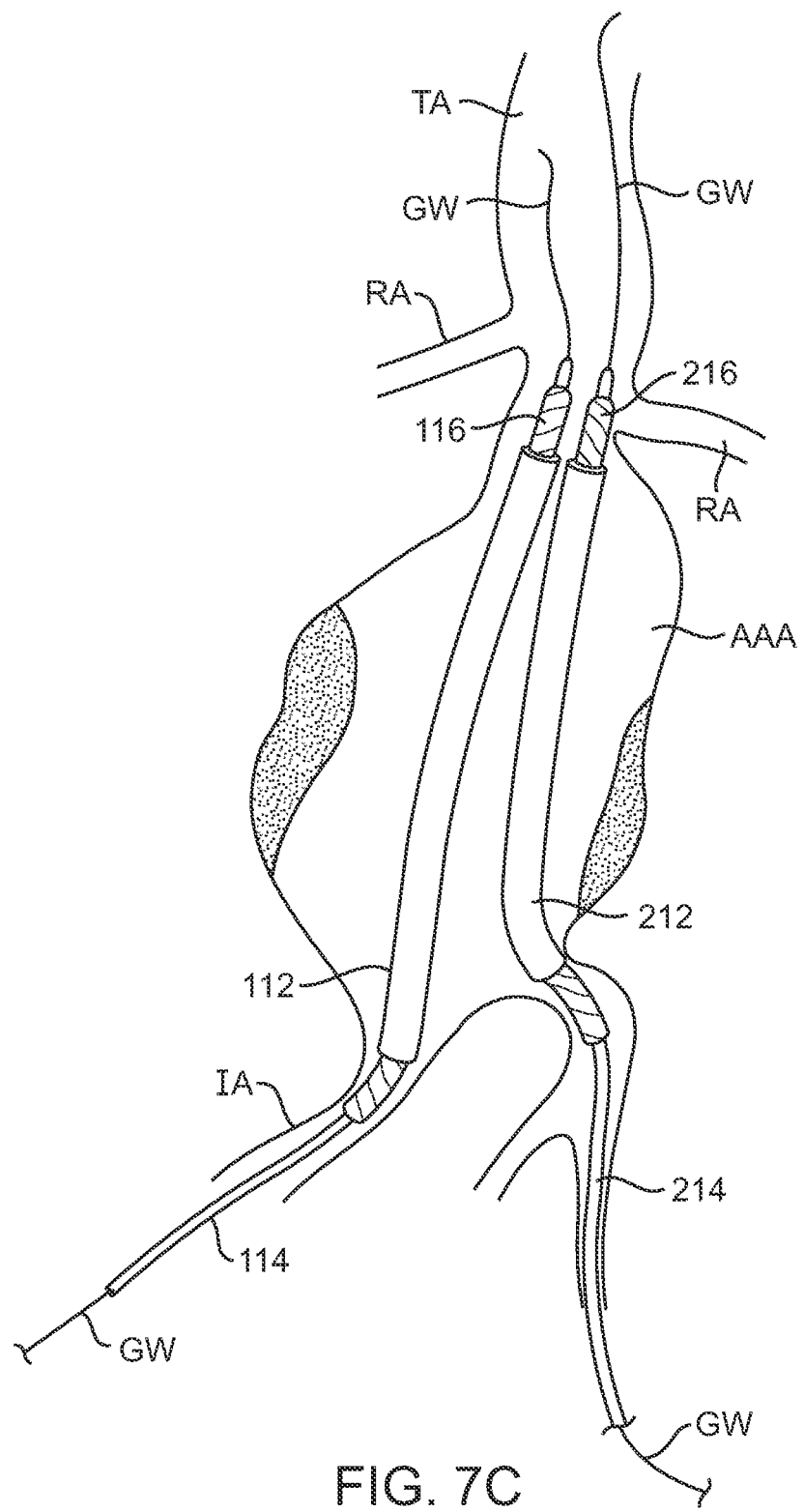
Figure 7D:
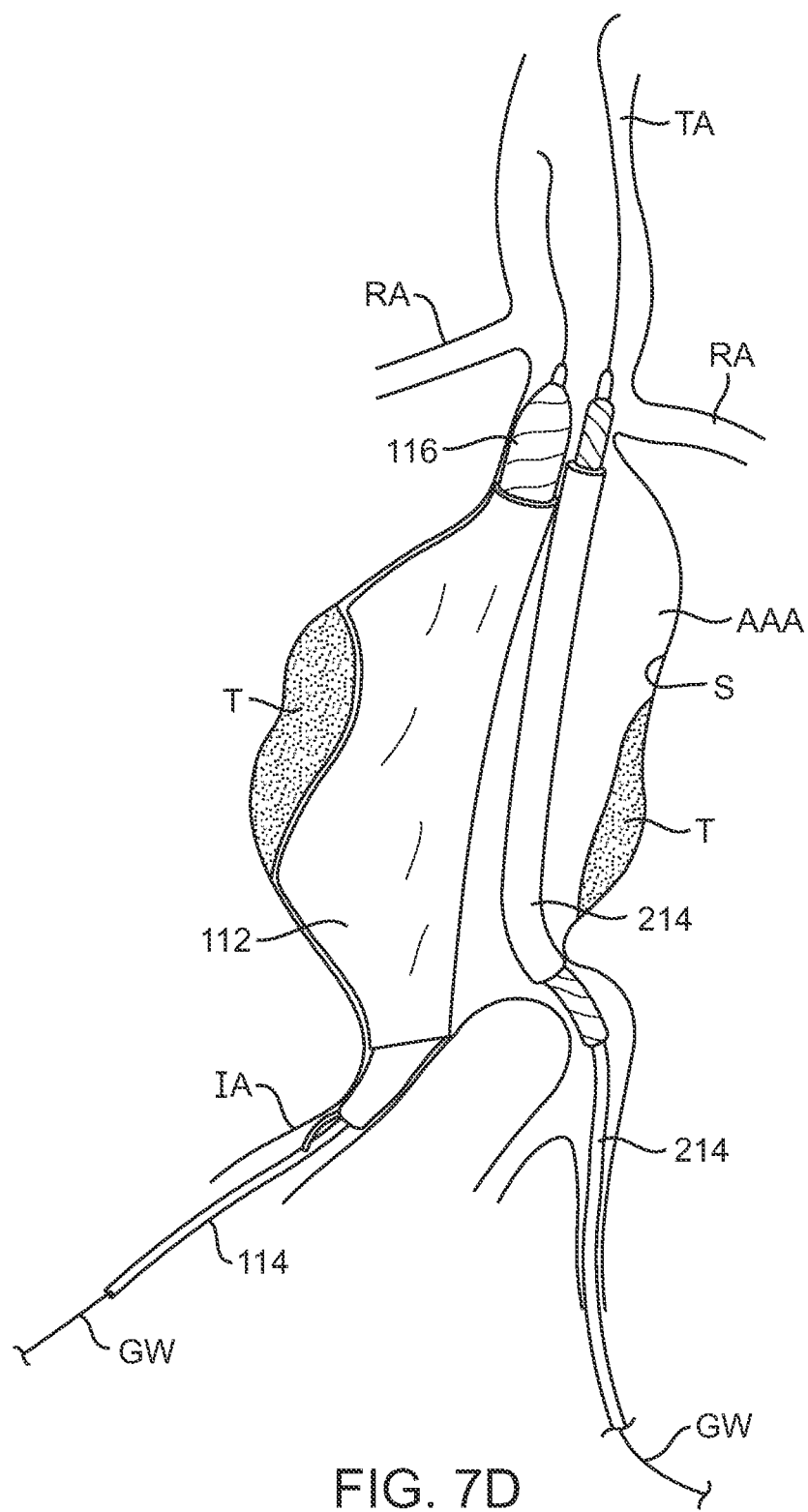
Figure 7E:
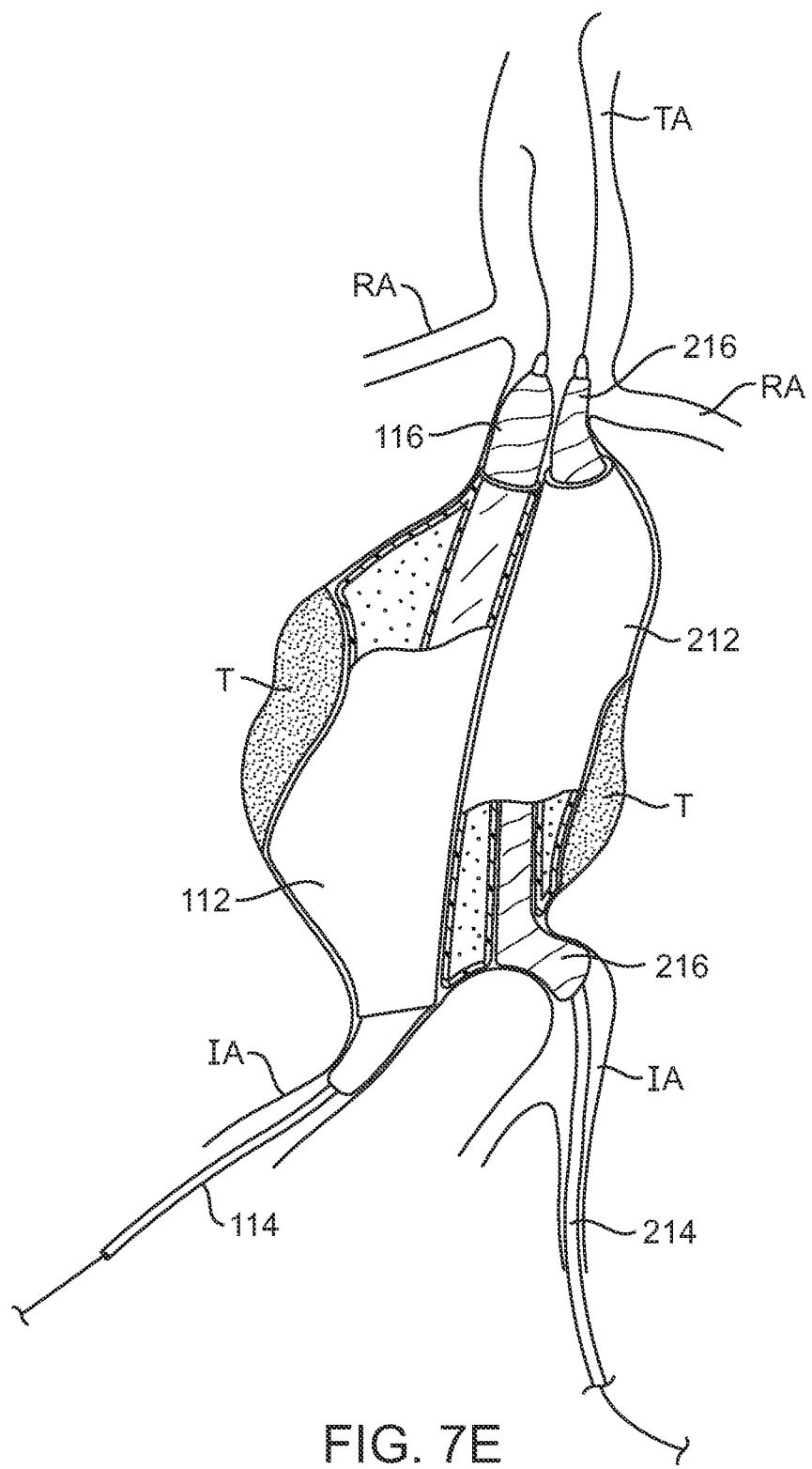

In treating an infrarenal abdominal aortic aneurysm using the pair of filling structures 112 and 212 illustrated in FIG. 6, a pair of guidewires (GW) will first be introduced, one from each of the iliac arteries (IA). As illustrated in FIG. 7A, the first delivery catheter 114 will then be positioned over one of the guidewires to position the double-walled filling structure 112 across the aortic aneurysm (AAA), as illustrated in FIG. 7B. The second delivery catheter 214 is then delivered over the other guidewire (GW) to position the second filling structure 212 adjacent to the first structure 112 within the aneurysm (AAA), as illustrated in FIG. 7C. Typically, one of the filling structures and associated balloons will be expanded first, followed by the other of the filling structures and balloon, as illustrated in FIG. 7D where the filling structure 112 and balloon 116 are inflated to fill generally half of the aneurysmal volume, as illustrated in FIG. 7D. Filling can generally be carried out as described above with the one filling structure embodiment, except of course that the filling structure 112 will be expanded to occupy only about one-half of the aneurysmal volume. After the first filling structure 112 has been filled, the second filling structure 212 may be filled, as illustrated in FIG. 7E. The upper ends of the balloons 116 and 216 will conform the tubular lumens of the filling structures against the walls of the aorta as well as against each other, while the lower ends of the balloons 116 and 216 will conform the tubular lumens into the respective iliac arteries (IA).

Figure 7F:
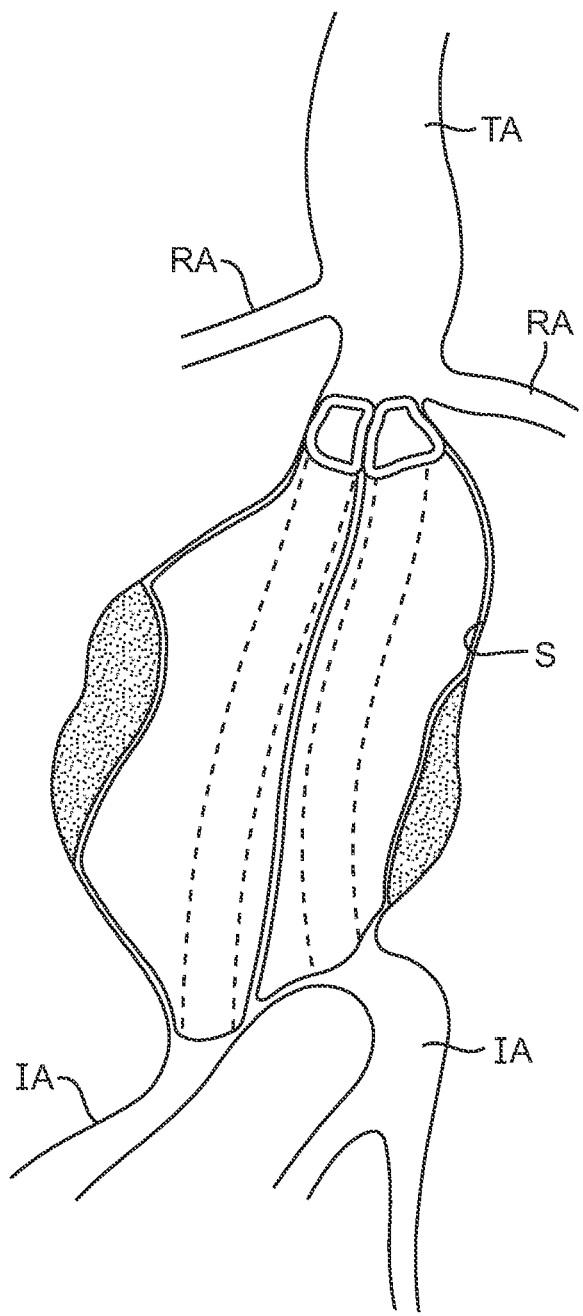

After filling the filling structures 112 and 212 as illustrated in FIG. 7E, the filling materials or medium will be cured or otherwise hardened, and the delivery catheters 114 and 214 removed, respectively. The hardened filling structures will then provide a pair of tubular lumens opening from the aorta beneath the beneath the renal arteries to the right and left iliac arteries, as shown in broken line in FIG. 7. The ability of the filling structures 112 and 212 to conform to the inner surface (S) of the aneurysm, as shown in FIG. 7F, helps to assure that the structures will remain immobilized within the aneurysm with little or no migration. Immobilization of the filling structures 112 and 114 may be further enhanced by providing any of the surface features described above in connection with the embodiments of FIG. 2. Optionally, and not illustrated, anchoring or sealing structures could be provided in either of the upper or proximal openings of the tubular lumens into the aorta or from either of the distal or lower openings into the respective iliac arteries.

Figure 8A:
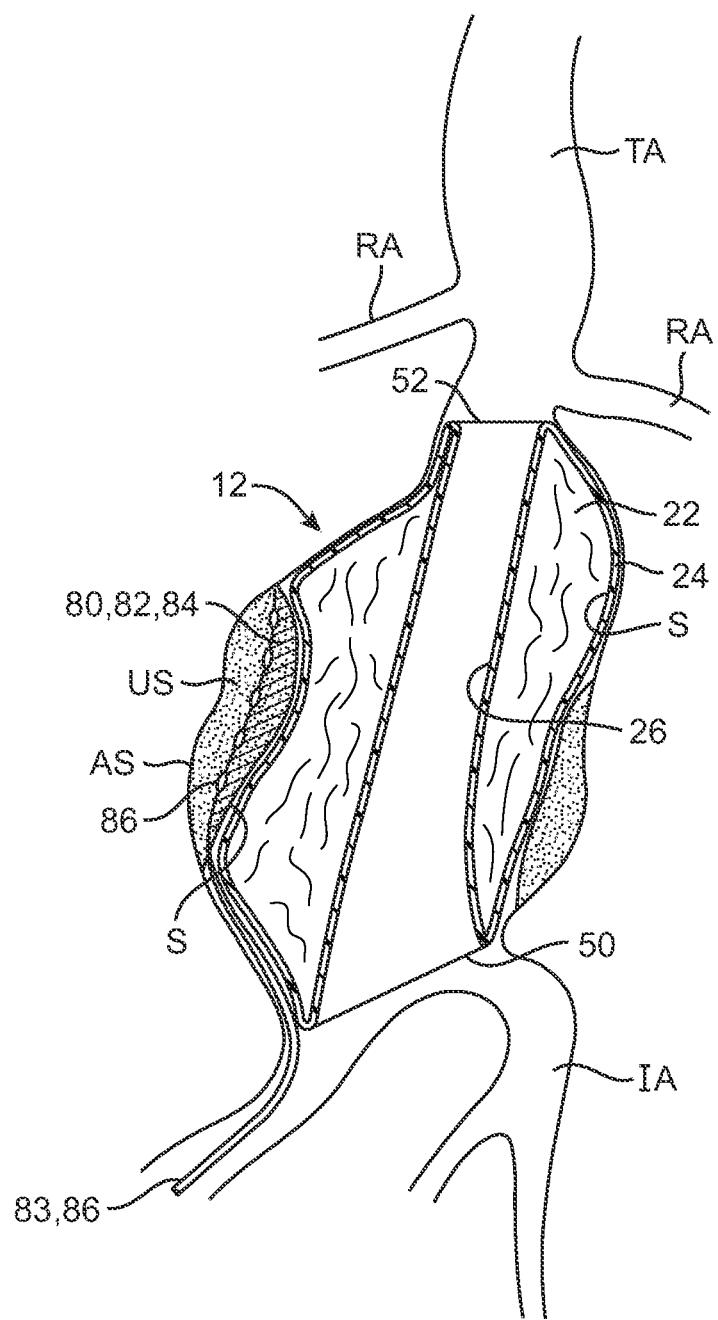
FIGS. 8A-8D illustrate use and placement of a drain device with embodiments of the prosthesis system.
Figure 8D:
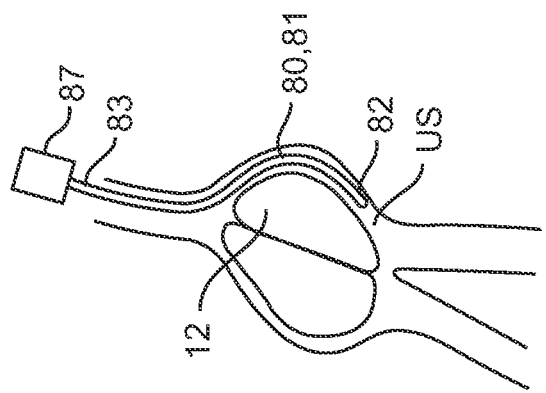
Figure 8C:
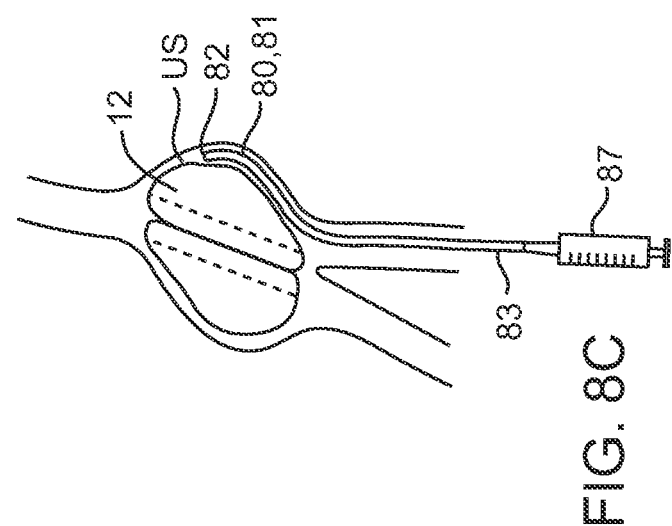
Figure 8B:
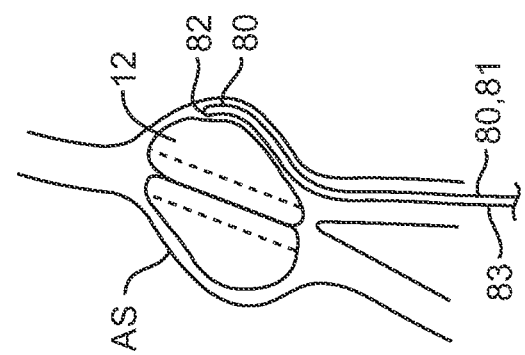
Figure 9B:
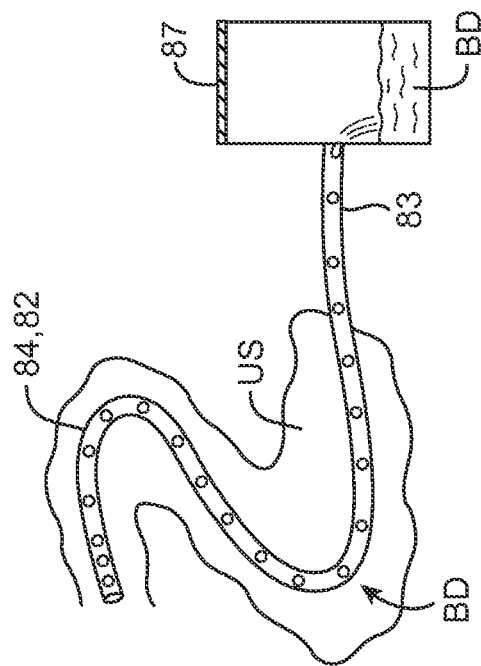
FIGS. 9A-9F illustrate different embodiments of a drain device for use with embodiments of the prosthesis system.
Figure 9A:
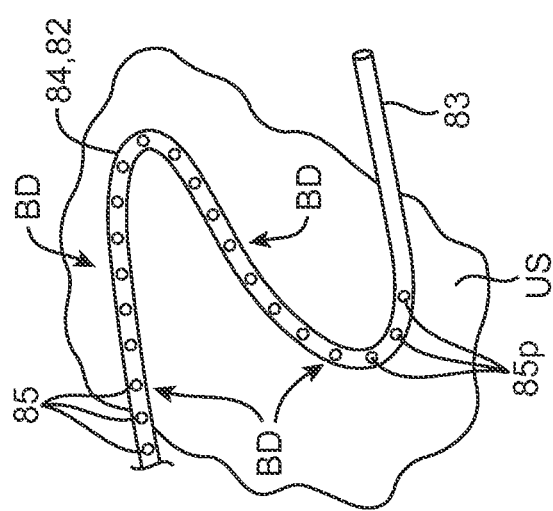
Figure 9C:
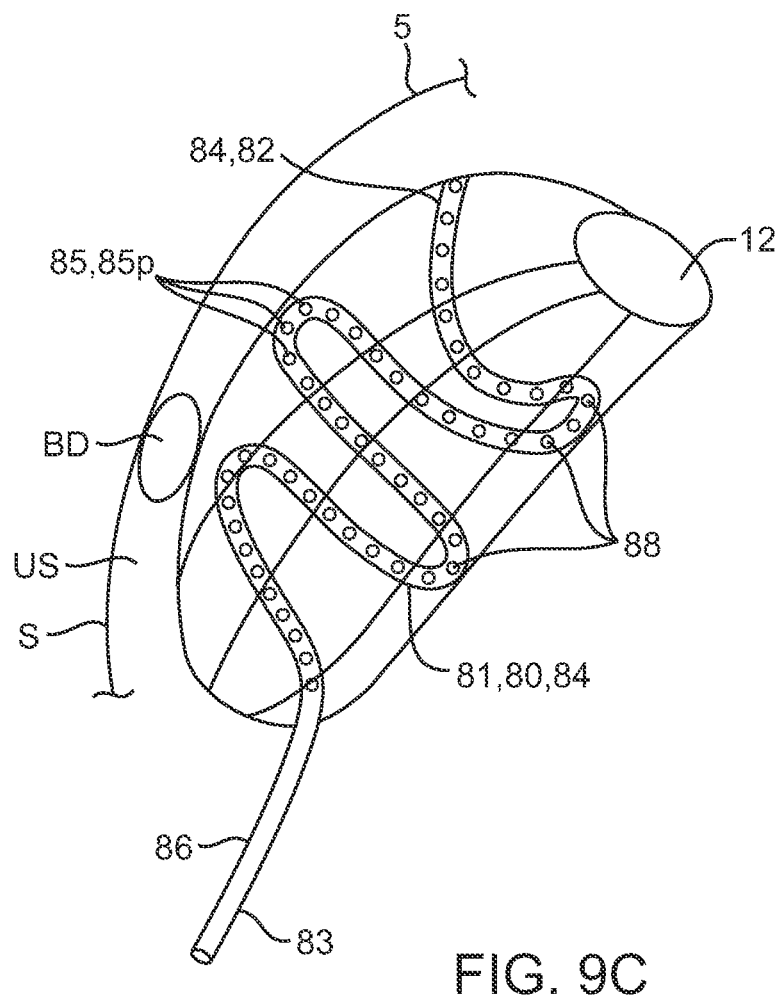

Referring now to FIGS. 8A-D, in various embodiments system 10 can include a drain device 80. Drain device 80 provides for the draining of blood and other fluid from the vessel space (VS) between the aneurysms wall (AW) and the external surface S of the filling structure 12. By removing blood or other fluid which may be trapped in space VS during filling of the filling structure draining serves to reduce the pressure forces exerted against the aneurysm wall by the expansion of filing structure and thus reduce the associated risk of aneurysm dissection or rupture. The device can be configured to provide for passive draining from the pressure exerted by blood BD in space VS (as is shown in FIG. 8B) or active draining from a vacuum source 87 such as a syringe (as is shown in FIGS. 8C and 8D). The device can be configured to be temporally or permanently left in place at site AS In many embodiments, the drain device will comprise a flexible member having an inflow portion 82 to provide for the inflow of blood BD other fluid and a outflow portion 83 to provide for the outflow either into adjoining vessels or external to the patient's body. As shown in FIGS. 9A and 9B, inflow portion 82 can comprise a porous portion 84 which can have a plurality of apertures 85 provide for inflow of fluid from multiple locations over portion 82 and also provides redundancy should one or more of the apertures become blocked with thrombus or other matter. In one embodiment shown in FIG. 9C, inflow portion 81 will be helically or otherwise wrapped around the circumference of structure 12 so as to define a drainage volume or geometry 88. Various drainage geometries such as spherical, cylindrical etc., can be defined based on the positioning of the porous portion around the filling structures and the shape of the filling structure. Also the pattern 85p and shape of apertures 85 over geometry 88 can be configured to optimize draining for a particular orientation of the drain. For example, in cases of downstream passive draining, the more proximal section of the porous portions can have a greater aperture density and/or larger diameter apertures. These and related configurations of the porous portion provides for drainage of blood BD from multiple locations within space US so as to produce more uniform draining and minimize the likelihood of blood BD or other fluid from becoming trapped within a particular location within space.

Figure 9D:
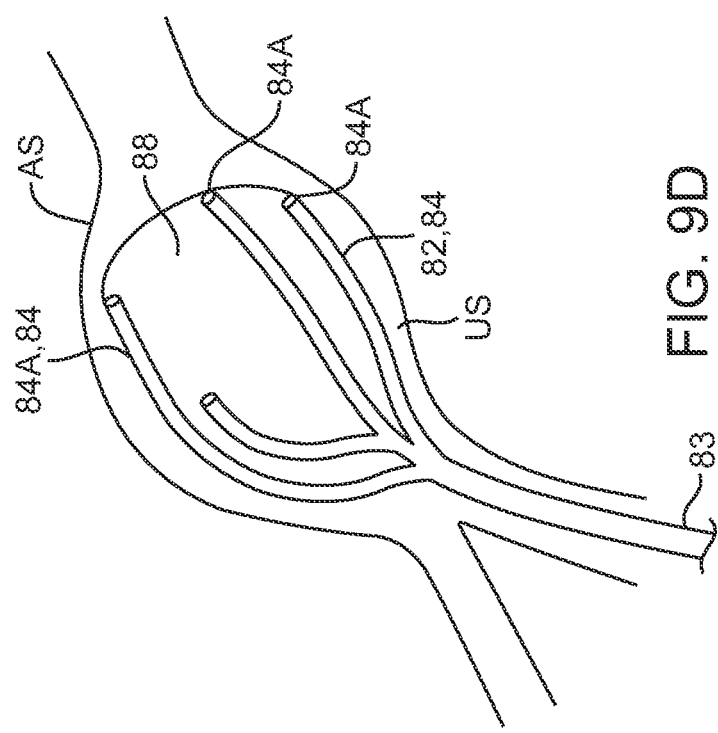
Figure 9E:
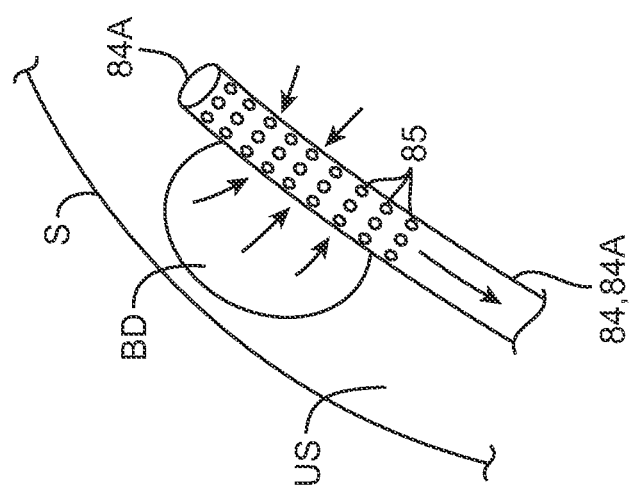

In another embodiment shown in FIGS. 9D and 9E the inflow portion 82 can comprise a series of arms 84A that are longitudinally or otherwise distributed around the circumference of structure 12. All or a portion of each arm can have a porous portion 84. Arms 84A can also serve to define a drainage volume or geometry 88. The inflow portion for both the embodiments of FIGS. 9D and 9E can be coupled to structure 12 using various joining methods known in the art including adhesive or ultrasonic welding, it can also be held in place by tension and/or frictional forces. The inflow portion of either embodiment can be configured to readily detached from structure 12 using e.g., a low force adhesive to allow the drain to be removed through use of a laparoscopic instrument. They also need not be attached to the structure but can exist as separate structure which can be attached to deliver catheter 14 or can be otherwise removed using a guidewire, laparoscopic instrument or other means. In various embodiments this can be facilitated through the use of retrieval element such as a loop, hook or like structure (not shown) attached to a portion of the drain device to allow it be retrieved from either an upstream or down stream approach.

Figure 9F:
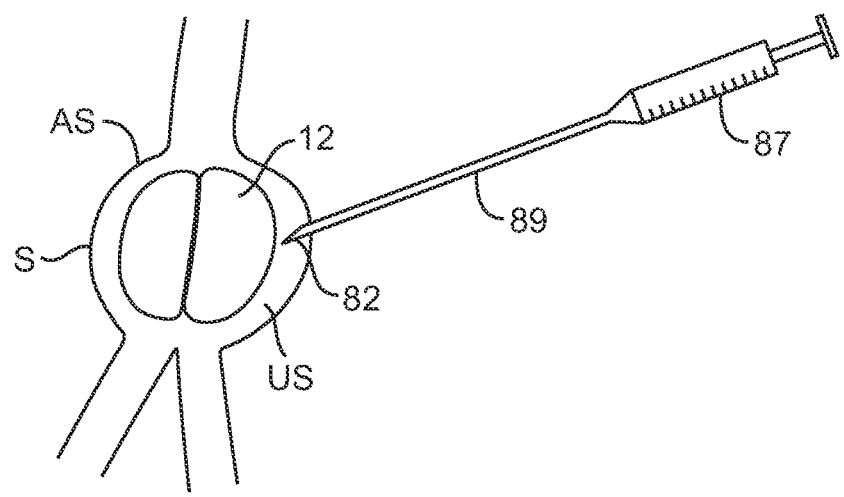

In an embodiment shown in FIG. 9F drain device 80 can comprise a needle 89 which is configured to be inserted into vessel space US by a laparoscopic approach or other method. A vacuum can then be pulled on the needle using a syringe or other vacuum source 87. This method allows the doctor to easily and quickly remove a desired volume of blood concurrent to the delivery of filling medium to structure 12. The doctor can make the withdrawal manually while monitoring pressure during filling so as to stay below a select pressure (e.g., 20% above the patients blood pressure). Also the withdrawal can be done automatically using a syringe pump. The rate can be adjusted manually and the pump can be coupled to a computer/processor having an algorithm that controls the withdrawal rate based on monitored pressure(s) at site AS.

Figure 10:
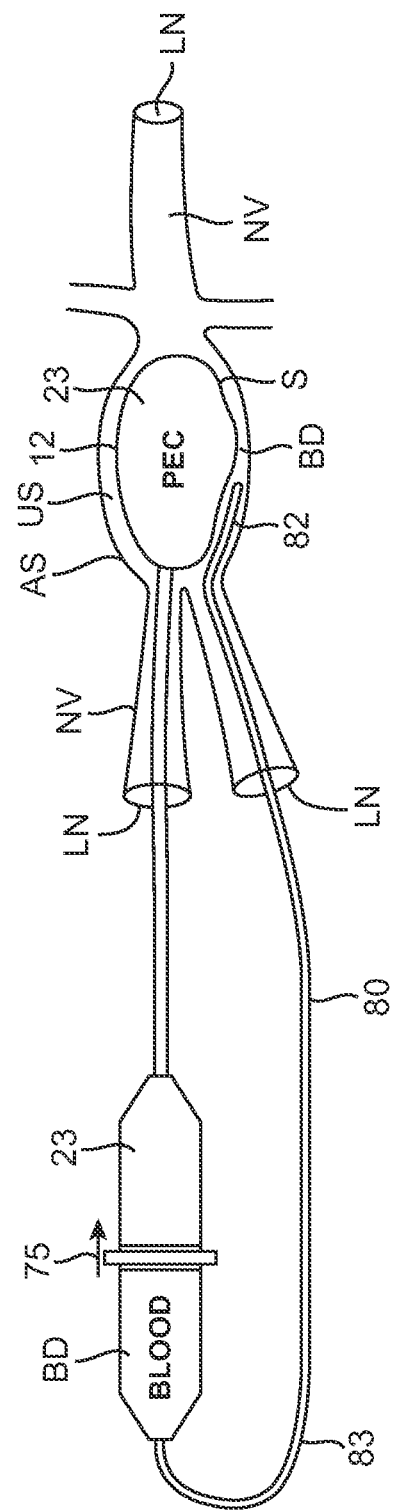
FIG. 10 illustrates a method for the concurrent removal of blood from the aneurysm site and filling medium injection into the filling structure.
Figure 12B:
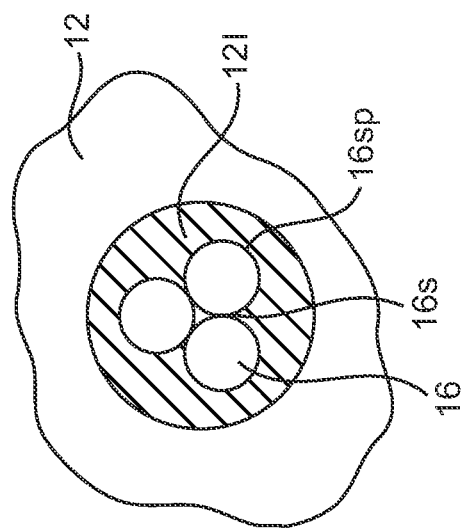
FIGS. 12A-B are lateral and cross sectional views illustrating embodiments of a multi-balloon support member that allows for the drainage of blood from the aneurysm site during inflation.
Figure 12A:
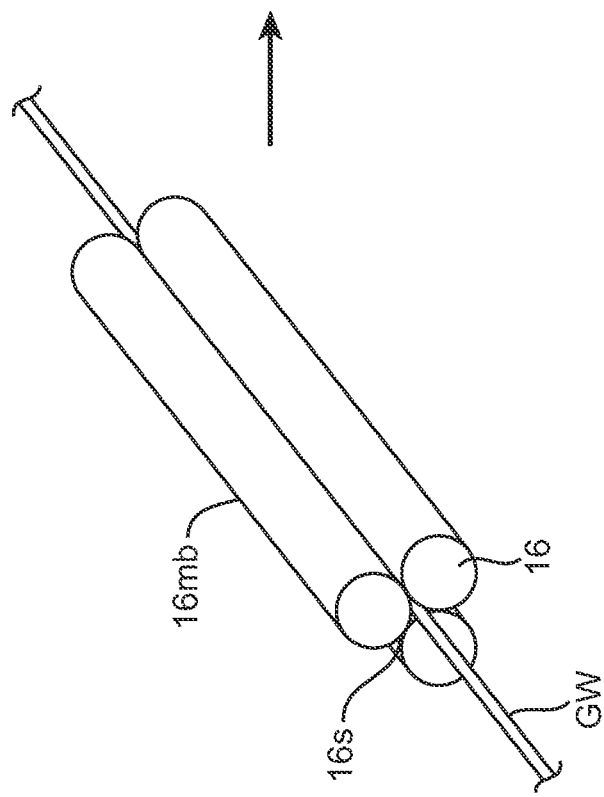

Referring now to FIG. 10, in a variation of the above embodiment, system 10 can be configured to allow for a substantially equal rate of blood removal from site AS as the flow rate of filling medium 23 injected into the filling structure 12 (and hence to the total volumes as well). The withdrawal and injection can be done simultaneously or near simultaneously and at substantially the same rate using a dual action syringe pump or other concurrent injection and withdrawal means 75 known in the art. Pressures can be monitored continuously during this procedure and the withdrawal rate and/or injection rate can be adjusted accordingly to maintain pressure below a threshold or other set point.

Outflow portion 83 will typically comprise a tube portion 86 (also called tube 86) that can be configured to extended proximally or distally from site AS into the lumen LN of the native vessels NV adjoining site AS. The tube can be extended various lengths into the vessels NV, e.g., several millimeters to several centimeters. In some embodiments where draining is done passively (as is discussed herein), the tube 86 will be positioned distally or downstream from site AS so to allow passive draining of blood due to the hydrostatic pressure forces exerted by blood or other fluid in space AS. In other embodiments where draining is done actively (e.g., from the use of a vacuum), tube 86 can be positioned proximally relative to site AS. For embodiments where the device is left in at site AS for post implant draining, the tube is preferably configured to only slightly extend into lumen LN of the native vessel and is configured to be located close to be close to lumen wall (e.g., several millimeters) to minimize contact area with flowing blood. The tube portion can also be sized to be connected to a subcutaneous or a cutaneous access device/fluidic connector or reservoir (not shown) to allow for cutaneous access and removal of blood.

Tube portion 86 can also be configured to be detachable from the remainder of the drain device by means of a guidewire, catheter or other minimally invasive method. This allows the physician to remove the tube portion at a selected time period post implant (e.g., two weeks) at which time it is no longer needed. Detachability can be achieved through the use of a reliable joint known in the art or a low force adhesive. Tube portion 86 can also include a retrieval element discussed herein.

In still other embodiments, tube portion 86 may be sized to extend all the way outside of the patients body through a vascular access site such as at the groin. This latter embodiment allows for the draining of blood and fluid both passively and actively by the application of vacuum. It can also be configured to be fluidly coupled to a pressure sensing member 65 so as to allow the draining of blood through the pressure sensing member.

In various embodiments, drain device 80 can be constructed from various non-thrombogenic biomaterials known in the art such as silicone, polyurethane and the like so as to maintain patentcy of both the inflow and the outflow portions. Also, all or a portion of the drain can have various coatings, for example, non-thrombogenic coatings such as a heparin based coating to provide additional thrombogenic protection for various periods of use. In preferred embodiments it can be constructed from expanded PTFE. Also, all or a portion of the drain can also be constructed from re-absorbable biomaterials known in the art so as to provide a drain function for a selected time period before being reabsorbed by the body. Also, the tube portion of the drain can be attached with a low force adhesive or otherwise treated to be detachable using minimally invasive methods. For embodiment employing a needle device, the needle can be fabricated from 304V or other stainless steel as well as superelastic materials such as NITINOL. It can also be fabricated from various flexible polymers known in the art. The needle and the other embodiments of the drain device can also include various fittings such as a Touhy Borst fitting or valve for connection to vacuum sources, pumps, pressure lines and the like.

In other approaches for draining blood from the vessel space US, the balloon support member or other mechanical support member can be shaped so as to not form a seal with the wall of the aneurysm or adjoining artery when they are in an expanded state. This allows blood to flow around the balloon/expansion device desirably both at the proximal and distal end of the device. Such embodiment also allows any blood located in vessel space US to flow out or be squeegeed out from the aneurysm site as the filling structure is expanded. Referring now to FIGS. 11A-11B, in specific embodiments, the balloon 16 can comprise a lobe shaped balloon 161 have a multi-lobed cross sectional profile 16$lp$ which allows blood to flow in the valleys 17V between the lobes 17 while peaks 17P of the lobes 17 provide support to maintain the tubular shape of the inner lumen 12$l$ of filling member 12. Valley 17$p$ can also be configured to allow for the passage of a pressure sensing member 63 from a proximal to a distal end of the balloon. Balloon 161 can have a selectable number of lobes 17, for example, between three and five lobes depending the upon size of lumen 12$l$ and the desired amount of blood flow. In one embodiment the balloon can have a three lobe profile 16$lp$.

Referring now to FIGS. 12A-13B, other embodiments a balloon that allows for blood flow through lumen 12$l$, can comprise a multi-balloon member 16$mb$ made of two or more individual balloons 16 that are joined together or share a common wall, for example, a three balloon member. These embodiments are configured to allow for blood flow in the spaces 16$s$ between the balloons when they are inflated. Such embodiments can have a multi-spherical cross-sectional profile 16$sp$. In a preferred embodiment shown in FIGS. 12A and 12B, a multi-balloon support member 16$mb$ can comprise three balloons and thus have a tri-spherical cross sectional profile 16$sp$. Use of such of an embodiment of a multi-balloon support member is illustrated in FIGS. 13A-B which show how blood can flow through the balloon space 16$s$ and thus allow for both flow through lumen 12$l$ and drainage of blood from space US when the balloon are inflated and the filling structure is being filled.

Figure 14C:
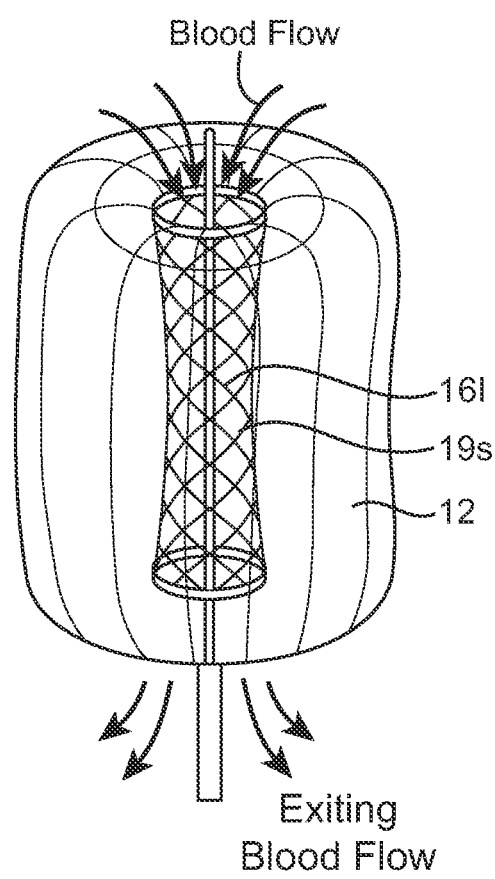
FIG. 14C illustrates use of the expandable stent structure to allow for the to allow the drainage of blood from the aneurysm site during expansion.

Referring now to FIGS. 14A-C, another embodiment for a support member that allows blood through lumen 12$l$ when in the expanded state can include and expandable shape memory stent 16$t$ comprising a plurality of flexible splines 19 that form a scaffolding structure 19$s$ that is able to support lumen 12. The stent can have a non-deployed state shown in FIG. 14A and an expanded or deployed state shown in FIG. 14B. The stent can be fabricated from various superelastic shape memory materials known in the art such as nickel titanium alloys. In a preferred embodiment, the stent is fabricated from NITINOL. The stent may also be coated with various non-thrombogenic coatings, including eluting coatings known in the art. Stent 16$t$ can be put into the expanded state by the application of either tension or compression from delivery catheter 14 or guidewire GW or another pull wire not shown. FIG. 14C illustrates how the scaffolding supports lumen 12*l* and how blood is able to readily flow through the stent when it is put into the expanded state.

Figure 15C:
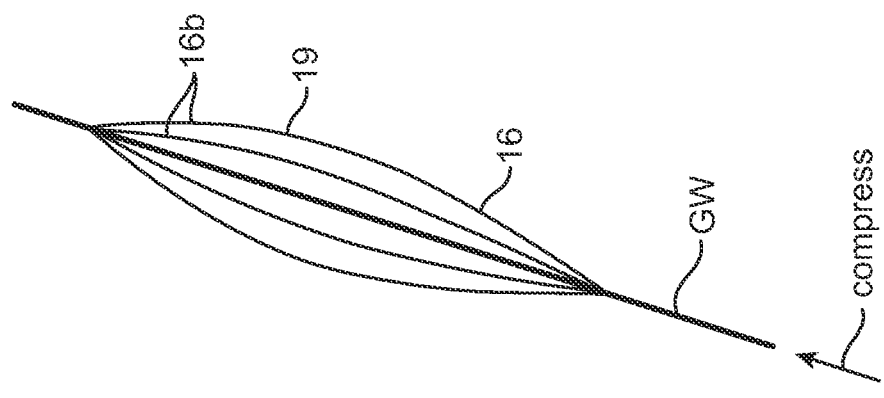
FIGS. 15A-C are perspective views illustrating embodiments of an expandable basket support member that allows for the drainage of blood from the aneurysm site during inflation. 15A is in the non-expanded state, 15B is partially expanded and 15C is in the fully expanded state.
Figure 15B:
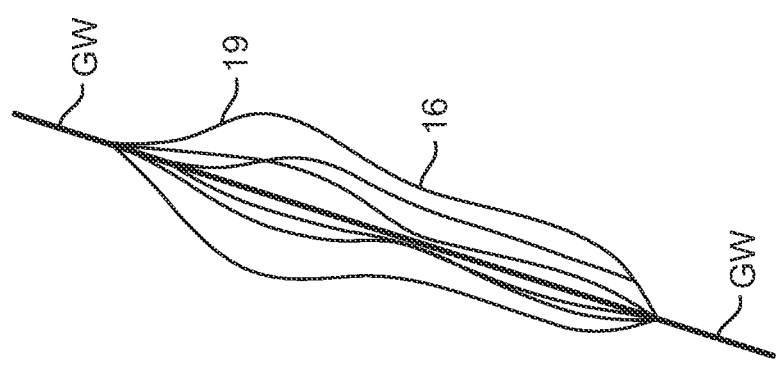
Figure 15A:
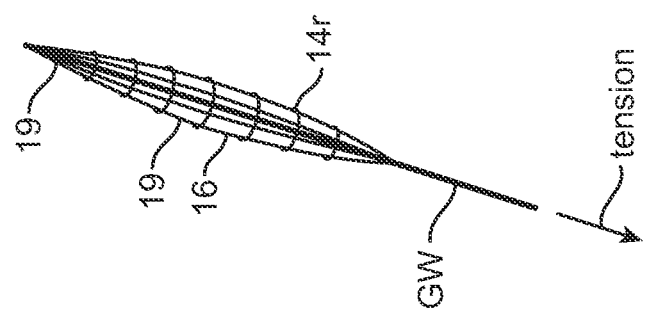

Another embodiment of an expandable mechanical support structure that allows blood flow is shown FIGS. 15A-15C. This structure is similar to stent 16 but comprises a basket like structure 16*b* that also is fabricated from a plurality of splines 19 that have an outwardly curved spring memory shape which they assume when they are released into the expanded state. The splines desirably have sufficient spring memory to hold lumen 12*l* open. Similar to stent 16*t*, the basket structure can be put into the expanded state through the application of tension or compression from guidewire GW or catheter 14. The splines can also be held in the contracted state through a series of ring constraints 19*r*. Alternatively the splines need not have an outwardly bowed spring memory but rather can be held in that position through the application of tension or compression from guidewire GW or catheter 14.

Figure 16A:
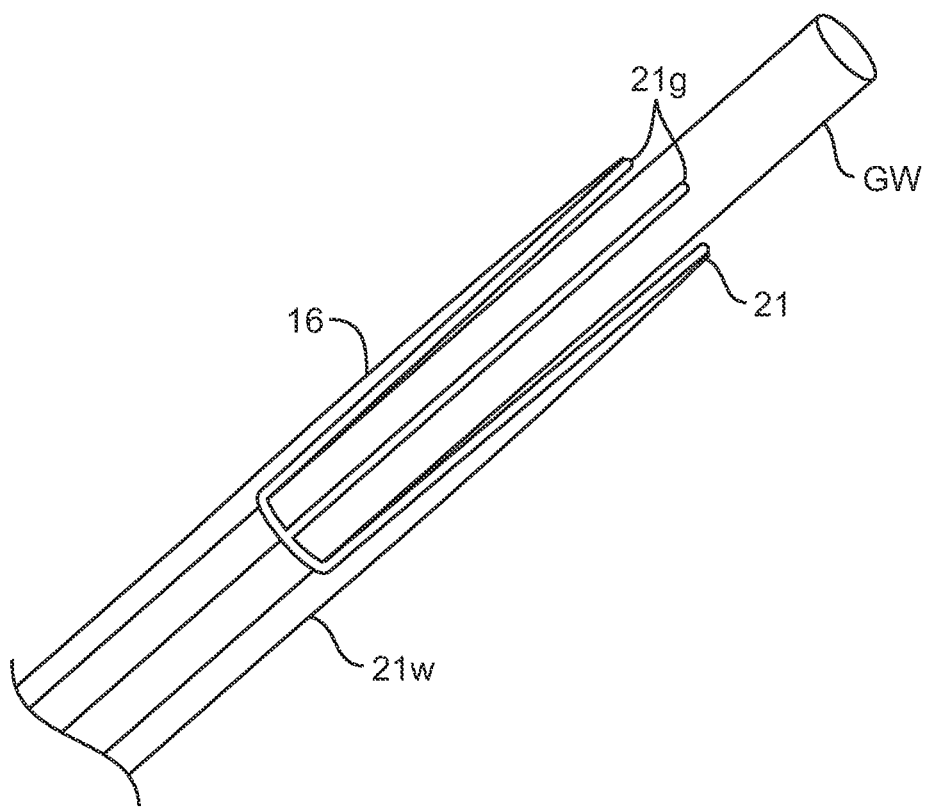
FIGS. 16A-B are perspective views illustrating embodiments of another expandable support member that allows for the drainage of blood from the aneurysm site during inflation. 16A is in the non-expanded state and 16 B is in the expanded state.
Figure 16B:
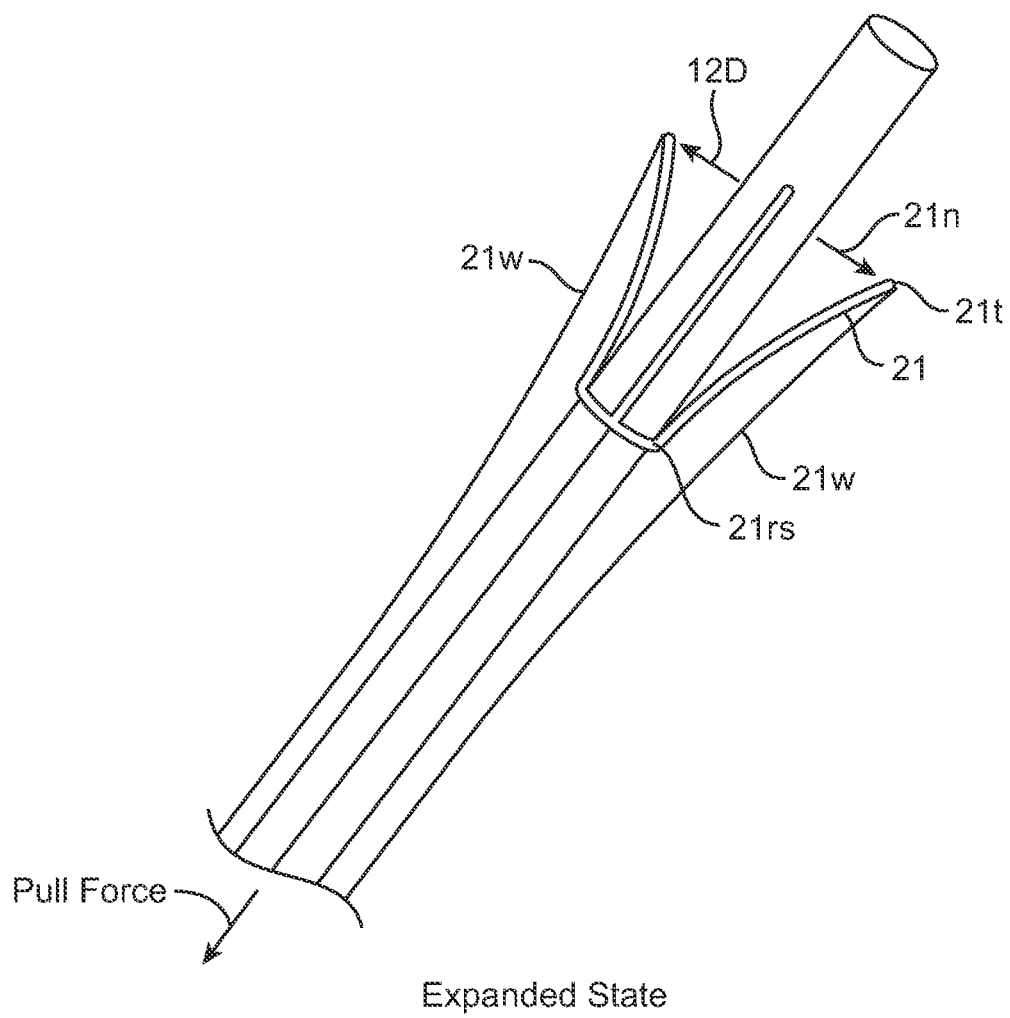

Yet another embodiment of an expandable mechanical support structure that allows blood flow is shown by FIGS. 16A-B. This embodiment comprises a mechanically expandable support structure 16 having a plurality of flexible spring arms members 21 that can be pulled into an expanded state by a series of connected pull wires 21*w*. Pull wires 21*w* can be positioned in guidewire lumen 18 or another lumen of catheter 14 and can be coupled to a common actuator (not shown) to pull all of them an equal amount at the same time. The actuator can have a locking feature to lock the arm members in the expanded state and also can be indexed for a selectable amount of outward radial expansion of the arm members so as to define a diameter 12D between opposing arm members for supporting lumen 12*l*. There can also be several groups of arms 21*g* members spaced longitudinally along catheter 14 to provide several rings of radial support 21 for supporting lumen 12*l*. Also, there can be partially radially constrained/supported by a ring structure 21*rs* positioned on catheter 14. Desirably, arm members 21 have sufficient spring memory in the straightened state such that they will resume this shape when released by pull wires 21*w*. Arm members 21 can be fabricated from various spring and shape memory metals known in the art as well as various flexible polymers known in the art. All or a portion of the arm members can be coated with a biomaterial coating including non-thrombogenic coating. Desirable the arm member tips 21*t* are configured to be atraumatic and can be either coated, smoothed or caped. They can also be pre-shaped to be either straight or curved and can have a number or radio-opaque or echogenic markers positioned along their lengths.

In other embodiments, filling member 12 can be configured so as not to need support during filling/inflation and also during the perfusion of blood through lumen 12*l* during filling. Referring now to FIGS. 17A-18B, one embodiment of such a filling member comprise a coiled structure 12*c* that has an open central lumen 12*l* for blood flow which does not need support during filling. Specifically the coiled structure has sufficient radial strength that it does not need radial support similar to maintain its shape when inflated, similar to the mechanics of an inner tube. In one embodiment, the coiled structure can comprise a series of individual inflatable coils 12*ic* having an inner tube like structure that are joined and fluidically coupled to one another to allow simultaneous filling/inflation as is shown FIG. 17B.

Figure 19:
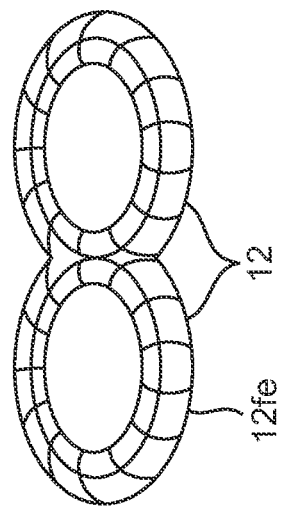
FIG. 19 is a perspective view of a continuously coiled filling structure having a FIG. 8 shape.
Figure 18:
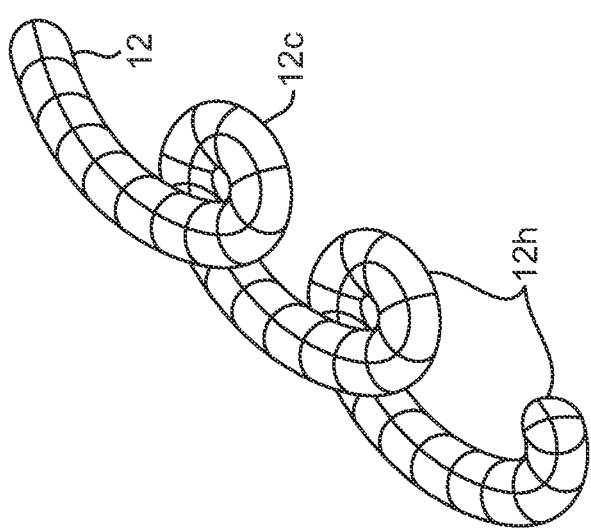
FIG. 18 is a perspective view of a continuously coiled helical filling structure.

In another embodiment shown in FIG. 18, the coiled structure 12*c* can comprise a continuously coiled structure 12*cc* that has a helical shape 12*h* when unconstrained. It can then be wrapped or packed around catheter 14 to assume a substantially cylindrical coiled shape when deployed in vivo. This structure can also be deployed from catheter 14 into an aneurysm site in an extruded like manner using an overtube or guiding catheter. In another embodiment shown in FIG. 19, structure 12 can have a "figure eight shape" 12*fe* which can be configured for treating aneurysm at or near a vessel bifurcation. Various embodiments of coiled structure 12*c* can be fabricated from various biocompatible elastomers known in the art including silicone and polyurethane and co-polymers thereof. They can also be internally supported by braids, struts or other support element to help maintain the patency of their central lumen.

Referring now to FIG. 20A-20C, a method of using a coiled filling structure 12*c* is illustrated. The structure can be position in the desired site AS, using delivery catheter 14. Then coiled structure 12*c* is filled/inflated with filling medium 23, without the need for a support structure 16. However, one can be used if so desired by the physician. The structure can be filled/inflated in such a manner as to squeeze out blood from space US in a piston like manner. That is, as each individual coils of the structure becomes inflated it push blood from space US down the vessel in the direction of inflation DI (e.g., proximal in the embodiment shown) until all of the coils are inflated and all of the blood is forced out from space US. Each individual coil 12*c* acts as fluidic seal 12*fs* which prevents blood from flowing backward against the direction of inflation DI, thus forces the remaining blood in space US to travel in the path of least fluidic resistance which is in the direction of inflation. In use, such embodiments minimize the likelihood of blood becoming trapped in space US and also excessive pressure from being exerted against the aneurysm wall thus minimizing the risk of dissection. Similar to other method embodiments discussed herein, pressure monitoring can be done throughout the filling and deployment process to control filling, determine endpoint and further reduce the risk of over-pressurization.

FIGS. 21A-C illustrate a variation of the method describe above adapted for used with an aneurysm near a vessel bifurcation. In these embodiments a first and second coiled filling structure 112*c* and 212*c* are used. Typically each structure will be positioned and then filled sequentially as is shown in FIGS. 21B-C though the physician can elect to do simultaneous or otherwise concurrent fillings. In either case, pressure monitoring can be done throughout the procedure as described above to both control the filling process and determine endpoint.

Figure 22A:
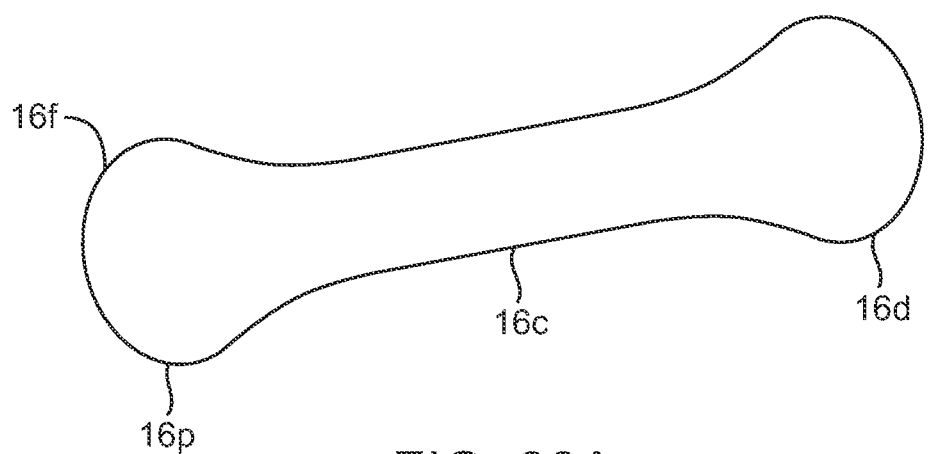
FIGS. 22A-B are perspective and lateral views illustrating an embodiments of a inflatable support member having flared end portions.
Figure 22B:
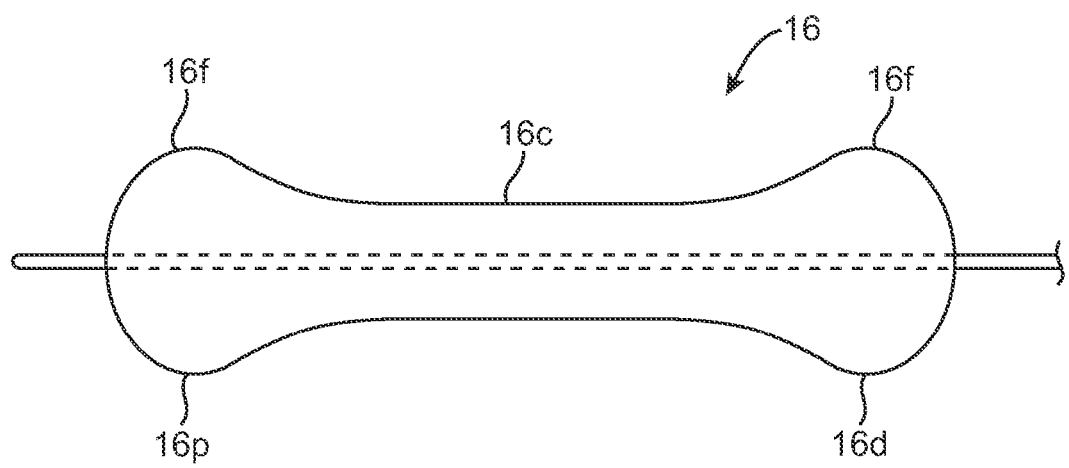
Figure 22C:
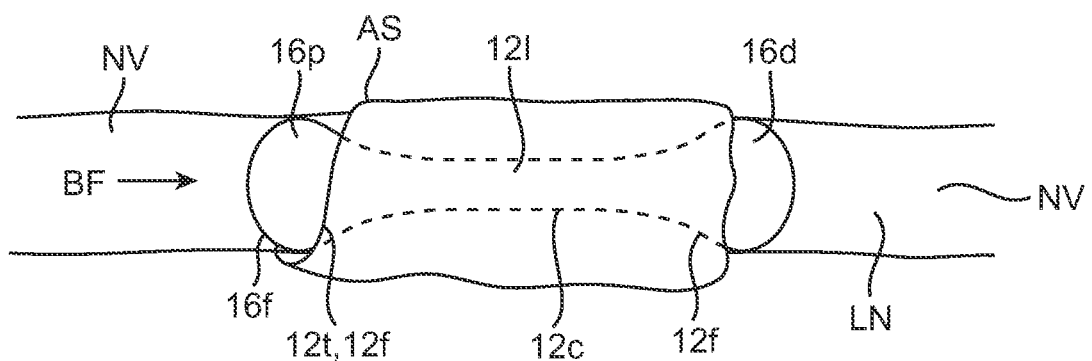
FIG. 22 C illustrates use of the flared support balloon to produce a filling structure blood flow lumen with flared end portions.

Referring now to FIGS. 22A-22C, in some embodiments, the balloon support member 16 can have a dog bone 16*db* or like shape (e.g., a cassini oval) such that the proximal and distal end portions 16*p* and 16*d* of the balloon have an outwardly flared shape 16*f* or otherwise has a larger diameter than the balloon central portion 16*c*. One or both of the end portions 16*p* and 16*d* of the inflated balloon can extend at least partially out of the filling structure 12 into the native vessel lumen LN. This configuration serves to shape the lumen 12*l* of the hardened filling structure such that the proximal and distal ends of the formed lumen 12*lp* and 12*ld* have an outwardly flared shape 12*f* (relative to the central portion 121*c*) which roughly corresponds to flared shape 16*f*. This flared shape 12*f* serves to provide a smooth transition 12*t* in diameter from the native vessel lumen NL to the formed lumen 12*l* of structure 12 and in particular, minimizes the surface of the area of the formed lumen that is normal to the direction of blood flow BD through the artery. This later configuration serves to minimize an amount of sheer stress on the formed and adjacent native lumens as well as reduce an amount of retrograde flow and turbulence in vessel regions within and adjacent the prosthesis. These fluid dynamic factors in turn serve to reduce the likelihood of the formation of stenosis in the region of the prosthetic.

Figure 23:
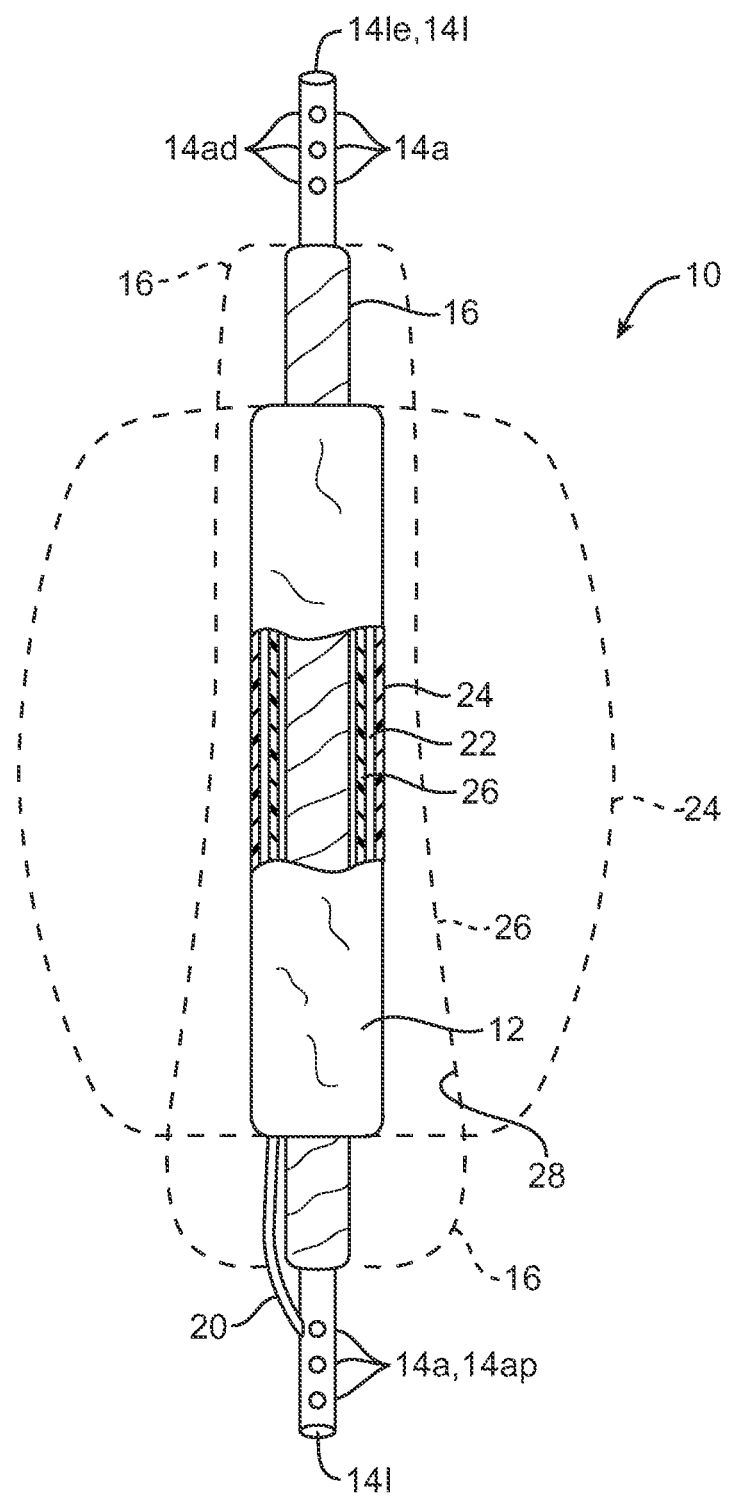
FIG. 23 illustrates an embodiment of the prosthesis system comprising a filling structure mounted over a delivery catheter in which the delivery catheter includes a perfusion lumen and proximal and apertures for the perfusion of blood through the lumen during filling of the filling structure.

Referring now to FIG. 23, in other embodiments, perfusion during inflation of the balloon support member can also be achieved by the use of a perfusion lumen 14*l* with proximal and distal apertures 14*ap* and 14*ad* for the inflow and outflow of blood. The proximal and distal apertures 14*ap* and 14*ad* are desirably positioned on the delivery catheter so as to allow blood to enter the proximal apertures, flow through the delivery catheter lumen and exist the distal apertures and/or distal end of the lumen 14*le* when the balloon support 16 is inflated before, during or after filling of filling structure 12. Perfusion can be enhanced through the use of pressure monitoring to position the inflow and outflow apertures in areas with greatest blood flow and/or pressure gradient.

CONCLUSIONS

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the aneurysm repair system, and prostheses can be adapted to be utilized in the thoracic region of the aorta or other vasculatures of the body including, without limitation, the cerebral vasculature and the femoral and popliteal vasculatures. Also, embodiments of dual filling structure system can be adapted to treat aneurysms at or near any bifurcation in the arterial vasculature.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as stand alone elements. Hence, the scope of the present invention is not limited to the specifics of the described embodiments, but is instead limited solely by the appended claims.

The invention claimed is:

1. A method for treating an aneurysm in a patient, the method comprising:
measuring a blood pressure of the patient at an aneurysm site;
determining a maximum blood pressure value over a period of time;
positioning at least one double-walled filling structure across the aneurysm, the double-walled filling structure having an inner wall and an outer wall that are conformable;
deploying a scaffold positioned within the double-walled filling structure, the scaffold adapted to allow blood flow therethrough;
filling the at least one double-walled filling structure with a hardenable fluid filling medium so that the outer wall conforms to an inside of the aneurysm and the inner wall conforms to the scaffold so as to form a generally tubular lumen to provide for blood flow, wherein the inner wall is conformable to differing diameters along the generally tubular lumen such that the scaffold shapes the generally tubular lumen to conform an upper and lower end of the tubular lumen to aortic and iliac walls, respectively, wherein the blood flow directly contacts a surface of the inner wall, and wherein the at least one double-walled filling structure substantially fills the aneurysm when filled with the fluid filling medium;
supporting the tubular lumen with the scaffold during filling and/or after the filling of the at least one double-walled filling structure;
monitoring a filling pressure during filling of the at least one double-walled filling structure;
controlling filling of the filling medium into the double-walled filling structure in response to the monitored pressure so as to maintain filling pressure at or above the maximum blood pressure value and below a threshold pressure within a range of about 100% to 140% of the patient's blood pressure; and
supporting the tubular lumen with the scaffold while the filling medium hardens within the at least one double-walled filling structure.

2. The method of claim 1, further comprising:
determining an end point of filling the at least one double-walled filling structure with the filling medium in response to a pressure increase of the monitored filling pressure.

3. The method of claim 1, wherein controlling filling comprises controlling a flow rate of the filling medium into the double-walled filling structure.

4. The method of claim 1, wherein controlling filling comprises decreasing or stopping flow of the filling medium when the monitored filling pressure exceeds the threshold pressure.

5. The method of claim 1, wherein the threshold pressure is determined based on any of a systolic pressure, a diastolic pressure, a time averaged pressure, or any combination thereof.

6. The method of claim 1, wherein the threshold pressure is further determined based on a dimensional, mechanical and/or morphological characteristic of the aneurysm.

7. The method of claim 6, wherein the dimensional characteristic includes any of an aneurysmal wall thickness, a size of the aneurysm, a shape of the aneurysm, or any combination thereof.

8. The method of claim 1, further comprising:
monitoring a volume of medium injected into the double-walled filling structure; and
controlling a flow rate of the filling medium responsive to the monitored volume.

9. The method of claim 1, wherein monitoring of the filling pressure comprises monitoring of a delivery pressure of the filling medium.

10. The method of claim 1, wherein monitoring of the filling pressure comprises monitoring of a composite pressure, the composite pressure comprising a combination of a pressure within an internal space of the double-walled filling structure and a pressure between an external wall of the double-walled filling structure and an inner wall of the aneurysm.

11. The method of claim 1, wherein the filling pressure is monitored using any of a gage, a pressure sensor positioned in or on the double-walled filling structure, or a filling member coupled to the double-walled filling structure.

12. The method of claim 11, wherein the pressure sensor is disposed on a catheter or a guide wire.

13. The method of claim 1, wherein a flow of the filling medium is stopped by means of a valve coupled to the double-walled filling structure or an associated filling tube coupled thereto.

14. The method of claim 13, wherein the valve is a control valve, a pressure sensitive valve, or an electronic valve.

15. The method of claim 13, wherein controlling filling comprises decreasing or stopping flow of the filling medium by sending a signal to the valve based on the monitored filling pressure.

16. The method of claim 1, wherein the scaffold comprises an expandable stent.

17. The method of claim 16, wherein the expandable stent has sufficient radial strength to withstand a circumferential pressure from the at least one double-walled filling structure when filled at the threshold pressure.

18. The method of claim 1, wherein the at least one double-walled filling structure is a first double-walled filling structure, the method further comprising:
    positioning a second double-walled filling structure across the aneurysm generally adjacent to and parallel with the first double-walled filling structure;
    filling the second double-walled filling structure with the fluid filling medium so that an outer wall conforms to the inside of the aneurysm and an inner wall forms a generally tubular lumen to provide for blood flow, wherein the blood flow directly contacts a surface of the inner wall, such that the first and second double-walled filling structures, in combination, substantially fill the aneurysm when filled with the fluid filling medium;
    supporting the tubular lumen of the second double-walled filling structure with a support structure during filling and/or after the filling of the second double-walled filling structure;
    monitoring a filling pressure of the second double-walled filling structure during filling of the second double-walled filling structure;
    controlling filling of the fluid filling medium into the second double-walled filling structure in response to the monitored filling pressure of the second double-walled filling structure based on a threshold pressure relative a blood pressure of the patient, wherein the threshold pressure is in the range of about 100% to 140% of the patient's blood pressure;
    supporting the tubular lumen of the second double-walled filling structure while the fluid filling medium hardens, at least in part, within the second double-walled filling structure; and
    removing the support structure from the second double-walled filling structure after the fluid filling medium has hardened, at least in part.

19. The method of claim 18, wherein the first and second double-walled filling structures are filled concurrently, at least in part, or sequentially within the aneurysm.

20. The method of claim 19, wherein threshold pressure is adjusted for at least one of the first and second double-walled filling structures based on the filling pressure of the other of the first and second double-walled filling structures when the first and second double-walled filling structures are filled concurrently.

21. The method of claim 1, wherein the inner and outer walls are formed of a non-compliant material.

22. The method of claim 21, wherein the inner wall is dimensioned so as to be slightly larger than the desired tubular lumen so as to allow expansion to a larger diameter along an upper or lower end of the tubular lumen during deployment so as to conform with the aortic and iliac walls.

23. A method for treating an aneurysm in a patient, the method comprising:
    positioning at least one expandable filling structure within the aneurysm, the filling structure having a conformable inner wall and a conformable outer wall;
    deploying a support structure positioned within the filling structure, the support structure adapted to allow blood flow therethrough;
    filling the at least one filling structure with a fluid filling medium so that the outer wall conforms to an inside of the aneurysm and the inner wall conforms to the support structure so as to form a generally tubular lumen to provide for blood flow, wherein the blood flow directly contacts a surface of the inner wall, and wherein the at least one filling structure substantially fills the aneurysm when filled with the fluid filling medium;
    supporting the tubular lumen with a support structure during filling and/or after the filling of the at least one filling structure;
    controlling pressurized filling of the filling medium into the filling structure in response to monitored pressure based on a threshold pressure relative a blood pressure of the patient, wherein the threshold pressure is in the range of about 100% to 140% of the patient's blood pressure; and
    supporting the tubular lumen with the support structure while the filling medium hardens within the at least one filling structure.

24. The method of claim 23, determining an end point of filling based on combining a measured filling pressure together with a delivered volume of filling medium.

25. The method of claim 23, wherein controlling pressurized filling comprises using a mechanical pressure relief valve configured to relieve pressure when filling pressure exceeds the threshold pressure.

* * * * *